(12) United States Patent
Seela et al.

(10) Patent No.: US 7,566,775 B2
(45) Date of Patent: Jul. 28, 2009

(54) $N^8$- AND $C^8$-LINKED PURINE BASES AND STRUCTURALLY RELATED HETEROCYCLES AS UNIVERSAL NUCLEOSIDES USED FOR OLIGONUCLEOTIDES HYBRIDIZATION

(75) Inventors: Frank Seela, Osnabrueck (DE); Frank Bergmann, Iffeldorf (DE); Dieter Heindl, Tutzing (DE); Herbert Von der Eltz, Weilheim (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 455 days.

(21) Appl. No.: 11/338,149

(22) Filed: Jan. 23, 2006

(65) Prior Publication Data
US 2006/0135462 A1    Jun. 22, 2006

Related U.S. Application Data

(63) Continuation of application No. 10/221,306, filed as application No. PCT/EP01/03458 on Mar. 27, 2001, now Pat. No. 7,063,945.

(30) Foreign Application Priority Data

Mar. 28, 2000  (EP) ................... 00106017
Apr. 20, 2000  (EP) ................... 00108023

(51) Int. Cl.
  C07H 21/02    (2006.01)
  C07H 21/04    (2006.01)
  C07H 21/00    (2006.01)
  C12Q 1/68     (2006.01)
  C12P 19/34    (2006.01)

(52) U.S. Cl. ............ 536/23.1; 536/24.3; 536/24.33; 536/25.3; 435/6; 435/91.1; 435/91.2

(58) Field of Classification Search ............ 435/6, 435/91.1, 91.2; 536/23.1, 24.3, 24.33, 25.3
See application file for complete search history.

(56) References Cited

U.S. PATENT DOCUMENTS 5,789,562 A   8/1998   Seela et al.
6,066,720 A   5/2000   Seela et al.

FOREIGN PATENT DOCUMENTS

JP    8-3186    9/1996

OTHER PUBLICATIONS

Seela, F., et. al., 1992, <<146, 8-Azaadenine 2',3'-Dideoxyribonucleosides: Synthesis via 1,2,3-Triazolo[4,5-d]pyrimidinyl1 Anions, *Helvetica Chimica Acta*, 75:1885-1896.

Primary Examiner—Jezia Riley
(74) Attorney, Agent, or Firm—Olga Kay; Charles M. Doyle

(57) ABSTRACT

The present invention is directed to a nucleic acid binding compound comprising $N^8$- or $C^8$-linked purine bases or structurally related heterocycles, a compound useful for the preparation of such compound, a binding product of this nucleic acid binding compound with a nucleic acid, a method for the determination of a nucleic acid using said compound, and several uses of 8-linked purine bases and structurally related heterocycles. Compounds according to the present invention have advantageous properties when used in hybridization methods.

16 Claims, 12 Drawing Sheets

1

2

3

4

5

6

Watson-Crick reversed Watson-Crick reversed Watson-Crick reversed Hoogsteen reversed Watson-Crick reversed Hoogsteen

XXV

XXVI

XXVII

XXVIII

XXIX

XXX

XXXI

XXXII

XXXIII

XXXIV

XXXV

XXXVI

XXXVII

XXXVIII

XXXIX

XL

XLI

XLII

XLIII

XLIV

XLV

XLVI

XLVII

1a: R = OMe
1b: R = NH₂

2a: R = OMe
2b: R = NH₂

$N^8$- AND $C^8$-LINKED PURINE BASES AND STRUCTURALLY RELATED HETEROCYCLES AS UNIVERSAL NUCLEOSIDES USED FOR OLIGONUCLEOTIDES HYBRIDIZATION

This application is a continuation of U.S. application Ser. No. 10/221,306, filed Sep. 10, 2002, now U.S. Pat. No. 7,063, 945, which is a 35 U.S.C. § 371 national phase filing of International Application No. PCT/EP01/03458, filed Mar. 27, 2001, the contents of which are hereby incorporated by reference therein.

BACKGROUND OF THE INVENTION

1. Field of the Invention

The present invention is directed to a nucleic acid binding compound comprising $N^8$- or $C^8$-linked purine bases or structurally related heterocycles, a compound useful for the preparation of such compound, a binding product of this nucleic acid binding compound with a nucleic acid, a method for the determination of a nucleic acid using said compound, and several uses of 8-linked purine bases and structurally related heterocycles.

2. Description of the Related Art

The synthesis of some $C^8$-glycosylated purine derivates is described in Czech. Chem. Comm. (Vol 34, p. 247), Heterocycl. Chem. (Vol 12, p. 111) and Journal of Medicinal Chemistry (Vol 33, p. 2750-2755). Examples of $N^8$-glycosylated purine derivates are shown in Helv. Chim. Acta (Vol. 72, p. 1527), Zh. Org. Khim. (Vol 12, p. 1131) and Helv. Chim. Acta (Vol 76, p. 2184-2193). However, there is no disclosure to use these non-natural bases as universal bases capable of base pairing with each of the four natural bases when incorporated in nucleic acids.

Some examples of 8-aza-7-deazaadenine coupled to a sugar moiety at its $N^8$-position are known in the art. In Helv. Chim. Acta (Vol 72, p. 868-881), there is disclosed the synthesis of 8-aza-7-deazaadenine $N^8$-(β-D-2'-deoxyribofuranoside). The synthesis of $N^6$-methylated-8-aza-7-deazaadenine $N^8$-(β-D-2'-deoxyribofuranoside) is shown in Helv. Chim. Acta (Vol 71, p. 1813-1823). However, there is no disclosure showing the advantages using such nucleotides as universal bases.

In Biochemistry (Vol 15, p. 1005-1015), there is disclosed the synthesis of 8-aza-7-deazaadenine $N^8$-(β-D-ribofuranosyl) (A*). Also shown is the enzymatic polymerization of ADP and A*DP in the presence of polynucleotide phosphorylase. However, there is no disclosure on the synthesis of oligonucleotides having a defined sequence containing other bases than those two. The hybridization behavior of these polymers is not described. Also no hint is given that these modified bases can be used in hybridization methods.

The present invention is particularly useful for nucleic acid hybridization methods, for example in nucleic acid determinations in analytics, especially in the field of health care. It can also be used for in-vitro-mutagenesis. It can also be applied in the pharmaceutical field, for example in oligonucleotides to be used as antisense oligonucleotides.

Nucleic acids have been found to be useful analytes for the determination of the presence or absence of genes or microorganisms in human body fluid, food or environment. Especially since the introduction of nucleic acid amplification techniques like the Polymerase Chain Reaction (PCR, see U.S. Pat. No. 4,683,202) the determination of nucleic acids is widely used, because of their good sensitivity.

The amplified nucleic acids can be determined using a variety of different techniques, dependent from the particular purpose. Most assays require the use of a probe which is either immobilized or immobilizable or is labeled by attachment of one or more reporter groups. A reporter group has the characteristics to be itself capable to be determined or it can be reacted with reagents that make the probe determinable via said reporter group. Thus, for example, probes that are labeled by reporter groups can be determined, as can be hybrids that contain the probe and a nucleic acid to be determined.

Regarding the optional amplification step as well as the probe hybridization step the hybridization behavior of the oligonucleotides used as primers and probes is very important. Dependent from the particular purpose, there are many proposals to include modified or non-natural heterocyclic groups instead of natural nucleobases in such oligonucleotides in order to improve the hybridization method.

An example of such an non-natural group is 7-deaza-dGTP which, when introduced into a nucleic acid replacing dGTP reduces band compression in sequencing gels (EP-B-0 286 028).

Nucleic acid determination is largely based on the fact, that the natural canonical bases A, C, G and T are only able to base pair with only one of the four natural bases. However the different stability of A paired with T compared to G paired with C could be a problem, because therefore the melting point of an hybrid not only depends on the length of the probe oligonucleotide but also on its GC-content.

In methods for screening of a nucleic acid in the case that only the amino acid sequence of the accompanying protein is available there is another problem. In that case the nucleic acid sequence can be deduced from the amino acid sequence. However the redundancy of the genetic code leads to a multitude of different sequences. Mixtures of oligonucleotides that take this redundancy into account must be synthesized and used for screening the potential DNA or RNA candidates.

An alternative approach uses less discriminatory base analogues. Such base is defined as a universal or ambiguous base, the corresponding nucleosides are named universal or ambiguous nucleosides. A universal base is one which pairs with some or all of the natural bases without major discrimination. Hypoxanthine for which the term universal base was coined is widely used as universal base, because it can form hydrogen bonds with all four natural bases (Y. Takahashi, K. Kato, Y. Hayashizaki, T. Wakabayashi, E. Ohtsuka, S. Matsuki, M. Ikehara, K. Matsubara, Proc. Natl. Acad. Sci. USA 1985, 1931-1935). When 2'-deoxyinosine (see FIG. 1, 1), the nucleoside of hypoxanthine, is incorporated into a 12-mer duplex opposite each of the four natural nucleosides they show a wide range of thermal stability represented by $T_m$-value differences of 15° C. (F. Seela, K. Mittelbach, Nucleosides, Nucleotides 1999, 18, 425-441). This shows that hypoxanthine does not base pair equally with the other bases. Furthermore, hypoxanthine being used in PCR primers behaves like guanine. Other universal nucleosides are the compounds P (see FIG. 1, 2) and K (see FIG. 1, 3) (P. Kong Thoo Lin, D. M. Brown, Nucleic Acids Res. 17, 10373-10383; D. M. Brown, P. Kong Thoo Lin, Carbohydrate Res., 216, 129-139). They were chosen as their amino-imino tautomeric forms of their bases are much more to unity than the normal bases. The nucleoside P can form Watson-Crick base pairs with the purine nucleosides dA and dG while the nucleoside K forms base pairs with dT and dC.

Apart from the nucleosides forming hydrogen bonds there are a number of universal residues which possess no hydrogen bonding capabilities. The electronic charge distribution of such heterocycles are good candidates for base stacking abasic sites (see FIG. 1, 4) (T. A. Milican, G. A. Mock, M. A. Chaunncy, T. P. Patel, M. A. W. Eaton, J. Gunning, S. D. Cutbush, S. Neidle, J. Mann, Nucleic Acids Res. 1984, 12, 7435-7453), and replacement of the natural bases by 5-nitroindol (see FIG. 1, 5) (D. Lokes, D. M. Brown, Nucleic Acids Res. 1994, 22, 4039-4043), 3-nitropyrrol (see FIG. 1, 6) (D. E. Bergstrom, P. Zhang, W. Travis Johnson, Nucleic Acids Res. 1997, 25, 1935-1942) has been used for such work.

All proposals known now have some disadvantages. Therefore, there is still a need to provide nucleic acid binding compounds like primers and probes containing universal bases capable to better base pair with each of the four natural bases.

DESCRIPTION OF THE INVENTION

Figure 1:
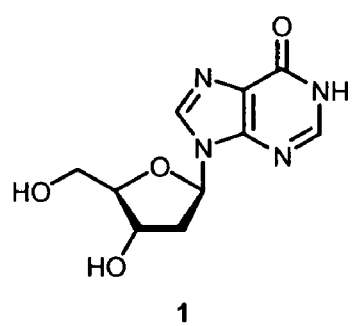
FIG. 1 shows various compounds which have been proposed as universal bases in the prior art.
Figure 1:
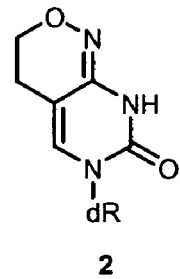
Figure 1:
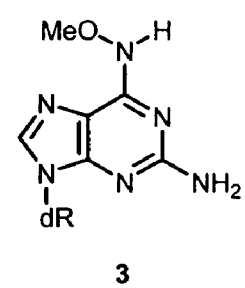
Figure 1:
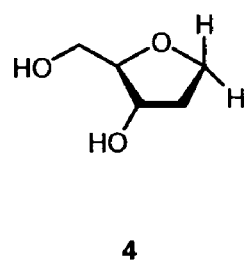
Figure 1:
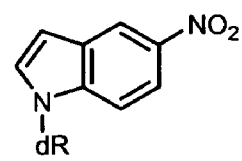
Figure 1:
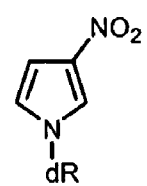
Figure 2:
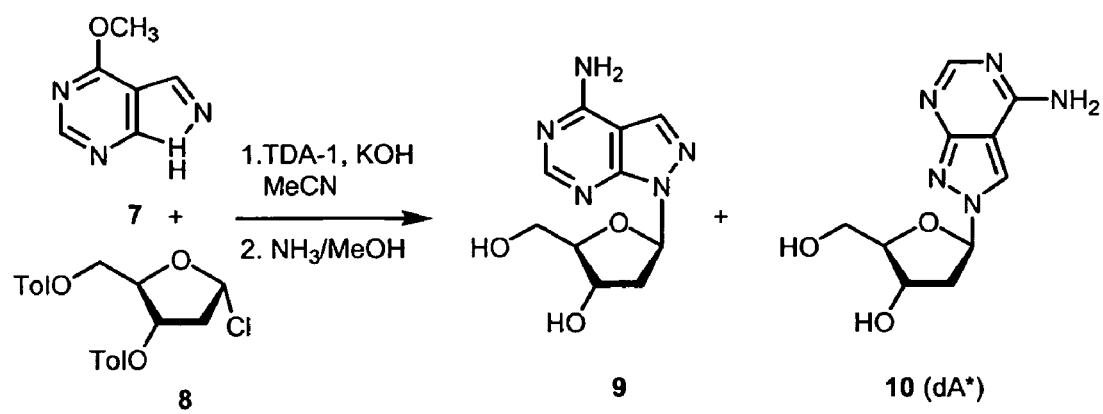
FIG. 2 shows the $N^9$ and $N^8$ glycosylation of pyrazolo[3,4-d]pyrimidine with 2'-deoxyribofuranosyl chloride.

The subject of the present invention is a nucleic acid binding compound comprising a backbone, said backbone having attached heterocyclic groups capable of base pairing to natural nucleobases characterized in that at least one of said heterocyclic groups is a group of the general formula I

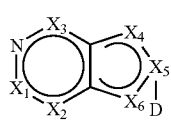

Formula I wherein $X_1$ is independently from $X_4$, $X_5$ and $X_6$ selected from the group of N and $CR^1$, and $X_1$ is $CR^1$ if each of $X_2$ and $X_3$ is N, $X_2$ is independently from $X_4$, $X_5$ and $X_6$ selected from the group of N and $CR^2$, and $X_2$ is $CR^2$ if each of $X_1$ and $X_3$ is N, $X_3$ is independently from $X_4$, $X_5$ and $X_6$ selected from the group of N and $CR^3$, and $X_3$ is $CR^3$ if each of $X_1$ and $X_2$ is N, $X_4$ is independently from $X_1$, $X_2$ and $X_3$ selected from the group of N, $NR^{35}$ and $CR^4$, if $X_5$ is C and $X_6$ is $NR^{35}$, then $X_4$ is $CR^4$ or N, if $X_5$ is C and $X_6$ is N, then $X_4$ is $NR^{35}$, and if $X_5$ is C and $X_6$ is $CR^{34}$, then $X_4$ is $NR^{35}$, and if $X_5$ is N, then $X_4$ is N or $CR^4$, $X_5$ is independently from $X_1$, $X_2$, $X_3$, $X_4$ and $X_6$ selected from the group of N and C, $X_6$ is independently from $X_1$, $X_2$ and $X_3$ selected from the group of N, $NR^{35}$ and $CR^{34}$, if $X_5$ is C and $X_4$ is $NR^{35}$, then $X_6$ is $CR^{34}$ or N, if $X_5$ is C and $X_4$ is N, then $X_6$ is $NR^{35}$, if $X_5$ is C and $X_4$ is $CR^4$, then $X_6$ is $NR^{35}$, and if $X_5$ is N, then $X_6$ is N or $CR^{34}$, $R^1$, $R^2$, $R^3$, $R^4$ and $R^{34}$ are independently selected from the group consisting of —H, -halogen, —$OR^{13}$, —$SR^{19}$, —($C_1$-$C_{10}$)-alkyl, —($C_2$-$C_{10}$)-alkenyl, —($C_2$-$C_{10}$)-alkynyl, —$NO_2$, —$NR^5R^6$, -cyano, and —C(=O)$R^{11}$, $R^{11}$ is selected from the group consisting of —OH, —($C_1$-$C_6$)-alkoxy, —($C_6$-$C_{22}$)-aryloxy, and $NHR^{12}$, $R^5$, $R^6$, $R^{12}$, $R^{13}$, $R^{19}$ and $R^{35}$ are selected independently from the group consisting of —H, —($C_1$-$C_{10}$)-alkyl, —($C_2$-$C_{10}$)-alkenyl, —($C_2$-$C_{10}$)-alkinyl, —($C_6$-$C_{22}$)-aryl, a protecting group and a reporter group, r and s are independently of each other an integer of from 1 to 18, D is the position of attachment of the group to the rest of the nucleic acid binding compound, said alkyl, alkenyl and alkynyl being unsubstituted or substituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—(CH$_2$)$_r$]$_s$—$NR^5R^6$ with the proviso that, if the heterocyclic group of the general formula I is 8-aza-7-deazaadenine (A*) which is attached to a 2' deoxy β-D-erythropentofuranosyl moiety the sequence of said nucleic acid binding compound is not selected from the group consisting of (A*T)$_6$ (SEQ ID NO: 22), CTGGA*TCCAG (SEQ ID NO: 23) or CTGGATCCA*G (SEQ ID NO: 24), if the heterocyclic group of the general formula I is $N^6$-methylated-8-aza-7-deazaadenine (A*$^m$) which is attached to a 2'-deoxy-β-D-erythropentofuranosyl moiety the sequence of said nucleic acid binding compound is not selected from the group consisting of (A*$^m$T)$_6$(SEQ ID NO: 25), CTGGA*$^m$TCCAG (SEQ ID NO: 26) or CTGGATCCA*$^m$G (SEQ ID NO: 27), if the heterocyclic group of the formula I is 8-aza-7-deazadenine which is $N^8$-attached to a β-D-ribofuranosyl moiety the sequence of said compound contains at least one further heterocycle other than adenine and other than 8-aza-7-deazaadenine, and if the heterocyclic group of the general formula I is 8-aza-9-deaza-9-methyl-guanin which is $N^8$-attached to 2'-deoxy-β-D-ribofuranosyl moiety the sequence of said compound contains at least one further heterocycle other than thymidine and other than 8-aza-9-deaza-9-methyl-guanin.

The heterocyclic groups of formula I are mainly characterized by the following properties:

The base is linked to the backbone, preferred to a sugar moiety, via the 8-position (purine numbering).

The base contains an aromatic or quinoide π-electron system which is capable to form stacking interactions with other nucleic acid constituents.

The base contains one or more donor and/or acceptor site(s) for hydrogen bonding to the four natural nucleosides A, C, G and T.

Figure 5:
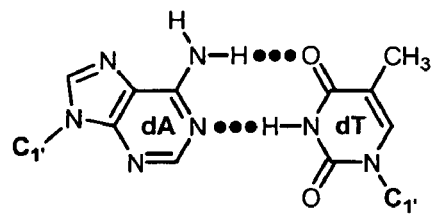
FIG. 5 shows possible duplex structures formed by dA* paired with natural nucleobases.
Figure 5:
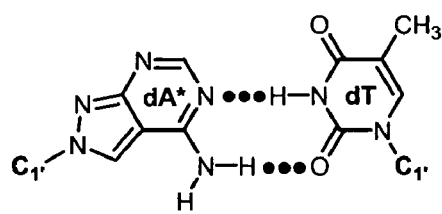
Figure 5:
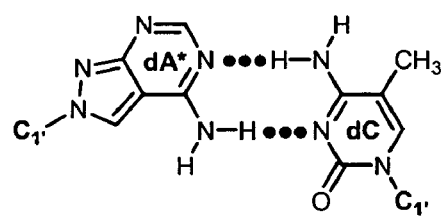
Figure 5:
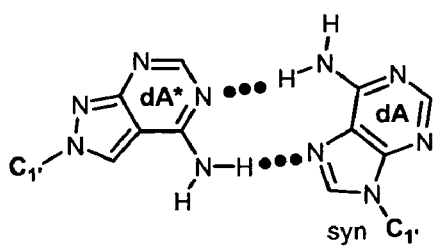
Figure 5:
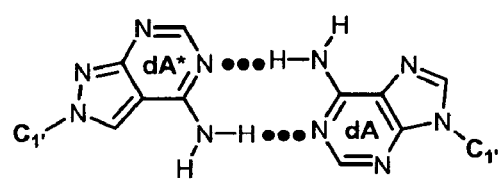
Figure 5:
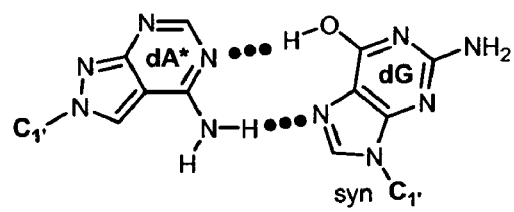

Heterocyclic groups of formula I are linked at the 8-position to the backbone of a nucleic acid binding compound. They are differently located in a double strand complex compared with normal 9-linked purines when hybridized with other nucleic acids. A (naturally) 9-linked guanine or adenine only basepair with its complement base e.g. cytosine and thymine respectively. Whereas, surprisingly 8-linked heterocyclic groups according to the present invention contained in a nucleic acid binding compound show a reduced specificity and allow base pairing via H-bonds with all four natural bases (A, C, G, T) contained in the opposite position of a nucleic acid when hybridized to said nucleic acid binding compound in a double strand complex. As an example possible structures of 8-aza-7-deazaadenine with all four natural bases in a duplex are shown in FIG. 5.

Especially preferred are heterocyclic groups of formula I having an H-donor group (for example an amino-group) linked at position 6 (purine numbering), which not only allows the basepairing of such nucleosides with all four natural bases, but alsopairs with all four natural bases with nearly the same stability. In these compounds $X_3$ is CR3, preferred C—$R^3$ is C—$NR^5R^6$ and most preferred C—$NH_2$. Nucleic acid binding compounds containing these nucleobases at a certain position show the same or an even lower Tm difference when hybridized to different oligonucleotides having A, C, G, or T at the opposite position compared with inosine-containing nucleic acid binding compounds (see example 6).

Also preferred are heterocyclic groups of formula I wherein $X_5$ is N, which allows an $N^8$-glycosylation of these heterocyclic groups.

Therefore heterocyclic groups of formula I can be used as substitutes for natural nucleobases in nucleic acid binding compounds with improved properties. Such nucleic acid binding compounds, as oligonucleotides, can be used for example in hybridization methods when the sequence of a target nucleic acid sequence was deduced from the amino acid sequence of a protein, which led to a variety of possible target nucleic acid sequences. Replacing natural nucleobases by nucleobases according to the present invention at positions so that it hybridizes with positions of target nucleic acids which are degenerated allows the determination of these target nucleic acids without the need of multiple hybridization probes. Another example for an advantageous use is the determination of nucleic acids when allelic sequences containing a different sequence at certain positions are to be determined. Using universal bases according to the invention like the unusually linked 8-aza-7-deazaadenine instead of a natural nucleoside only one probe is sufficient for hybridization. Furthermore, nucleosides like 8-aza-7-deazaadenine can be used as a substitute for each of the four natural bases contained in an oligonucleotide in order to change the Tm of the resulting hybridization complex when hybridized to a nucleic acid. This change in the Tm compared to the Tm of the former probe—nucleic acid complex can be used to equalize the Tm of several hybridization complexes when conducting multiplex hybridization methods like PCR-, multiplex-PCR, multiplex-probe-hybridization-methods or other hybridization techniques performed in solution and/or on a surface. These compounds containing universal bases can also be used in in-vitro-mutagenesis method and as pharmaceuticals. These examples are intended to illustrate possible applications and should not limit the scope of the invention.

With respect to the ring system the heterocyclic groups of formula I according to the present invention are shown in FIG. 7 (heterocycles are shown schematically, substituents are not further described, but are intended to be chosen in formula I)). Also included in the present invention are tautomeric forms and salts of heterocyclic groups of Formula I.

The localization of the double bonds contained in the heterocyclic groups according to formula I depends on the position of the C and N-atoms in the ring system. Therefore, dependent on the choice of $X_1$ to $X_6$ the double bonds are differently situated to allow a planar aromatic or chinoidic π-electron system. The positions of the double bonds are indicated in formula I in a very general way, but it is obvious to a man skilled in the art to indicate them for concrete heterocycles (see also FIG. 7).

Halogen means a fluoro, chloro, bromo or iodo group. The most preferred halogen groups are —Cl and —Br.

Alkyl groups are preferably chosen from alkyl groups containing from 1 to 10 carbon atoms, either arranged in linear, branched or cyclic form. The actual length of the alkyl group will depend on the steric situation at the specific position where the alkyl group is located. If there are steric constraints, the alkyl group will generally be smaller, the methyl and ethyl group being most preferred. All alkyl, alkenyl and alkynyl groups can be either unsubstituted or substituted. Substitution by hetero atoms as outlined above, will help to increase solubility in aqueous solutions.

Alkenyl groups are preferably selected from alkenyl groups containing from 2 to 10 carbon atoms. For the selections similar considerations apply as for alkyl groups. They also can be linear, branched and cyclic. The most preferred alkenyl group is the ethylene group.

Alkynyl groups have preferably from 2 to 10 carbon atoms. Again, those carbon atoms can be arranged in linear, branched and cyclic manner. Further, there can be more than one triple bond in the alkynyl group. The most preferred alkynyl group is the 3-propargyl-group.

Alkoxy groups preferably contain from 1 to 6 carbon atoms and are attached to the rest of the moiety via the oxygen atom. For the alkyl group contained in the alkoxy groups, the same considerations apply as for alkyl groups. The most preferred alkoxy group is the methoxy group.

Aryloxy groups preferably contain from 6 to 20 carbon atoms. Those carbon atoms may be contained in one or more aromatic rings and further in side chains (for example, alkyl chains) attached to the aromatic moiety. Preferred aryloxy groups are the phenoxy and the benzoxy group.

Preferred O-protecting groups are the aroyl groups, the diphenylcarbamoyl group, the acyl groups and the silyl groups. Among these most preferred is the benzoyl group.

Preferred silyl groups are the trialkylsilyl groups, like, trimethylsilyl, triethylsilyl and tertiary butyl-dimethyl-silyl. Another preferred silyl group is the trimethylsilyl-oxy-methyl group (TOM)(Swiss Patent Application 01931/97).

Any atom in the definitions within the formulae presented herein is not limited to a specific isotope. Thus, a phosphorous atom (P) can either mean the regular $^{31}P$ or the radioactive $^{32}P$ or a mixture thereof. The same applies for hydrogen (H/D/T), carbon (C), iodine (Cl, Br, I) and nitrogen (N).

Preferred group —NR$^5$R$^6$ in the definition of R$^1$, R$^2$, R$^3$, R$^4$, R$^{34}$ and R$^{35}$ is the —NH$_2$ group. In this case, it is evident that during chemical synthesis of compounds containing such group of formula I one of the hydrogen atoms of this amino group might be protected by suitable amino protecting group. Such protecting groups are generally known to a man skilled in the art.

During chemical synthesis, any groups —OH, —SH and —NH$_2$ (including those groups in reporter groups) should be protected by suitable protecting groups. Further, during chemical synthesis, the compound will be attached for convenience to a solid phase. In these cases, the definitions of the substituents given above will be selected accordingly.

A protecting group is a chemical group that is attached to a functional moiety (for example to the oxygen in a hydroxyl group or the nitrogen in an amino group, replacing the hydrogen) to protect the functional group from reacting in an undesired way. A protecting group is further defined by the fact that it can be removed without destroying the biological activity of the molecule formed, here the binding of the nucleic acid binding compound to a nucleic acid. Suitable protecting groups are known to a man skilled in the art. Especially preferred protecting groups for example for hydroxyl groups at the 5'-end of a nucleotide or oligonucleotide are selected from the trityl groups, for example dimethoxytrityl.

Preferred protecting groups at exocyclic amino groups in formula I are the acyl groups, most preferred the benzoyl group (Bz), phenoxyacetyl or acetyl or formyl, and the N,N-dialkylformamidine group, preferentially the dimethyl-, diisobutyl-, and the di-n-butylformamidine group.

Figure 8:
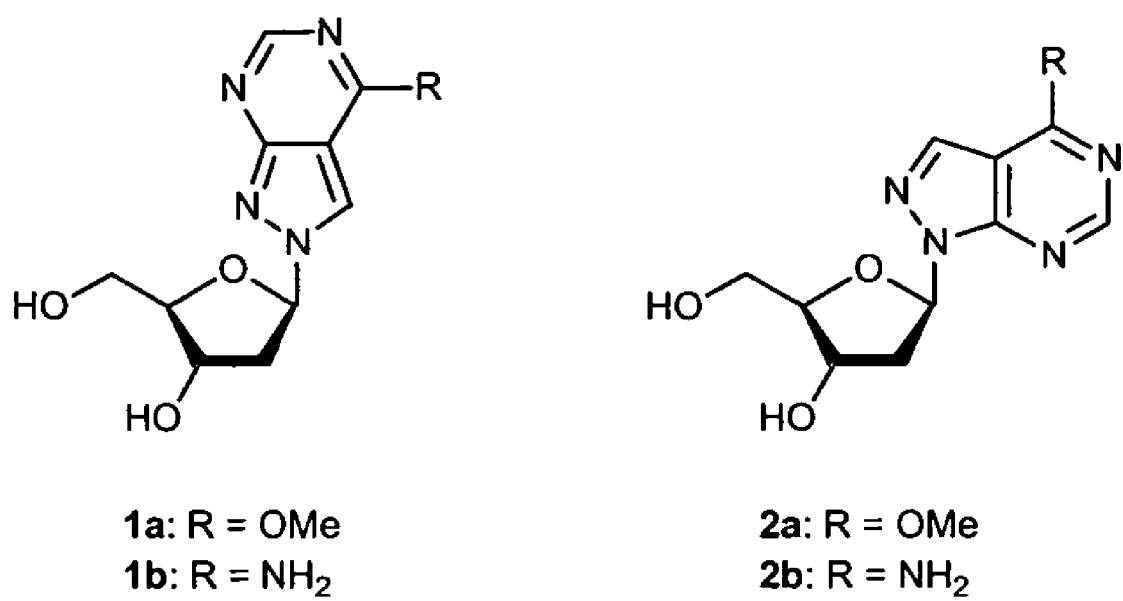
FIG. 8 shows pyrazolo[3,4-d] pyrimidines, a) methoxy-group, b) amino-group.

A simplified protocol for the synthesis of certain nucleosides is described in FIG. 8 and Example 8. In general, for synthesis of a pyrazolo[3,4-d]pyrimidine containing a 6-amino group in a first step the 6-methoxy pyrazolo[3,4-d]pyrimidine is synthesized. In the next step the methoxy-group is exchanged by an amino-group, which has to be coupled to a protecting group to protect the amino-function for example when using the pyrazolo[3,4-d]pyrimidine phosphoramidite for an oligonucleotide synthesis. Surprisingly, the 6-methoxy group of the pyrazolo[3,4-d]pyrimidines 1a and 2a (FIG. 8) can be converted into an amino function under conditions normally used for deprotection in the last step of an oligonucleotide synthesis. Furthermore, the stability of the 6-methoxy-group allows further synthesis steps necessary to synthesize nucleoside monomers, which can be used for oligonucleotide synthesis, for example phosphoramidite monomers. Therefore, it is not necessary to introduce a protected amino-function during synthesis of the nucleoside, but to use the 6-methoxy pyrazolo[3,4-d]pyrimidine monomer when synthesizing the oligonucleotide and exchanging the methoxy group by an amino group when deprotecting the oligonucleotide. This process can also be used for synthesis of related nucleosides having a 6-amino group.

The nucleic acid binding compound according to the invention preferably has a length of less than 100 subunits, more preferably of from 10 to 30 subunits. In order to be active as nucleic acid binding compound, the substituents should be chosen such that hydrogen bonds to heterocyclic groups at the nucleic acid to be bound are enabled, preferably by base pairing, for example by Watson-Crick or Hoogsteen base pairing. Compounds in which the substituents do not enable such preferred hydrogen bonding, can be useful as intermediates for the preparation of nucleic acid binding compounds. Preferred nucleic acid binding compounds of the invention are those which are chemically synthesized.

If the nucleic acid binding compound is to be used as a probe for the determination of a nucleic acid, or any other identification of the compound or the nucleic acid is intended, any of the substituents are selected such as to contain a reporter group. While as many reporter groups can be attached as useful to label the nucleic acid compound sufficiently, it is preferred to attach only a limited number of reporter groups to a single subunit, such that recognition of nucleic acids, affinities to nucleic acids and solubility is not affected such that the probe would not be useful in hybridization assays. In a very preferred case, there will be only from 1 to 4, most preferably 1 or 2 or most preferred only one reporter group in each nucleic acid binding compound. There are formats for the nucleic acid determination which require more than one reporter group attached to the probe. An example for such formats is disclosed in WO92/02638. In this case, one of the reporter groups will be a fluorescence emitter, while the other is a fluorescence quencher.

Reporter groups are generally groups that make the nucleic acid binding compound as well as any nucleic acids bound thereto distinguishable from the remainder of the liquid, i.e. the sample (nucleic acid binding compounds having attached a reporter group can also be termed labeled nucleic acid binding compounds, labeled probes or just probes). This distinction can be either effected by selecting the reporter group from the group of directly or indirectly detectable groups or from the groups of immobilized or immobilizable groups. Directly detectable groups are for example fluorescent compounds, like fluorescein and its derivatives, like hexachlorofluorescein and hexafluorofluorescein, rhodamines, psoralenes, squaraines, porphyrines, fluorescent particles, bioluminescent compounds, like acridinium esters and luminol, or the cyanine dyes, like Cy-5. Examples of such compounds are disclosed in EP 0 680 969. Further, spin labels like TEMPO, electrochemically detectably groups, ferrocene, viologene, heavy metal chelates and electrochemiluminescent labels, like ruthenium bispyridyl complexes, and naphthoquinones, quencherdyes, like dabcyl, and nuclease active complexes, for example of Fe and Cu, are useful detectable groups. Other examples of such compounds are europium complexes. Indirectly detectable groups are groups that can be recognized by another moiety which is directly or indirectly labelled. Examples of such indirect detectable groups are haptens, like digoxigenin or biotin. Digoxigenin for example can be recognized by antibodies against digoxigenin. Those antibodies may either be labelled directly or can be recognized by labelled antibodies directed against the (anti-digoxigenin) antibodies. Formats based on the recognition of digoxigenin are disclosed in EP-B-0 324 474. Biotin can be recognized by avidin and similar compounds, like streptavidin and other biotin binding compounds. Again, those compounds can be labelled directly or indirectly.

The reporter group can further be a nucleotide sequence which does not interfere with other nucleotide sequences in the sample. The sequence can therefore be specifically recognized by nucleotide containing a complementary sequence. This nucleotide sequence can be labelled directly or indirectly or can be immobilizable or immobilized.

A reporter group can further be a solid phase. Attachment of the nucleic acid binding compound with solid phase can be either directly or indirectly as pointed out above for the detectable group. Examples of such solid phases are latex beads or gold particles.

Direct labelling can be effected by covalent coupling of a nucleic acid binding compound to a reactive group on the solid phase, i.e. preferably via a linker. Indirect labelling can be made similar as disclosed above for the detectable groups. Preferably, indirect attachment is non-covalently by biospecific interactions, for example those selected from the group of hapten-antibody, vitamin-receptor and nucleic acid-complementary nucleic acid. Again, those interactions and their use in nucleic acid assays is known to a man skilled in the art.

Solid phases that are useful for immobilization of the probe according to the invention are preferably selected from the group of polystyrene, polyethylene, polypropylene, glass and $TiO_2$. The formats of such solid phases can be selected according to the needs of the instrumentation and format of the assay. For example, a solid phase may assume the form of a bead or a vessel.

The term reporter group and the specific embodiments preferably include a linker which is used to connect the moiety intended to be used (the actual solid phase or the fluorophoric moiety) to the position of attachment as the reporter group. The linker will provide flexibility such that the nucleic acid binding compound can bind the nucleic acid sequence to be determined without major hindrance by the solid phase. Linkers, especially those that are not hydrophobic, for example based on consecutive ethylenoxy units, for example as disclosed in DE 3943522 are known to a man skilled in the art.

From the above explanation, it becomes clear that the invention would still work, even if the backbone of the probe is not an oligonucleotide in the strict sense. There were described in the last years nucleic binding compounds that have similar properties like oligonucleotides, but differ in their backbone. The backbone is generally considered to be the part of the nucleic acid binding compound that bears the bases, mostly in linear manner, bound to identical or not identical subunits. The most popular backbone is the naturally occurring sugar phosphate backbone of nucleic acids (containing either ribonucleoside subunits (RNA), deoxyribonucleoside subunits (DNA) or peptide nucleic acid subunits (PNA)). Therefore, in a preferred embodiment, the backbone comprises sugar and phosphate moieties. In a further preferred embodiment, the sugar configuration is selected from the group consisting of the α-D-, β-D-, α-L- and β-L-configurations, most preferred the compound contains at least one 2'-deoxy-β-D-erythro-pentofuranosyl moiety or one β-D-ribofuranosyl moiety.

Preferred aryl group is the phenyl or naphthyl moiety, either unsubstituted or substituted by one or more of amino, -aminoalkyl, —O—$(C_1-C_{10})$-alkyl, —S—$(C_1-C_{10})$-alkyl, —$(C_1-C_{10})$-alkyl, sulfonyl, sulfenyl, sulfinyl, nitro and nitroso. Most preferred aryl group is the phenyl group. Preferred arylalkyl group is the benzyl group. The preferred alkylamino group is the ethylamino group. The preferred —COO$(C_1-C_4)$ alkyl group contains one or two carbon atoms in the alkyl moiety (methyl or ethyl esters).

Preferred, D is the glycosid C-1 of a sugar moiety of the compound according to the invention.

The nucleic acid binding compound will be constructed such that it contains a nucleobase sequence which is substantially complementary to the nucleic acid to be determined or the nucleic acid to which it is intended to be bound by base pairing. As those nucleic acids will usually contain at least once any of the naturally occurring nucleobases Ade, Cyt, Gua and Thy or Ura, the nucleic acid binding compound according to the invention will also contain any of those four bases. However, acccording to the invention, at least one of the heterocyclic groups is replaced by the heterocyclic base of formula I.

The nucleic acid binding compound according to the invention will bind to nucleic acids preferably in the antiparallel mode. However, by carefully selecting the nucleobases of a nucleic acid and/or of the nucleic binding compound, the binding in its function as probe can also be forced to be in the parallel mode. Parallel hybridization of nucleic acids containing iso-C and iso-G is for example disclosed in EP 0 624 161.

Preferred nucleic acid binding compounds are those, wherein the backbone comprises one or more moieties of the general formula II

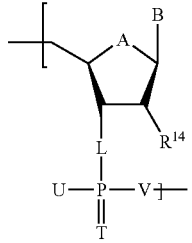

Formula II wherein
A is selected from the group consisting of O, S, $CH_2$ and N—$(C_1-C_{10})$-alkyl,
L is selected from the group consisting of oxy, sulfanediyl, —$CH_2$— and —$NR^{22}$—,
T is selected from the group consisting of oxo, thioxo and selenoxo,
U is selected from the group consisting of —OH, —O-reporter group, —SH, —S reporter group —SeH, —$(C_1-C_{10})$-alkoxy, —$(C_1-C_{10})$-alkyl, —$(C_6-C_{22})$-aryl, —$(C_6-C_{14})$-aryl-$(C_1-C_{10})$-alkyl, —$NR^{23}R^{24}$, and —O—$(C_1-C_{10})$-alkyl-O—$(C_1-C_{10})$-alkyl-$R^{25}$, or wherein —$NR^{23}R^{24}$ can together with N be a 5-6-membered heterocyclic ring,
V is selected from the group consisting of oxy, sulfanediyl, —$CH_2$— and —$NR^{22}$—,
$R^{14}$ is selected from the group consisting of —H, —OH, —$(C_1-C_{10})$-alkoxy, —$(C_2-C_{10})$-alkenyloxy, -halogen, -azido, —O-allyl, —O-alkinyl, and —$NH_2$,
$R^{22}$ is independently selected from the group of —H and —$(C_1-C_{10})$-alkyl,
$R^{23}$ and $R^{24}$ are independently selected from the group consisting of —$(C_1-C_{10})$-alkyl, —$(C_1-C_{20})$-aryl, —$(C_6-C_{14})$-aryl-$(C_1-C_{10})$-alkyl, —$(C_1-C_6)$-alkyl-[NH($CH_2$)$_c$]$_d$—$NR^{26}R^{27}$ and a reporter group,
$R^{25}$ is selected from the group consisting of —H, —OH, -halogen, -amino, —$(C_1-C_{18})$-alkylamino, —COOH, —$CONH_2$ and —COO$(C_1-C_4)$-alkyl and a reporter group,
$R^{26}$ and $R^{27}$ are independently selected from the group consisting from —H, —$(C_1-C_6)$-alkyl, and —$(C_1-C_4)$-alkoxy-$(C_1-C_6)$-alkyl and a reporter group,
c is an integer from 2 to 6,
d is an integer from 0 to 6, and
B is a moiety of formula I (as defined above),
wherein any alkyl, alkenyl and alkynyl can be substituted or unsubstituted by one or more moieties selected from the group consisting of -halogen, —SH, —S—$(C_1-C_6)$-alkyl, —$(C_1-C_6)$-alkoxy, —OH, —$NR^5R^6$, —$COR^{11}$, —NH—$CONR^5R^6$, —NH—$CSNR^5R^6$ and —[O—$(CH_2)_r$]$_s$—$NR^5R^6$,
r and s are independently of each other an integer of 1 to 18, and any salts thereof.

The preferred definitions of the groups as defined under formula I apply to formula II and the following formulae, if not indicated otherwise.

Preferably, in compounds of formula II, $R^{14}$ is hydrogen. Preferred definition of L is oxy. Preferred definition of U is —OH and —O-reporter group. Preferred definition of V is oxy. Preferred definition of c is an integer from 2 to 4, and of d an integer from 0 to 2.

Compounds of formula II are especially suited to contain the heterocyclic moiety of the invention as an integrated part (preferably not at one of the termini) of the nucleic acid binding compound.

The group $NR^{23}R^{24}$ is preferably selected from the group consisting of dialkylamino groups. In case of this group together with the forming of 5- or 6-membered heterocyclic ring, it assumes preferably the definition of morpholinyl, pyrrolidinyl or piperidinyl.

A preferred subject of the invention is therefore a nucleic acid binding compound as outlined above, wherein the backbone comprises one or more moieties of the general formula III

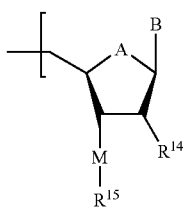

Formula III wherein

A is selected from the group consisting of O, S, $CH_2$ and N—$(C_1$-$C_6)$-alkyl, M is selected from the group consisting of oxy, sulfanediyl, —$NR^{22}$—, —$(C_1$-$C_{10})$-alkyl-, or —O—$(C_1$-$C_{10})$-alkyl-O—, and —S—$(C_1$-$C_{10})$-alkyl-O— and —$NR^{22}$—$(C_1$-$C_6)$-alkyl-O—, $R^{22}$ is selected from the group of —H, —$(C_1$-$C_{10})$-alkyl, a protecting group and a reporter group, $R^{14}$ is selected from the group consisting of —H, —OH, —$(C_1$-$C_{10})$-alkoxy, —$(C_2$-$C_{10})$-alkenyloxy, —$(C_2$-$C_{10})$-alkynyloxy, -halogen, -azido, SH, —$(C_1$-$C_{10})$-alkylmercapto, O-reporter group and —$NH_2$, $R^{15}$ is selected from the group consisting of —H, —$(C_1$-$C_6)$-alkyl, —$(C_2$-$C_{10})$-alkenyl, —$(C_2$-$C_{10})$-alkynyl, —$(C_2$-$C_{10})$-alkyl-carbonyl, —$(C_3$-$C_{19})$-alkenyl-carbonyl, —$(C_3$-$C_{19})$-alkynyl-carbonyl, —$(C_6$-$C_{14})$-aryl-$(C_1$-$C_{10})$-alkyl, a solid phase and a group of formula IV

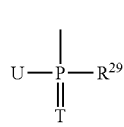

Formula IV wherein

T is selected from the group consisting of oxo, thioxo and selenoxo, and

U is selected from the group consisting of —OH, —O-reporter group, —SH, —SeH, —$(C_1$-$C_{10})$-alkoxy, —$(C_1$-$C_{10})$-alkyl, —$(C_6$-$C_{22})$-aryl, —$(C_6$-$C_{14})$-aryl-$(C_1$-$C_{10})$-alkyl, —$NR^{23}R^{24}$, and —O—$(C_1$-$C_{10})$-alkyl-O—$(C_1$-$C_{10})$-alkyl-$R^{25}$, or wherein $NR^{23}R^{24}$ can together with N be a 5-6-membered heterocyclic ring, $R^{23}$ and $R^{24}$ are independently selected from the group consisting of —$(C_1$-$C_{10})$-alkyl, —$(C_1$-$C_{20})$-aryl, —$(C_6$-$C_{14})$-aryl-$(C_1$-$C_{10})$-alkyl, —$(C_1$-$C_6)$-alkyl-[NH$(CH_2)_c]_d$—$NR^{26}R^{27}$, $R^{25}$ is selected from the group consisting of —H, —OH, -halogen, -amino, —$(C_1$-$C_{18})$-alkylamino, —COOH, —$CONH_2$ and —COO$(C_1$-$C_4)$-alkyl, $R^{26}$ and $R^{27}$ are independently selected from the group consisting from —H, —$(C_1$-$C_6)$-alkyl, and —$(C_1$-$C_4)$-alkoxy-$(C_1$-$C_6)$-alkyl $R^{29}$ is selected from the group consisting of —$OR^{30}$ and —$SR^{30}$, $R^{30}$ is selected from the group consisting of —H, —$(C_1$-$C_{10})$-alkyl, —$(C_2$-$C_{10})$-alkenyl, —$(C_6$-$C_{22})$-aryl, a protecting group, a solid phase and a reporter group B is the link to a moiety of formula I (as defined above), and any salts thereof.

For the definitions and preferences the particulars apply as outlined for the substituents under formulae I and II, if not specified otherwise specifically for formula III.

Nucleic acid binding compounds, wherein the group of formula I is attached to subunits, for example the nucleotide, at the 3'-terminus of the compound, are useful either as starting compound for the synthesis of longer compounds or/and as end-labeled probes. This group of compounds is especially preferred because the terminal position of probes generally is the most tolerant in view of attachment of chemical moieties.

A further preferred subject of the invention is a nucleic acid binding compound as outlined above comprising a backbone moiety of the formula V

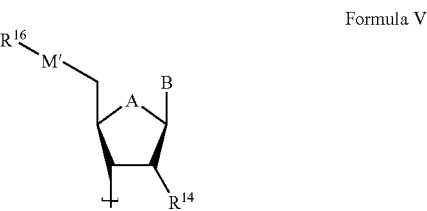

Formula V wherein

A is selected from the group consisting of O, S, $CH_2$ and N—$(C_1$-$C_6)$-alkyl, M' is selected from the group consisting of oxy, sulfanediyl, —$NR^{22}$—, —$(C_1$-$C_{10})$-alkyl, or —O—$(C_1$-$C_{10})$-alkyl-O—, and —S—$(C_1$-$C_{10})$-alkyl-O— and —$NR^{22}$—$(C_1$-$C_6)$-alkyl-O—, $R^{22}$ is selected from the group of —H, a protecting group, a reporter group and —$(C_1$-$C_{10})$-alkyl, $R^{14}$ is selected from the group consisting of —H, —OH, —$(C_1$-$C_{10})$-alkoxy, —$(C_2$-$C_{10})$-alkenyloxy, —$(C_2$-$C_{10})$-alkynyloxy, -halogen, azido, —SH, —S—$(C_1$-$C_6)$-alkylmercapto, O-reporter group, O-solid phase and $NH_2$, $R^{16}$ is selected from the group consisting of —H, —$(C_1$-$C_8)$-alkyl, —$(C_2$-$C_{18})$-alkenyl, —$(C_2$-$C_{18})$-alkynyl, —$(C_2$-$C_{18})$-alkyl-carbonyl, —$(C_3$-$C_{19})$-alkenyl-carbonyl, —$(C_3$-$C_{19})$-alkynyl-arbonyl, —$(C_6$-$C_{14})$-aryl-$(C_1$-$C_8)$-alkyl, a protective group or a compound of formula IV

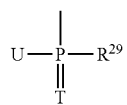

Formula IV wherein

T is selected from the group consisting of oxo, thioxo and selenoxo,

U is selected from the group consisting of —OH, —SH, —SeH, —($C_1$-$C_{10}$)-alkoxy, —($C_1$-$C_{10}$)-alkyl, —($C_6$-$C_{22}$)-aryl, —($C_6$-$C_{14}$)-aryl-($C_1$-$C_{10}$)-alkyl, —$NR^{23}R^{24}$, and —O—($C_1$-$C_{10}$)-alkyl-O—($C_1$-$C_{10}$)-alkyl-$R^{25}$, wherein $NR^{23}R^{24}$ can together with N be a 5-6-membered heterocyclic ring, $R^{23}$ and $R^{24}$ are independently selected from the group consisting of —($C_1$-$C_{10}$)-alkyl, —($C_1$-$C_{20}$)-aryl, —($C_6$-$C_{14}$)-aryl-($C_1$-$C_{10}$)-alkyl, —($C_1$-$C_6$)-alkyl-[NH($CH_2$)$_c$]$_d$—$NR^{26}R^{27}$, $R^{25}$ is selected from the group consisting of —H, —OH, -halogen, -amino, —($C_1$-$C_{18}$)-alkylamino, —COOH, —$CONH_2$ and —COO($C_1$-$C_4$)-alkyl, $R^{26}$ and $R^{27}$ are independently selected from the group consisting from —H, —($C_1$-$C_6$)-alkyl, and —($C_1$-$C_4$)-alkoxy-($C_1$-$C_6$)-alkyl $R^{29}$ is selected from the group consisting of —$OR^{30}$ and —$SR^{30}$, $R^{30}$ is selected from the group consisting of —H, —($C_1$-$C_{10}$)-alkyl, —($C_2$-$C_{10}$)-alkenyl, —($C_6$-$C_{22}$)-aryl, a protecting group, a solid phase and a reporter group, and B is the link to a moiety of formula I (as defined above), wherein any alkyl, alkenyl and alkynyl can be substituted or unsubstituted, by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—($CH_2$)$_r$]$_s$—$NR^5R^6$, and any salts thereof.

A very preferred compound is a compound of formula V, wherein M' is O, $R^{16}$ is H and $R^{14}$ is selected from the group consisting of hydrogen and hydroxyl.

Those compounds can for example be used as 5'-terminally labeled probes. Regarding the definitions of the substituents, the definitions as given above apply if not indicated otherwise.

The backbone of the nucleic acid binding compound has the function to bear the base pairing heterocycles such that the compound can bind to a nucleic acid having a complementary sequence. Preferably, the degree of complementarity in the naturally occurring bases will be in the range from 70% up to 100% in a stretch of bases in a region effecting binding, compared to the stretch of same length in the region of the nucleic acid to be bound. Deletions and insertions of subunits in each sequence will therefor, in this calculation, be counted as gaps until the next fitting base and thus reduce complementarity by as many bases as the gap contains.

Preferred backbone contains sugar-phosphate moieties. From these, deoxy sugar containing backbones are further preferred.

Each moiety in the backbone bearing a moiety capable of base pairing to a nucleic acid of complementary sequence, including the moieties of the invention, are termed a subunit. Compounds are known that have backbones mixed of different kinds of subunits. Recently, a new kind of non-natural nucleic acid binding compounds was described. They are termed Peptide Nucleic Acids (PNA), as they contain at least one peptide bond between the subunits (WO 92/20702). The nucleic acid binding compound of the present invention can have any length. However, due to the convenience of chemical synthesis, compounds of a length of less than 100, more preferably from 10 to 30 subunits, for example nucleosides, are preferred.

The nucleic acid binding compound of the present invention can be prepared in solution or, preferably, on a solid phase, where appropriate using an automatic synthesis device. The oligomers can be assembled stepwise by successively condensing a mononucleotide, which in each case possesses a nucleotide base, onto an appropriately derivatized support or onto a growing oligomer chain. Alternatively, the nucleic acid binding compounds can be assembled by joining dinucleotides or trinucleotides together [S. Beaucage et al., Tetrahedron, 48 (12), 2223-2311, (1992); and Tetrahedron, 48 (28), 6123-6194, (1993)]. This is particularly advantageous when synthesizing oligonucleotides which posses modified phosphate bridges.

The oligonucleotides are assembled using methods which are known to the person skilled in the art, such as the triester method, the H-phosphonate method or the phosphoramidite method [E. Sonveaux, (1986), Bioorganic Chemistry, 14, 274-325; S. L. Beaucage et al., (1992), Tetrahedron, 48, 2223-2311].

A further subject of the invention is therefore a method for the chemical synthesis of nucleic acid binding compounds of the present invention using activated subunits, wherein said subunit contains at least one group of formula I. The most preferred method of chemical synthesis uses the phosphoramidite approach. A particularly preferred method uses a activated subunit one or more compounds of general formula VII. This method has the advantage that it is very convenient and the reagents necessary, for example a phosphoramidite containing a group of formula I, are possible to be included easily.

A further subject of the invention are therefore compounds of the general formula VII

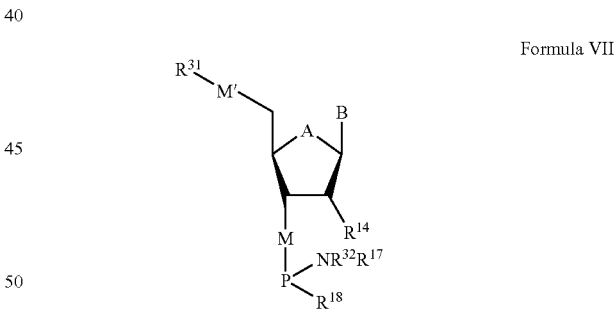

Formula VII wherein

A is selected from the group consisting of O, S, $CH_2$ and N—($C_1$-$C_6$)-alkyl, M and M' are independently selected from the group consisting of oxy, sulfanediyl, —$NR^{22}$, —($C_1$-$C_{10}$)-alkyl, or —O—($C_1$-$C_{10}$)-alkyl-O—, and —S—($C_1$-$C_{10}$)-alkyl-O— and —$NR^{22}$—($C_1$-$C_6$)-alkyl-O—, $R^{22}$ is selected from the group of —H and —($C_1$-$C_{10}$)-alkyl, $R^{14}$ is selected from the group consisting of —H, —$OR^{31}$, —($C_1$-$C_{10}$)-alkoxy, —($C_2$-$C_{10}$)-alkenyloxy, —($C_2$-$C_{10}$)-alkynyloxy, -halogen, -azido $NHR^{31}$, $SR^{31}$, O-reporter group and —$NH_2$, $R^{31}$ is a protecting group or a reporter group, $R^{32}$ and $R^{17}$ are independently selected from the group consisting of —H, —($C_1$-$C_{10}$)-alkyl, —($C_2$-$C_{10}$)-alkenyl, —($C_6$-$C_{22}$)-aryl, or wherein $NR^{32}R^{17}$ can together with N be a 5-6-membered heterocyclic ring $R^{18}$ is selected from the group consisting of —($C_2$-$C_6$)-alkenyloxy, substituted or unsubstituted —($C_1$-$C_6$)-alkyl, unsubstituted —($C_1$-$C_6$)-alkoxy or —($C_1$-$C_6$)-alkoxy substituted one or more times by a group selected from the group consisting of -halogen, p-nitroaryloxy and -cyano, and B is a group of formula I (as defined above)

said alkyl, alkenyl and alkynyl being unsubstituted or substituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—($CH_2$)$_r$]$_s$—$NR^5R^6$, r and s are independently of each other an integer of from 1 to 18, with the proviso that said compound is not 2-[2'-deoxy-5'-O-(4,4'-dimethoxytrityl)-β-erythro-pentofuranosyl]-4-(methylamino)-1H-pyrazolo[3,4-d]-pyrimidine 3'-[methyl N,N-diisopropylphosphoramidite], 4-(benzoylamino)-2-[2'-deoxy-5'-O-(dimethoxytrityl)-β-D-erythro-pentofuranosyl]-2H-pyrazolo[3,4-d]-pyrimidine 3'-[methyl N,N-diisopropylphosphoramidite] or N-[2-[5-O-[Bis(4-methoxyphenyl)phenylmethyl]-2'-deoxy-β-D-ribofuranosyl]-3-methyl-7-oxo-2H-pyrazolo[4,3-d]pyrimidin-5-yl]-2-methyl-propanamide-3'-[(2-cyanoethyl)N,N-diisopropylphosphoramidite].

Preferred nucleotide monomer structural components of the formula VII are those wherein $X^5$ is N, also preferred are those compounds wherein $X_3$ is $CR_3$, more preferred C—$NR^5R^6$, most preferred C—$NH_2$.

The compounds of the formula VII can be prepared, as structural components for the oligonucleotide solid phase synthesis, by proceeding from the corresponding 8-glycosylated nucleosides. For example, the preparation of the 8-glycosylated derivatives which are substituted at the 7- or 9-position by halogen or methyl can be performed in the case of 7-deazapurine derivative as described by Seela et al. [Helv. Chim. Acta, (1994), 77, 897-903]. Alkenyl- or alkynyl-substituted 8-glycosylated nucleoside derivatives of the formula VII can be prepared by coupling of alkenyl or alkynyl groups into the 7 or 8 position of the six-five-membered ring system by means of cross-coupling reaction in the presence of tetrakis(triphenylphospine)palladium(0).

Electrophilic substituents (for example halogens) can be introduced into the 7 or 9 position of the five-six membered base. These halogenated bases can be glycosylated in acetonitrile with □-halogenose in the presence of KOH and TDA-1 to yield the 8-glycosylated and the 9- or 7-glycosylated derivatives. The halogenated nucleosides can then be used as starting compounds for the insertion of other substituents, for example alky, alkenyl or alkynyl groups, by means of the above described palladium-catalyzed cross-coupling reaction. Alkoxy derivatives or substituted amine derivatives can be introduced by nucleophilic substitution, and nitro groups can be indroduced by electrophilic substitution.

After suitable protective groups for the amino groups at position 6 and for the free 5'-hydroxyl group of the sugar moiety have been introduced, the monomers are converted into the corresponding phosphonate or phosphoramidite derivatives. Suitable amino protective groups, for example in the form of acyl protective groups (e.g. isobutyryl, acetyl or phenoxyacetyl), are inserted using well-known methods [J. C. Schulhof, D. Molko, R. Teoule, (1987), Nucleic Acids Res., 15, 397-416]. An example of a suitable protective group for the free 5'-OH group of the sugar is the 4,4'-dimethoxytrityl residue, whose insertion is likewise effected using known methods [C. B. Reese (1978), Tetrahedron, 34, 3143; D. Flockerzi et al., (1981), Liebigs Ann. Chem., 1568]. The monomers which have been protected in this way can be converted into the corresponding phosphonates in accordance with a protocol due to Froehler et al. [B. C. Froehler et al., (1986), Nucleic Acids Res., 14, 5399]. Cyanoethyl-phosphoramidite derivatives can, for example, be prepared by reacting the monomers with chloro-β-cyanoethoxy-(N,N-diisopropylamino)phosphane in anhydrous dichlormethane [N. D. Sinha et al., (1984), Nucleic Acids Res., 12, 4539].

Further subject of the invention are compounds of the general formula IX

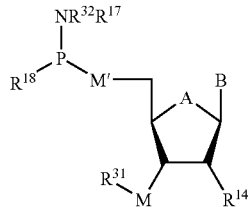

Formula IX wherein

A is selected from the group consisting of O, S, $CH_2$ and N—($C_1$-$C_6$)-alkyl, M and M' are independently selected from the group consisting of oxy, sulfanediyl, —$NR^{22}$, —($C_1$-$C_{10}$)-alkyl, or —O—($C_1$-$C_{10}$)-alkyl-O—, and —S—($C_1$-$C_{10}$)-alkyl-O— and —$NR^{22}$—($C_1$-$C_6$)-alkyl-O—, $R^{22}$ is selected from the group of —H and —($C_1$-$C_{10}$)-alkyl, $R^{14}$ is selected from the group consisting of —H, —$OR^{31}$, —($C_1$-$C_{10}$)-alkoxy, —($C_2$-$C_{10}$)-alkenyloxy, —($C_2$-$C_{10}$)-alkynyloxy, -halogen, -azido $NHR^{31}$, $SR^{31}$, O-reporter group and —$NH_2$, $R^{31}$ is a protecting group or a reporter group, $R^{32}$ and $R^{17}$ are independently selected from the group consisting of —H, —($C_1$-$C_{10}$)-alkyl, —($C_2$-$C_{10}$)-alkenyl, —($C_6$-$C_{22}$)-aryl or wherein $NR^{32}R^{17}$ can form together with N a 5-6-numbered heterocyclic ring, $R^{18}$ is selected from the group consisting of ($C_2$-$C_6$)-alkenyloxy, substituted or unsubstituted —($C_1$-$C_6$)-alkyl, unsubstituted —($C_1$-$C_6$)-alkoxy or —($C_1$-$C_6$)-alkoxy substituted one or more times by a group selected from the group consisting of -halogen, p-nitroaryloxy and -cyano, and B is a group of formula I (as defined above)

Those compounds can be used like those of formula VII in chemical synthesis. A further subject of the invention are compounds of the general formula X

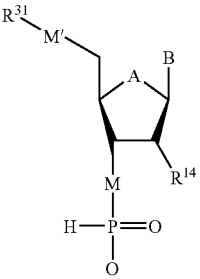

Formula X wherein

M and M' are independently selected from the group consisting of oxy, sulfanediyl, —NR$^{22}$, —($C_1$-$C_{10}$)-alkyl, or —O—($C_1$-$C_{10}$)-alkyl-O—, and —S—($C_1$-$C_{10}$)-alkyl-O— and —NR$^{22}$—($C_1$-$C_6$)-alkyl-O—, R$^{22}$ is selected from the group of —H and —($C_1$-$C_{10}$)-alkyl, R$^{14}$ is selected from the group consisting of —H, —OR$^{31}$, —($C_1$-$C_{10}$)-alkoxy, —($C_2$-$C_{10}$)-alkenyloxy, —($C_2$-$C_{10}$)-alkynyloxy, -halogen, -azido NHR$^{31}$, SR$^{31}$, O-reporter group and —NH$_2$, R$^{31}$ is a protecting group or a reporter group, B is a group of formula I (as defined above).

Those compounds are useful in chemical synthesis of nucleic acid binding compounds as mentioned above and the precursors thereof.

In another option which is more suited for long oligomers and those based on natural backbones, the oligomers are produced enzymatically. In this case, a starting oligomer is reacted with a polymerase and a triphosphate or modified triphosphate such that a monophoshate or a modified monophosphate is attached to a terminus of the oligomer, thus elongating the oligomer. Also for this method, the man skilled in the art will know several possible formates, like the nick-translation approach, or the simple primer extension (J. Sambrook. E. F. Fritsch, T. Maniatis, Molecular Cloning—A laboratory Manual, Cold Spring Harbor Laboratory Press 1989).

A further subject of the invention is therefore a method for the enzymatic synthesis of a nucleic acid binding compound according to the invention comprising reacting a triphosphate subunit with a primer using a nucleic acid as a template for the elongation of the primer, wherein the triphosphate subunit contains a heterocyclic group of formula I. Preferably, the triphosphate subunit has the formula VI.

A further subject of the present invention are therefore compounds of the general formula VI

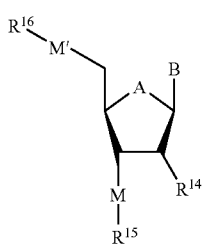

Formula VI wherein

A is selected from the group consisting of O, S, CH$_2$ and N—($C_1$-$C_6$)-alkyl, R$^{14}$ is selected from the group consisting of —H, —OH, —($C_1$-$C_{10}$)-alkoxy, O-protecting group, S-protecting group, NH-protecting group, —($C_2$-$C_{10}$)-alkenyloxy, -halogen, -azido, —SH, —($C_1$-$C_6$)-alkylmercapto, O-reporter group, O-solid phase and —NH$_2$, R$^{15}$ and R$^{16}$ are independently selected from the group consisting of —H, —($C_1$-$C_8$)-alkyl, —($C_2$-$C_{18}$)-alkenyl, —($C_2$-$C_{18}$)-alkynyl, —($C_2$-$C_{18}$)-alkyl-carbonyl, —($C_3$-$C_{19}$)-alkenyl-carbonyl, —($C_3$-$C_{19}$)-alkynyl-carbonyl, —($C_6$-$C_{14}$)-aryl-($C_1$-$C_8$)-alkyl, a protecting group or a compound of formula IV, with the proviso that R$^{15}$ or R$^{16}$ is a group of formula IV,

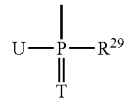

Formula IV wherein

T is selected from the group consisting of oxo, thioxo and selenoxo,

U is selected from the group consisting of —OH, —SH, —SeH, —($C_1$-$C_{10}$)-alkoxy, —($C_{1}$-$C_{10}$)-alkyl, —($C_6$-$C_{22}$)-aryl, —($C_6$-$C_{14}$)-aryl-($C_1$-$C_{10}$)-alkyl, —NR$^{23}$R$^{24}$, and —O—($C_1$-$C_{10}$)-alkyl-O—($C_1$-$C_{10}$)-alkyl-R$^{25}$, or wherein NR$^{23}$R$^{24}$ can together with N be a 5-6-membered heterocyclic ring, R$^{23}$ and R$^{24}$ are independently selected from the group consisting of —($C_1$-$C_{10}$)-alkyl, —($C_1$-$C_{20}$)-aryl, —($C_6$-$C_{14}$)-aryl-($C_1$-$C_{10}$)-alkyl, —($C_1$-$C_6$)-alkyl-[NH(CH$_2$)$_c$]$_d$—NR$^{26}$R$^{27}$, R$^{25}$ is selected from the group consisting of —H, —OH, -halogen, amino, —($C_1$-$C_{18}$)-alkylamino, —COOH, —CONH$_2$ and COO($C_1$-$C_4$)-alkyl, R$^{26}$ and R$^{27}$ are independently selected from the group consisting from —H, —($C_1$-$C_6$)-alkyl, and —($C_1$-$C_4$)-alkoxy-($C_1$-$C_6$)-alkyl, R$^{29}$ is selected from the group consisting of —OR$^{30}$ and —SR$^{30}$, R$^{30}$ is selected from the group consisting of —H, —($C_1$-$C_{10}$)-alkyl, —($C_2$-$C_{10}$)-alkenyl, —($C_6$-$C_{22}$)-aryl, a protecting group, a phosphate, a diphosphate and a reporter group, and M and M' are independently selected from the group consisting of oxy, sulfanediyl, —NR$^{22}$, —($C_1$-$C_{10}$)-alkyl, or —O—($C_1$-$C_{10}$)-alkyl-O—, and —S—($C_1$-$C_{10}$)-alkyl-O— and —NR$^{22}$—($C_1$-$C_6$)-alkyl-O—, R$^{22}$ is selected from the group of —H and —($C_1$-$C_{10}$)-alkyl, and B is a moiety of formula I (as defined above), wherein any alkyl, alkenyl and alkynyl can be substituted or unsubstituted by one or more moieties selected from the group consisting of -halogen, —SH, —S—($C_1$-$C_6$)-alkyl, —($C_1$-$C_6$)-alkoxy, —OH, —NR$^5$R$^6$, —COR$^{11}$, —NH—CONR$^5$R$^6$, —NH—CSNR$^5$R$^6$ and —[O—(CH$_2$)$_r$]$_s$—NR$^5$R$^6$, with the proviso that said compound is not 8-aza-7-deaza-7-H-adenine-N$^8$-β-D-ribofuranosyl-5'-monophosphate or 8-aza-7-deaza-7-H-adenine-N$^8$-β-D-ribofuranosyl-5'-diphosphate.

Most preferred in these compounds -M'R$^{16}$ is a triphosphate group and -MR$^{15}$ is OH. The most preferred compound is the one in which R$^{14}$ is —H.

Most preferred compounds for enzymatic synthesis of a nucleic acid binding compound according to the invention are of formula VIII

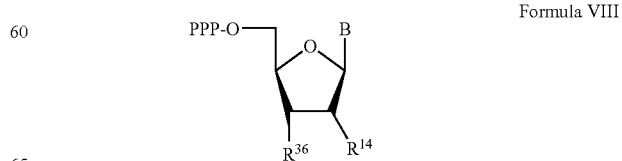

Formula VIII wherein

PPP is a triphosphate group, $R^{14}$ is selected from the group consisting of —H, —OH, —($C_1$-$C_{10}$)-alkoxy, —($C_2$-$C_{10}$)-alkenyloxy, —($C_2$-$C_{10}$)-alkynyloxy halogen, -azido and $NH_2$, $R^{36}$ is selected from the group of —H and —OH, and B is a group of formula I (as defined above)

with the proviso that, said compound is not 8-aza-guanosine-$N^8$-β-D-2'-3'-didesoxy-glyceropentofuranosyl.

In another preferred embodiment, the group of formula I in compounds of formula VIII is selected from the group consisting of groups of formula I, wherein $X_5$ is N. Also preferred are compounds wherein $X_3$ is C linked to an H-donor group like $NH_2$.

3' deoxy- and 2'-3'-didesoxytriphosphate subunits according to formula VIII for example can be used as terminating nucleotides in sequencing methods.

More preferable, above mentioned method for enzymatic synthesis uses as a triphosphate subunit a compound of formula VIII as defined above.

By the above methods, it is principally possible to introduce only one monomer containing the moiety of the invention into one nucleic acid binding component, but also more than one, as the case may be. This is especially possible using chemical methods for the synthesis of nucleic acid binding compounds.

For synthesis of such triphosphate subunits several methods are known in the art (K. Burgess, D. Cook, Chem Rev. (2000), Vol 100, p. 2047-2059). One can use for example the method described by Ludwig, J., Acta Biochimica Biochim et Biophysica Acad. Sci. Hung., Vol. 16, page 131-133. Also matrix-dependent incorporation of similar pyrazolo[3,4-d]pyrimidines into DNA by polymerases has been demonstrated successfully.

These nucleic acid compounds can be usefully applied in hybridization methods. Therefore, a further subject of the invention is a method for the determination of a nucleic acid comprising the steps providing a sample suspected to contain said nucleic acid, providing a nucleic acid binding compound of claim 1, which is essentially complementary to a part or all of said nucleic acid, contacting said sample with said nucleic acid binding compound under conditions for binding said nucleic acid binding compound to said nucleic acid, determining the binding product formed from said nucleic acid and said nucleic acid binding compound as a measure of the presence of said nucleic acid.

Methods for determination of nucleic acids by hybridization are generally known, for example from Sambrook et al. (cited above). They can easily adopted for the use of probes of the present invention.

The heterocyclic groups of formula I are preferably used as universal bases capable to base pair with each of the four natural nucleobases. Nucleic acid binding compounds containing these heterocyclic groups can be used for example as probes and primers. Like other nucleic acid binding compounds they hybridize under stringent conditions only with nucleic acids having their complementary sequence. But at positions containing the universal bases according to the present invention the nucleic acid binding compound hybridize to a nucleic acid unrelated to its sequence. Therefore a non-discriminating hybridization is possible. This can be useful in the case the concrete natural base at a certain position of a nucleic acid to be determined (target nucleic acid) is not known. Normally one has to prepare several probes containing all possible complementary nucleotides at the position base pairing with the uncertain position of the target nucleic acid in order to be sure that the target nucleic acid can be determined. Using the nucleic acid binding compounds according to the present invention only one probe, which contains a universal base at that position is sufficient to allow the hybridization with the target nucleic acid. Especially when the nucleotide sequence of the target nucleic acid at several positions is not known, the use of a probe containing more than one universal base is preferred than using several probes of all possible sequences. Therefore the use of a probe according to the present invention can be extremely helpful for the determination of a nucleic acid when its sequence was deduced from a protein sequence, because the redundancy of the genetic code lead to a multitude of possible nucleic acid sequences.

Probes of the present invention also allow the determination of nucleic acids in the case that alleles or sequences belonging to subtypes containing different sequences at certain positions are known. An example is the determination of pathogens like bacteria or viruses, for example HCV, HBV and HIV. Often subtypes of these pathogens have different nucleic acid sequences at certain positions in their genomes, which hinder the determination of all subtypes belonging to one genus using only one probe. The use of probes containing universal bases according to the present invention can solve this problem.

Like other known universal bases, for example inosin, bases according to the invention pair with all natural nucleobases. However, the binding stability of said bases according the invention paired with all natural bases is very similar. Therefore when hybridizing a nucleic acid binding compound containing a universal base according to the invention with nucleic acids each having the same sequence except in the position pairing with the universal base (A, C, G, T), the Tm's are very similar. Using a defined 12-mer (see example 6) hybridized to a nucleic acid binding compound containing a universal base according to the present invention the ΔTm was 3° C. Therefore the binding stability of these hybridization complexes is less dependent to which natural base the universal base according to the invention pairs compared to known artificial bases, for example inosine.

Universal bases according to the invention contained in a probe or a primer can be used for the detection of nucleic acids having allelic differences or where the sequence at certain positions is not known. Because the Tm of the hybridization complexes is less dependent to which natural base the universal base according to the invention pairs the nucleic acid binding compounds of the present invention not only avoid the need of multiple probes or primers in order to determine nucleic acids containing partially unknown or allelic sequences, but they also improve the reliability of an assay and make it easier to find appropriate hybridization conditions which need to be used.

Nucleic acid binding compounds according to the present invention also can be applied in nucleic acid determination methods in the case the nucleic acid to be determined is amplified. Several methods are known in the art, like Qb-amplification, NASBA, LCR, SDA, TMA. A preferred method is PCR.

The nucleic acid binding compounds according to the present invention can be used as primers and probes. In the case, that the nucleic acid binding compound should be used as probe, it preferably will contain a detectable reporter group. Any hybrids formed from the nucleic acid binding compound and a nucleic acid can then be determined via the detectable reporter group. This group of assays can further be divided into two groups, one being the group of homogeneous assays and the other being the heterogeneous assays. In heterogeneous assays, preferably the hybrid (binding product) will be determined when bound to a solid phase. This embodiment has the advantage that any excess of probe and other components can be removed easily from the hybrid, thus make the determination easier. The hybrid formed can be captured to a solid phase either covalently, noncovalently, specifically or unspecifically. There are several embodiments which are known to a man skilled in the art.

In the so-called homogeneous assays, the hybrid formed will not be bound to a solid phase, but will be determined either directly or indirectly in solution. A preferred example of such assays is disclosed in PCT/US 91/05571 which is incorporated by reference here.

Therefore a further subject of the present invention is a method for the determination of the presence, absence or amount of a nucleic acid in a sample comprising the steps:

providing primers, a first primer being essentially complementary to a first binding sequence of said nucleic acid, and the second primer being essentially complementary to a binding sequence of a complement of this nucleic acid, and a probe being complementary to the nucleic acid or the complement thereof between the binding sequences of said primers, said probe being labeled at different subunits by at least two different reporter groups, subjecting the sample with said primers and said probe under conditions favouring extention of said primers and separating said reporter groups from each other by disintegrating the probe, and determining the extent of disintegration of the probe via at least one of said reporter groups, characterized in that at least one of said primer or/and probe are a nucleic acid binding compound containing at least one heterocyclic group of formula I.

Especially when using several nucleic acid binding compounds, for example when conducting PCR-, multiplex-PCR- or multiplex-hybridization-methods it is often difficult to find appropriate hybridization conditions ensuring a good specificity without loosing some specific hybridization complexes resulted from a lower Tm, which also means a lower stability. In the case of diagnostic methods this can lead to false negative results, which should be avoided. A further difficulty lies in the complexity of biological samples, for example blood or sputum. Such samples often have background nucleic acids, which may disturb the determination method, for example leading to false positive results. Therefore it is necessary to establish a very specific assay and a similar Tm of all hybridization complexes formed in such an assay is appreciated.

Therefore the heterocyclic groups of formula I can also be used in multiplex hybridization methods in order to change the Tm of one or more hybridization complexes formed in an assay. By introducing a heterocyclic group of formula I instead of a natural base contained in a nucleic acid binding compound used in that assay the Tm of the hybridization complex formed with its target nucleic acid can be changed. Such changes of the Tm still allows the specific hybridization of the nucleic acid compound with its target nucleic acid at a different temperature. This approach can be used to equalize the Tm's of the hybridization complexes which may occur in an assay with respect to target nucleic acids present in a sample. The use of heterocyclic groups of formula I is not restricted to positions of the nucleic acid binding compound which base pair with target nucleic acids containing unknown or allelic sequences, but can also applied to other positions. Therefore these heterocyclic groups can not only be used as universal bases but also as Tm equalizing bases in multiplex hybridization methods. A preferred application field are multiplex hybridization methods on chips which often use hundred to thousands hybridization probes.

These universal bases according to the present invention can also be used for in-vitro mutagenesis, for example using amplification methods like the PCR.

The invention furthermore relates to pharmaceutical compositions comprising one or more nucleic acid binding compounds containing at least one heterocyclic group of formula I, together with a physiologically acceptable excipients and, where appropriate, suitable additives and/or conventional auxiliary substances.

In a quite general manner, the present invention extends to the use of such nucleic acid binding compounds in therapeutically effective compositions. Such compositions are understood to mean to include the nucleic acid binding compounds according to the invention as antisense oligonucleotides, triple helix forming oligonucleotides, aptamers or ribozymes, in particular antisense oligonucleotides.

Also included in the present invention are intermediates and precursor compounds for the chemical synthesis of the described nucleic acid binding compounds. Preferred intermediates and precursor compounds are described below.

Preferred is a solid phase bound precursor for the synthesis of a nucleic acid binding compound comprising a backbone, wherein the backbone comprises a moiety of the general formula VI

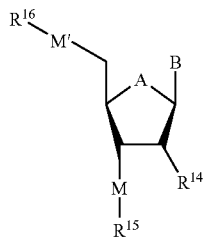

Formula VI wherein

A is selected from the group consisting of O, S, $CH_2$ and N—($C_1$-$C_6$)-alkyl, M and M' are independently selected from the group consisting of oxy, sulfanediyl, —$NR^{22}$—, —($C_1$-$C_{10}$)-alkyl-, or —O—($C_1$-$C_{10}$)-alkyl-O—, and —S—($C_1$-$C_{10}$)-alkyl-O— and —$NR^{22}$—($C_1$-$C_6$)-alkyl-O—, $R^{22}$ is selected from the group of —H, —($C_1$-$C_{10}$)-alkyl, a protecting group and a reporter group, $R^{14}$ is selected from the group consisting of —H, —$OR^{31}$, —($C_1$-$C_{10}$)-alkoxy, O-protecting group, S-protecting group, $NH_2$-protecting group, —($C_2$-$C_{10}$)-alkenyloxy, —($C_2$-$C_{10}$)-alkynyloxy, -halogen, -azido, SH, —($C_1$-$C_{10}$)-alkylmercapto, —$NH_2$ and —O-solid phase, $R^{15}$ and $R^{16}$ are independently selected from the group consisting of —H, —($C_1$-$C_6$)-alkyl, —($C_2$-$C_{10}$)-alkenyl, —($C_2$-$C_{10}$)-alkynyl, —($C_2$-$C_{10}$)-alkyl-carbonyl, —($C_3$-$C_{19}$)-alkenyl-carbonyl, —($C_3$-$C_{19}$)-alkynyl-carbonyl, —($C_6$-$C_{14}$)-aryl-($C_1$-$C_{10}$)-alkyl, protecting group and a solid phase B is the link to a moiety of formula I,

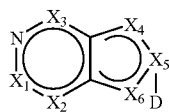

Formula I wherein
$X_1$ is independently from $X_4$, $X_5$ and $X_6$ selected from the group of N and $CR^1$, and $X_1$ is $CR^1$ if each of $X_2$ and $X_3$ is N, $X_2$ is independently from $X_4$, $X_5$ and $X_6$ selected from the group of N and $CR^2$, and $X_2$ is $CR^2$ if each of $X_1$ and $X_3$ is N, $X_3$ is independently from $X_4$, $X_5$ and $X_6$ selected from the group of N and $CR^3$, and $X_3$ is $CR^3$ if each of $X_1$ and $X_2$ is N, $X_4$ is independently from $X_1$, $X_2$ and $X_3$ selected from the group of N, $NR^{35}$ and $CR^4$, if $X_5$ is C and $X_6$ is $NR^{35}$, then $X_4$ is $CR^4$ or N,
if $X_5$ is C and $X_6$ is N, then $X_4$ is $NR^{35}$, and
if $X_5$ is C and $X_6$ is $CR^{34}$, then $X_4$ is $NR^{35}$, and
if $X_5$ is N, then $X_4$ is N or $CR^4$, $X_5$ is independently from $X_1$, $X_2$, $X_3$, $X_4$ and $X_6$ selected from the group of N and C, $X_6$ is independently from $X_1$, $X_2$ and $X_3$ selected from the group of N, $NR^{35}$ and $CR^{34}$, if $X_5$ is C and $X_4$ is $NR^{35}$, then $X_6$ is $CR^{34}$ or N,
if $X_5$ is C and $X_4$ is N, then $X_6$ is $NR^{35}$,
if $X_5$ is C and $X_4$ is $CR^4$, then $X_6$ is $NR^{35}$, and
if $X_5$ is N, then $X_6$ is N or $CR^{34}$, $R^1$, $R^2$, $R^3$, $R^4$ and $R^{34}$ are independently selected from the group consisting of —H, -halogen, —$OR^{13}$, —$SR^{19}$, —($C_1$-$C_{10}$)-alkyl, —($C_2$-$C_{10}$)-alkenyl, —($C_2$-$C_{10}$)-alkynyl, —$NO_2$, —$NR^5R^6$, -cyano, and —C(=O)$R^{11}$, $R^{11}$ is selected from the group consisting of —OH, —($C_1$-$C_6$)-alkoxy, —($C_6$-$C_{22}$)-aryloxy, and $NHR^{12}$, $R^5$, $R^6$, $R^{12}$, $R^{13}$, $R^{19}$ and $R^{35}$ are selected independently from the group consisting of —H, —($C_1$-$C_{10}$)-alkyl, —($C_2$-$C_{10}$)-alkenyl, —($C_2$-$C_{10}$)-alkinyl, —($C_6$-$C_{22}$)-aryl, a protecting group and a reporter group, D is the position of attachment of the group to the backbone, wherein any alkyl, alkenyl and alkynyl can be substituted or unsubstituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—($CH_2)_r]_s$—$NR^5R^6$.

r and s are independently of each other an integer of from 1 to 18, wherein one of $R^{14}$, $R^{15}$ or $R^{16}$ is a solid phase.

Such compounds of Formula VI can be used for chemical synthesis of nucleic acid binding compounds according to the invention as precursors. In this case the compounds are linked to a solid phase, preferred $R^{14}$ is O-solid phase or $R^{15}$ or $R^{16}$ is solid phase, most preferred $R^{15}$ is solid phase. It is also preferred that reactive groups are protected by protective groups.

Also included in the present invention are precursors and intermediates of a nucleic acid binding compound, wherein the backbone comprises a moiety of the general formula III

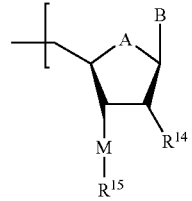

Formula III wherein
A is selected from the group consisting of O, S, $CH_2$ and N—($C_1$-$C_6$)-alkyl, M is selected from the group consisting of oxy, sulfanediyl, —$NR^{22}$—, —($C_1$-$C_{10}$)-alkyl-, or —O—($C_1$-$C_{10}$)-alkyl-O—, and —S—($C_1$-$C_{10}$)-alkyl-O— and —$NR^{22}$—($C_1$-$C_6$)-alkyl-O—, $R^{22}$ is selected from the group of —H, —($C_1$-$C_{10}$)-alkyl, a protecting group and a reporter group, $R^{14}$ is selected from the group consisting of —H, —OH, —($C_1$-$C_{10}$)-alkoxy, —($C_2$-$C_{10}$)-alkenyloxy, —($C_2$-$C_{10}$)-alkynyloxy, -halogen, -azido, SH, —($C_1$-$C_{10}$)-alkylmercapto, O-reporter group, O-solid phase and —$NH_2$, $R^{15}$ is selected from the group consisting of —H, —($C_1$-$C_6$)-alkyl, —($C_2$-$C_{10}$)-alkenyl, —($C_2$-$C_{10}$)-alkynyl, —($C_2$-$C_{10}$)-alkyl-carbonyl, —($C_3$-$C_{19}$)-alkenyl-carbonyl, —($C_3$-$C_{19}$)-alkynyl-carbonyl, —($C_6$-$C_{14}$)-aryl-($C_1$-$C_{10}$)-alkyl and a solid phase, B is the link to a moiety of formula I,

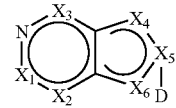

Formula I wherein
$X_1$ is independently from $X_4$, $X_5$ and $X_6$ selected from the group of N and $CR^1$, and $X_1$ is $CR^1$ if each of $X_2$ and $X_3$ is N, $X_2$ is independently from $X_4$, $X_5$ and $X_6$ selected from the group of N and $CR^2$, and $X_2$ is $CR^2$ if each of $X_1$ and $X_3$ is N, $X_3$ is independently from $X_4$, $X_5$ and $X_6$ selected from the group of N and $CR^3$, and $X_3$ is $CR^3$ if each of $X_1$ and $X_2$ is N, $X_4$ is independently from $X_1$, $X_2$ and $X_3$ selected from the group of N, $NR^{35}$ and $CR^4$, if $X_5$ is C and $X_6$ is $NR^{35}$, then $X_4$ is $CR^4$ or N,
if $X_5$ is C and $X_6$ is N, then $X_4$ is $NR^{35}$, and
if $X_5$ is C and $X_6$ is $CR^{34}$, then $X_4$ is $NR^{35}$, and
if $X_5$ is N, then $X_4$ is N or $CR^4$, $X_5$ is independently from $X_1$, $X_2$, $X_3$, $X_4$ and $X_6$ selected from the group of N and C, $X_6$ is independently from $X_1$, $X_2$ and $X_3$ selected from the group of N, $NR^{35}$ and $CR^{34}$, if $X_5$ is C and $X_4$ is $NR^{35}$, then $X_6$ is $CR^{34}$ or N,
if $X_5$ is C and $X_4$ is N, then $X_6$ is $NR^{35}$,
if $X_5$ is C and $X_4$ is $CR^4$, then $X_6$ is $NR^{35}$, and
if $X_5$ is N, then $X_6$ is N or $CR^{34}$, $R^1$, $R^2$, $R^3$, $R^4$ and $R^{34}$ are independently selected from the group consisting of —H, -halogen, —$OR^{13}$, —$SR^{19}$, —($C_1$-$C_{10}$)-alkyl, —($C_2$-$C_{10}$)-alkenyl, —($C_2$-$C_{10}$)-alkynyl, —$NO_2$, —$NR^5R^6$, -cyano, and —$C(\!=\!O)R^{11}$, $R^{11}$ is selected from the group consisting of —OH, —($C_1$-$C_6$)-alkoxy, —($C_6$-$C_{22}$)-aryloxy, and $NHR^{12}$, $R^5$, $R^6$, $R^{12}$, $R^{13}$, $R^{19}$ and $R^{35}$ are selected independently from the group consisting of —H, —($C_1$-$C_{10}$)-alkyl, —($C_2$-$C_{10}$)-alkenyl, —($C_2$-$C_{10}$)-alkinyl, —($C_6$-$C_{22}$)-aryl, a protecting group and a reporter group, D is the position of attachment of the group to the backbone, wherein any alkyl, alkenyl and alkynyl can be substituted or unsubstituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—($CH_2$)$_r$]$_s$—$NR^5R^6$.

r and s are independently of each other an integer of from 1 to 18, wherein $R^{14}$ is O-solid phase or $R^{15}$ is solid phase.

Solid phases for chemical synthesis of a nucleic acid binding compound according to the invention preferably also include linkers to fix the growing nucleic acid binding compound. Such linkers are known in the art. Preferably such linkers can be cleaved after synthesis to free said nucleic acid binding compound and can for example also be used to generate a free 3'-hydroxy group in said nucleic acid binding compound. Such linkers are known in the art, for example succinic acid bound via an ester and amide bond. Preferred $R^{15}$ is solid phase, but in the precursor for chemical synthesis of a nucleic acid binding compound according to formula III alternatively $R^{14}$ may also be solid phase. Reactive groups of said compound are preferably protected by a protective group.

A more general formula of preferred precursors and intermediates according to the present invention are compounds comprising a backbone, said backbone having attached heterocyclic groups characterized in that at least one of said heterocyclic

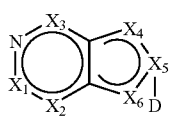

Formula I groups is a group of the general formula I wherein $X_1$ is independently from $X_4$, $X_5$ and $X_6$ selected from the group of N and $CR^1$, and $X_1$ is $CR^1$ if each of $X_2$ and $X_3$ is N, $X_2$ is independently from $X_4$, $X_5$ and $X_6$ selected from the group of N and $CR^2$, and $X_2$ is $CR^2$ if each of $X_1$ and $X_3$ is N, $X_3$ is independently from $X_4$, $X_5$ and $X_6$ selected from the group of N and $CR^3$, and $X_3$ is $CR^3$ if each of $X_1$ and $X_2$ is N, $X_4$ is independently from $X_1$, $X_2$ and $X_3$ selected from the group of N, $NR^{35}$ and $CR^4$, if $X_5$ is C and $X_6$ is $NR^{35}$, then $X_4$ is $CR^4$ or N,
if $X_5$ is C and $X_6$ is N, then $X_4$ is $NR^{35}$, and
if $X_5$ is C and $X_6$ is $CR^{34}$, then $X_4$ is $NR^{35}$, and
if $X_5$ is N, then $X_4$ is N or $CR^4$, $X_5$ is independently from $X_1$, $X_2$, $X_3$, $X_4$ and $X_6$ selected from the group of N and C, $X_6$ is independently from $X_1$, $X_2$ and $X_3$ selected from the group of N, $NR^{35}$ and $CR^{34}$, if $X_5$ is C and $X_4$ is $NR^{35}$, then $X_6$ is $CR^{34}$ or N,
if $X_5$ is C and $X_4$ is N, then $X_6$ is $NR^{35}$,
if $X_5$ is C and $X_4$ is $CR^4$, then $X_6$ is $NR^{35}$, and
if $X_5$ is N, then $X_6$ is N or $CR^{34}$, $R^1$, $R^2$, $R^3$, $R^4$ and $R^{34}$ are independently selected from the group consisting of —H, -halogen, —$OR^{13}$, —$SR^{19}$, —($C_1$-$C_{10}$)-alkyl, —($C_2$-$C_{10}$)-alkenyl, —($C_2$-$C_{10}$)-alkynyl, —$NO_2$, —$NR^5R^6$, -cyano, and —$C(\!=\!O)R^{11}$, $R^{11}$ is selected from the group consisting of —OH, —($C_1$-$C_6$)-alkoxy, —($C_6$-$C_{22}$)-aryloxy, and $NHR^{12}$, $R^5$, $R^6$, $R^{12}$, $R^{13}$, $R^{19}$ and $R^{35}$ are selected independently from the group consisting of —H, —($C_1$-$C_{10}$)-alkyl, —($C_2$-$C_{10}$)-alkenyl, —($C_2$-$C_{10}$)-alkinyl, —($C_6$-$C_{22}$)-aryl, a protecting group, a solid phase and a reporter group, r and s are independently of each other an integer of from 1 to 18, D is the position of attachment of the group to the backbone, said alkyl, alkenyl and alkynyl being unsubstituted or substituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—($CH_2$)$_r$]$_s$—$NR^5R^6$ wherein either said backbone is solid phase bound or wherein at least one of $R^5$, $R^6$, $R^{12}$, $R^{13}$, $R^{19}$ and $R^{35}$ is solid phase.

Beside the possibility that the precursor compound or intermediate is coupled to the solid phase at the backbone, it can also be linked at the heterocyclic group of formula I included in said compound, for example using a —OH, —SH or —$NH_2$ groups as attachment site. Preferably the other reactive groups of said compound are protected by protective groups.

The present invention is explained in more detail by the following examples:

EXAMPLES

Example 1

Figure 3:
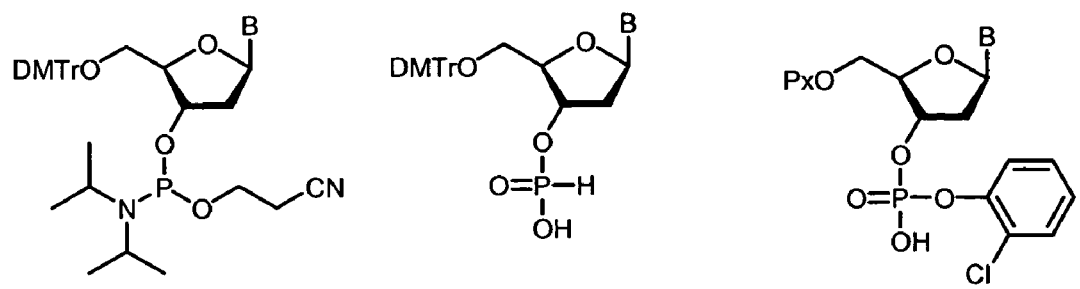
FIG. 3 shows different building blocks which can be used for chemical synthesis of oligonucleotides.

The substances used for synthesis are described using the systematic numbering. The synthesis of oligonucleotides containing universal nucleoside could be carried out by using standard protocols on commercial available DNA/RNA synthesizers. In general, the synthesis of the oligonucleotides proceeds through a phosphorous-based intermediate. Some examples of useful intermediates are shown in FIG. 3 including phosphoramidites according to Beaucage and Caruthers (1981) and H-phosphonates according to Froehler and Matteucci (1986).

The 4-(amino)-2-(2'-deoxy-β-D-erythro-pentofuranosyl)-2H-pyrazolo[3,4-d]pyrimidine (1) was first synthesized using phase-transfer glycosylation (F. Seela, H. Steker Helv. Chim. Acta 1985, 68, 563). A methyl protected phosphoramidite was prepared which required an extra step for the deprotection the methyl group, e.g thiophenol (F. Seela, K. Kaiser Helv. Chim. Acta 1988, 71, 1813). The 6-amino function of this building block was protected by a benzoyl group, which shows a rather long half-life time of deprotection (290 min at 40° C. in 25% aq. $NH_3$). This building block is not compatible with common protocols of P(III) oligonucleotide synthesis or the fast deprotection procedures.

Figure 4:
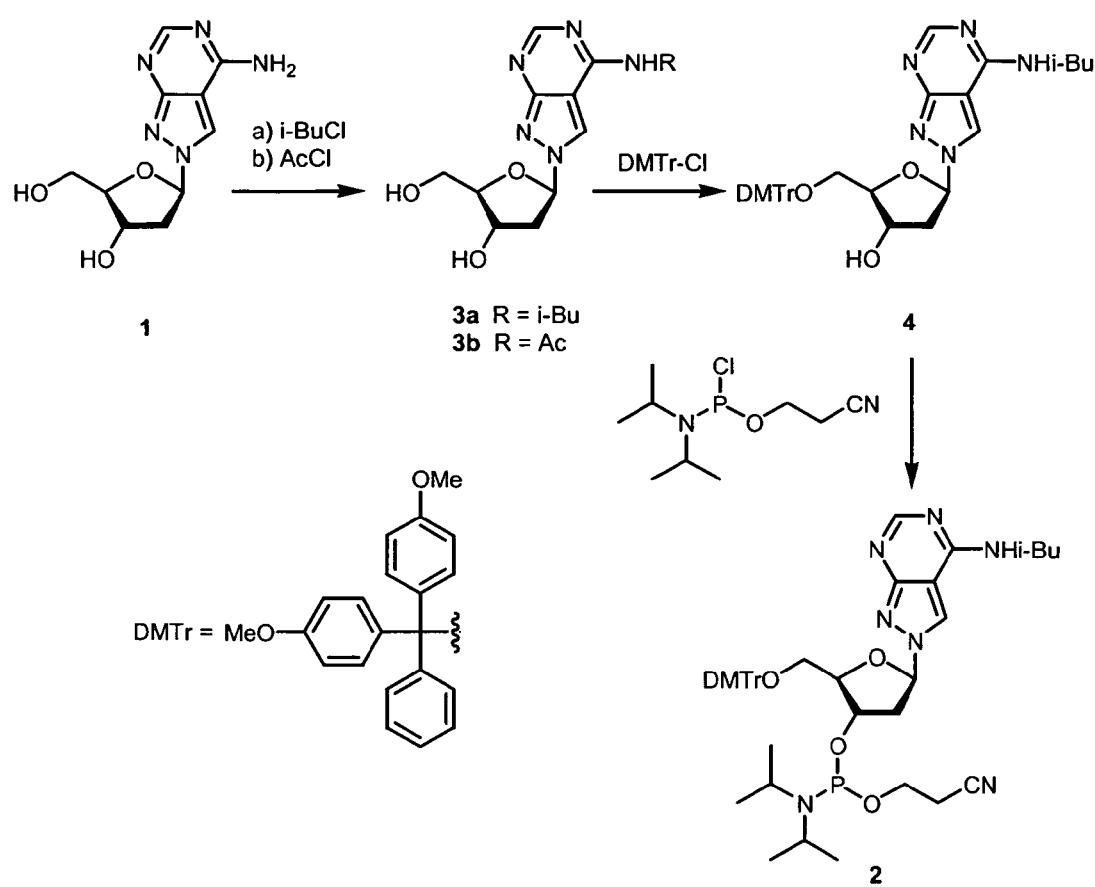
FIG. 4 shows the synthesis of a phosphoramidite of 8-aza-7-deazaadenine-$N^8$ 2'-deoxy-β-D-ribofuranosides.

For the synthesis of a new building block, fully compatible with the current cyanoethyl phosphoramidite protocol and fast deprotecting procedure see FIG. 4. The half-time value of the isobutyryl group deprotection is 22 min and that of the acetyl group is 8 min (both at 20° in 25% aq. ammonia).

Example 2

4-(Acetylamino)-2-(2'-deoxy-β-D-erythro-pentofuranosyl)-2H-pyrazolo[3,4-d]pyrimidine (3b, FIG. 4). The nucleoside 1 (see FIG. 4) (150 mg, 0.6 mol) was dried by co-evaporation with anh. pyridine and then dissolved in pyridine (4 ml). Me$_3$SiCl (0.4 ml, 3.1 mmol), the soln. stirred for 15 min, treated with acetic anhydride (0.28 ml, 3.0 mmol), and maintained for 3 h at r.t. The mixture was cooled (ice bath) and diluted with H$_2$O (1 ml). After 15 min, the resultant was treated with ice-cold 10% aq. NH$_3$ and was stirred for another 15 min. Then the soln. was evaporated to dryness and the residue was co-evaporated with toluene (2×10 ml). The residue was applied to FC [column 3×10 cm, solvent (CH$_2$Cl$_2$—MeOH 9:1)]. The title compound 3b was isolated as a white powder (110 mg, 62%). R$_f$(CH$_2$Cl$_2$—MeOH 9:1) 0.2; λ$_{max}$ (MeOH)/nm 239 (ε/dm$^3$ mol$^{-1}$ cm$^{-1}$ 8400), 273 (9300), 302 (6700); (Found: C, 48.99; H, 5.25; N, 23.68. C$_{12}$H$_{15}$N$_5$O$_4$ requires C, 49.14; H, 5.16; N, 23.88%); δ$_H$[250 MHz; (CD$_3$)$_2$SO] 2.24 (3H, s, Me), 2.41 (1H, m, 2'-H$_α$), 2.65 (1H, m, 2'-H$_β$), 3.55 (2H, m, 5'-H$_2$), 3.94 (1H, m, 4'-H), 4.43 (1H, m, 3'-H), 4.91 (1H, t, J 5.3, 5'-OH), 5.37 (1H, d, J 4.4, 3'-OH), 6.46 (1H, 't', J 6.1, 1'-H), 8.60 (1H, s, 6-H), 8.95 (1H, s, 3-H) and 11.22 (1H, s, NH).

Example 3

2-(2'-deoxy-β-D-erythro-pentofuranosyl)-4-(isobutyrylamino)-2H-pyrazolo[3,4-d]pyrimidine (3a, FIG. 4). Compound 1 (see FIG. 4) (1.0 g, 4.0 mmol) was dried by co-evaporation with pyridine (2×25 ml). The residue was suspended in pyridine (25 ml), and Me$_3$SiCl (2.5 ml, 19.7 mmol) was added at r.t. After 15 min stirring, the soln. was treated with isobutyric anhydride (3.26 ml, 19.9 mmol) and maintained at r.t. for 3 h. The was cooled in an ice bath, H$_2$O (5 ml) and subsequently (5 min later) 25% aq. NH$_3$ soln. (5 ml) were added, and stirring was continued for 15 min. The soln. was evaporated to dryness, dissolved in H$_2$O (25 ml), and was washed with diethylether (2×15 ml). The aq. layer was evaporated to dryness again, co-evaporated first with toluene (2×20 ml), and then with MeOH (2×20 ml). The residue was applied to FC [column 12×2 cm, solvent (CH$_2$Cl$_2$—MeOH 9:1)] to yield the title compond 3a as a colorless foam (1.05 g, 82%). R$_f$(CH$_2$Cl$_2$—MeOH 9:1) 0.25; λ$_{max}$(MeOH)/nm 239 (ε/dm$^3$ mol$^{-1}$ cm$^{-1}$ 8100), 273 (8900), 304 (6500); (Found: C, 52.48; H, 6.05; N, 21.70. C$_{14}$H$_{19}$N$_5$O$_4$ requires C, 52.33; H, 5.96; N, 21.80%); δ$_H$[250 MHz; (CD$_3$)$_2$SO] 1.15 (6H, s, Me$_2$), 2.40 (1H, m, 2'-H$_α$), 2.67 (1H, m, 2'-H$_β$), 2.91 (1H, h, J 6.7, CH), 3.60 (2H, m, 5'-H$_2$), 3.93 (1H, m, 4'-H), 4.46 (1H, m, 3'-H), 4.90 (1H, t, J 4.3, 5'-OH), 5.36 (1H, d, J 3.1, 3'-OH), 6.48 (1H, 't', J 5.5, 1'-H), 8.61 (1H, s, 6-H), 9.00 (1H, s, 3-H) and 11.20 (1H, s, NH).

Example 4

2-(2'-deoxy-5-O-(4,4'-dimethoxytriphenylmethyl)-β-D-erythro-pentofuranosyl)-4-(isobutyrylamino)-2H-pyrazolo[3,4-d]pyrimidine (4, see FIG. 4). The isobutyryl protected nucleoside 3 (see FIG. 4) (1.0 g, 3.1 mmol) was dried by repeated co-evaporation with anhydrous pyridine (2×20 ml) and dissolved in dry pyridine (25 ml). Then 4,4'-dimethoxytriphenylmethyl chloride (1.22 g, 3.6 mmol) was added and the solution was stirred for 3 h under argon at r.t. The mixture was cooled to room temperature, MeOH (5 ml) was added and the mixture stirred for another 30 min. Then the solution was reduced to half of the volume, dissolved in CH$_2$Cl$_2$ (100 ml), and extracted twice with 5% aq. NaHCO$_3$ soln. (50 ml) followed by saturated NaCl soln. (50 ml). The organic layer was dried (Na$_2$SO$_4$), filtered, evaporated and co-evaporated twice with toluene (30 ml). The residue was purified by FC [silica gel, 4×10 cm, solvent (CH$_2$Cl$_2$-acetone 8:2)] to yield the title compound 4 as a colourless foam (1.46 g, 75%). (Found: C, 67.36; H, 5.98; N, 11.30. C$_{35}$H$_{37}$N$_5$O$_6$ requires C, 67.40; H, 5.98; N, 11.23%); R$_f$ (CH$_2$Cl$_2$-acetone 8:2) 0.3; λ$_{max}$ (MeOH)/nm 236 (ε/dm$^3$ mol$^{-1}$ cm$^{-1}$ 28500), 273 (11400), 305 (6700); δ$_H$[250 MHz; (CD$_3$)$_2$SO] 1.11 (6H, dd, J 6.9, J 10.4, (CH$_3$)$_2$), 2.43 (1H, m, 2'-H$_α$), 2.81 (1H, m, 2'-H$_β$), 2.90 (1H, h, J 6.8, CH), 3.14 (2H, m, 5'-H$_2$), 3.66 and 3.69 (6H, 2 s, OMe), 4.04 (1H, m, 4'-H), 4.52 (1H, m, 3'-H), 5.42 (1H, d, J 5.0, 3'-OH), 6.54 (1H, dd, J 6.4, J 2.7, 1'-H), 6.74 (4H, m, ArH), 7.11-7.29 (9H, m, ArH), 8.62 (1H, s, 6-H), 9.05 (1H, s, 3-H) and 11.22 (1H, s, NH).

Example 5

2-(2'-deoxy-5-O-(4,4'-dimethoxytriphenylmethyl)-β-D-erythro-pentofuranosyl)-4-(isobutyrylamino)-2H-pyrazolo[3,4-d]pyrimidine-3'-[(2-cyanoethyl)-N,N-diisopropyl-phosphoramidite] (2, see FIG. 4). A solution of compound 4 (see FIG. 4) (800 mg, 1.28 mmol) in anhydrous CH$_2$Cl$_2$ (40 ml) was pre-flushed with Ar. Then (i-Pr)$_2$EtN (0.42 ml, 2.48 mmol) and 2-cyanoethyl diisopropylchlorophosphoramidite (0.42 ml, 1.88 mmol) were added under Argon. The reaction was monitored by TLC. After stirring for 20 min, the reaction mixture was diluted with CH$_2$Cl$_2$ (40 ml) and washed washed with 5% aquous NaHCO$_3$ soln. (2×20 ml) followed by saturated brine (20 ml). The organic layer was dried (Na$_2$SO$_4$), evaporated and co-evaporated with CH$_2$Cl$_2$ (2×20 ml). The diastereoic residue was purified by FC [silica gel, 4×10 cm, solvent (CH$_2$Cl$_2$-acetone 9:1)] to yield the title phosphoramidite 5 (FIG. 4) as a colourless foam (840 mg, 78%). R$_f$ (CH$_2$Cl$_2$-acetone 9:1) 0.5 and 0.6; δ$_P$[101 MHz; CDCl$_3$] 149.5 and 149.7.

Example 6

The oligonucleotides shown in Table 1 have been synthesized by oligonucleotide solid-phase synthesis according to the common protocol of phosphoramidite chemistry. The oligomers were purified by HPLC and the nucleoside composition was determined by reverese phase HPLC, enzymatic hydrolysis with snake venom phosphodiesterase followed by alkaline phosphatase. The oligonucleotides contain one ore two universal nucleoside 1 residues (see FIG. 4). They were hybridized and thermal denaturation profiles have been determined. 5'-d(T-A-G-G-T-C-A-A-T-A-C-T) (R1) (SEQ ID NO: 1) and 3'-d(A-T-C-C-A-G-T-T-A-T-G-A) (R2)(SEQ ID NO: 2)are standard oligonucleotides which are commonly used in these studies to elaborate the hybridization properties of modified nucleosides [F. Seela, I. Münster, U. Löchner, H. Rosemeyer, Helv. Chim. Acta (1998), Vol 81 , p 1139-1155]. The sequence is designed in such a way that other structures as hairpins or triplexes can be excluded.

The Tm-Values for oligonucleotides containing one or two 8-aza-7-deaza-N$^8$-2'-deoxyadenosines (A*) residues opposite to each of the four natural nucleosides dA, dC, dG and dT were measured according to [F. Seela, C. Wei, Helv. Chim. Acta (1999), Vol 82, p. 726-745]. The results are presented in Table 1.

TABLE 1

T$_m$-Values of antiparallel-stranded duplexes containing N$^8$-8-aza-7-deaza-2'-deoxyadenosine (dA*) residues opposite to each of the four natural nucleosides dA, dC, dG and dT.

| Duplex | SEQ ID NOS | | T$_m$ [° C.]$^a$ | ΔH° [kcal/mol] | ΔS° [cal/mol·K] | ΔG°$_{298}$ [kcal/mol] |
|---|---|---|---|---|---|---|
| 5'-d(T-A-G-G-T-C-A-A-T-A-C-T) | 1 | (R1) | 50 | −90 | −252 | −12.0 |
| 3'-d(A-T-C-C-A-G-T-T-A-T-G-A) | 2 | (R2) | | | | |
| 5'-d(T-A-G-G-T-C-A-A-T-A-C-T) | 1 | (R1) | 46 | −76 | −212 | −9.9 |
| 3'-d(A-T-C-C-A*-G-T-T-A-T-G-A) | 2 | (89) | | | | |
| 5'-d(T-A-G-G-C-C-A-A-T-A-C-T) | 4 | (98) | 46 | −80 | −225 | −9.9 |
| 3'-d(A-T-C-C-A*-G-T-T-A-T-G-A) | 3 | (89) | | | | |
| 5'-d(T-A-G-G-A-C-A-A-T-A-C-T) | 5 | (97) | 45 | −77 | −217 | −9.7 |
| 3'-d(A-T-C-C-A*-G-T-T-A-T-G-A) | 3 | (89) | | | | |
| 5'-d(T-A-G-G-G-C-A-A-T-A-C-T) | 6 | (99) | 44 | −73 | −205 | −9.4 |
| 3'-d(A-T-C-C-A*-G-T-T-A-T-G-A) | 3 | (89) | | | | |
| 5'-d(T-A-G-G-C-C-A-A-T-A-C-T) | 4 | (98) | 38 | −68 | −193 | −8.0 |
| 3'-d(A-T-C-C-A-G-T-T-A-T-G-A) | 2 | (R2) | | | | |
| 5'-d(T-A-G-G-A-C-A-A-T-A-C-T) | 5 | (97) | 40 | −62 | −172 | −8.4 |
| 3'-d(A-T-C-C-A-G-T-T-A-T-G-A) | 2 | (R2) | | | | |
| 5'-d(T-A-G-G-G-C-A-A-T-A-C-T) | 6 | (99) | 48 | −80 | −225 | −10.5 |
| 3'-d(A-T-C-C-A-G-T-T-A-T-G-A) | 2 | (R2) | | | | |
| 5'-d(T-A-G-G-T-C-A-A*-T-A-C-T) | 7 | (96) | 43 | −74 | −210 | −9.1 |
| 3'-d(A-T-C-C-A-G-T-T-A-T-G-A) | 2 | (R2) | | | | |
| 5'-d(T-A-G-G-T-C-A-A*-T-A-C-T) | 7 | (96) | 44 | −79 | −226 | −9.3 |
| 3'-d(A-T-C-C-A-G-T-C-A-T-G-A) | 8 | (105) | | | | |
| 5'-d(T-A-G-G-T-C-A-A*-T-A-C-T) | 7 | (96) | 44 | −72 | −202 | −9.4 |
| 3'-d(A-T-C-C-A-G-T-A-A-T-G-A) | 9 | (104) | | | | |
| 5'-d(T-A-G-G-T-C-A-A*-T-A-C-T) | 7 | (96) | 46 | −75 | −209 | −9.8 |
| 3'-d(A-T-C-C-A-G-T-G-A-T-G-A) | 10 | (103) | | | | |
| 5'-d(T-A-G-G-T-C-A-A-T-A-C-T) | 1 | (R1) | 36 | −64 | −183 | −7.5 |
| 3'-d(A-T-C-C-A-G-T-C-A-T-G-A) | 8 | (105) | | | | |
| 5'-d(T-A-G-G-T-C-A-A-T-A-C-T) | 1 | (R1) | 39 | −65 | −184 | −8.2 |
| 3'-d(A-T-C-C-A-G-T-A-A-T-G-A) | 9 | (104) | | | | |
| 5'-d(T-A-G-G-T-C-A-A-T-A-C-T) | 1 | (R1) | 44 | −74 | −209 | −9.2 |
| 3'-d(A-T-C-C-A-G-T-G-A-T-G-A) | 10 | (103) | | | | |
| 5'-d(T-A-G-G-T-C-A*-A*-T-A-C-T) | 11 | (80) | 44 | −92 | −265 | −9.9 |
| 3'-d(A-T-C-C-A-G-T-T-A-T-G-A) | 2 | (R2) | | | | |
| 5'-d(T-A-G-G-T-C-A*-A*-T-A-C-T) | 11 | (80) | 42 | −79 | −225 | −9.0 |
| 3'-d(A-T-C-C-A-G-T-C-A-T-G-A) | 8 | (105) | | | | |
| 5'-d(T-A-G-G-T-C-A*-A*-T-A-C-T) | 11 | (80) | 42 | −78 | −223 | −9.1 |
| 3'-d(A-T-C-C-A-G-T-A-A-T-G-A) | 9 | (104) | | | | |
| 5'-d(T-A-G-G-T-C-A*-A*-T-A-C-T) | 11 | (80) | 39 | −67 | −190 | −8.1 |
| 3'-d(A-T-C-C-A-G-T-G-A-T-G-A) | 10 | (103) | | | | |
| 5'-d(T-A-G-G-T-C-A-A-T-A-C-T) | 1 | (R1) | 33 | −61 | −174 | −6.9 |
| 3'-d(A-T-C-C-S-G-T-T-A-T-G-A) | 12 | (119) | | | | |
| 5'-d(T-A-G-G-C-C-A-A-T-A-C-T) | 4 | (98) | 35 | −65 | −187 | −7.4 |
| 3'-d(A-T-C-C-S-G-T-T-A-T-G-A) | 12 | (119) | | | | |
| 5'-d(T-A-G-G-A-C-A-A-T-A-C-T) | 13 | (E13) | 35 | −76 | −222 | −7.2 |
| 3'-d(A-T-C-C-S-G-T-T-A-T-G-A) | 12 | (119) | | | | |
| 5'-d(T-A-G-G-G-C-A-A-T-A-C-T) | 14 | (E11) | 40 | −71 | −202 | −8.6 |
| 3'-d(A-T-C-C-S-G-T-T-A-T-G-A) | 12 | (119) | | | | |
| 5'-d(T-A-G-G-T-C-A-S-T-A-C-T) | 15 | (118) | 33 | −47 | −129 | −7.0 |
| 3'-d(A-T-C-C-A-G-T-T-A-T-G-A) | 2 | (R2) | | | | |
| 5'-d(T-A-G-G-T-C-A-S-T-A-C-T) | 15 | (118) | 34 | −52 | −146 | −7.1 |
| 3'-d(A-T-C-C-A-G-T-C-A-T-G-A) | 8 | (105) | | | | |
| 5'-d(T-A-G-G-T-C-A-S-T-A-C-T) | 15 | (118) | 34 | −51 | −141 | −7.2 |
| 3'-d(A-T-C-C-A-G-T-A-A-T-G-A) | 9 | (104) | | | | |
| 5'-d(T-A-G-G-T-C-A-S-T-A-C-T) | 15 | (118) | 33 | −48 | −131 | −7.0 |
| 3'-d(A-T-C-C-A-G-T-G-A-T-G-A) | 10 | (103) | | | | |

$^a$) Measured at 260 nm in 1 M NaCl, 100 mM MgCl$_2$, and 60 mM Na-cacodylate (pH 7.0) with 5 μM single strand concentration.
$^b$) No sigmoidal melting curve.

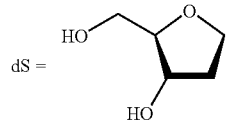

dS =

According to Table 1, the insertion of a single universal nucleoside 1 (see FIG. 4) in the center position of the oligomers R1 (SEQ ID NO: 1) and R2 (SEQ ID NO: 2) opposite to each of the four naturally occurring nucleosides dA, dC, dG and dT show only a minor change of the Tm-value. The melting point difference between of the first modificated oligonucleotide (89)(SEQ ID NO: 3) against each of the four unmodified nucleosides is between 0° C. and 3° C. A similar behavior is observed when two of the universal nucleoside residues are incorporated opposite to the four common DNA-constituents. These results were totally unexpected. Later examination of the possible duplex structure (FIG. 5) showed, that base pairs might be formed, which all contain two hydrogen bonds and not three as the dG-dC pair and two of the dA-dT pair. The distance of the sugar attachment sites are all almost identical when the pyriraidine base (dC or dT) exhibits the normal glycosylation site and the glycosylation site of the "purine base" base is position-8.

Example 7

The synthesis of a phosphoramidite of 7-deaza-guanosin $C^8$-2'-deoxy-β-D-ribofuranoside is described below (see also FIG. 6).

Figure 6:
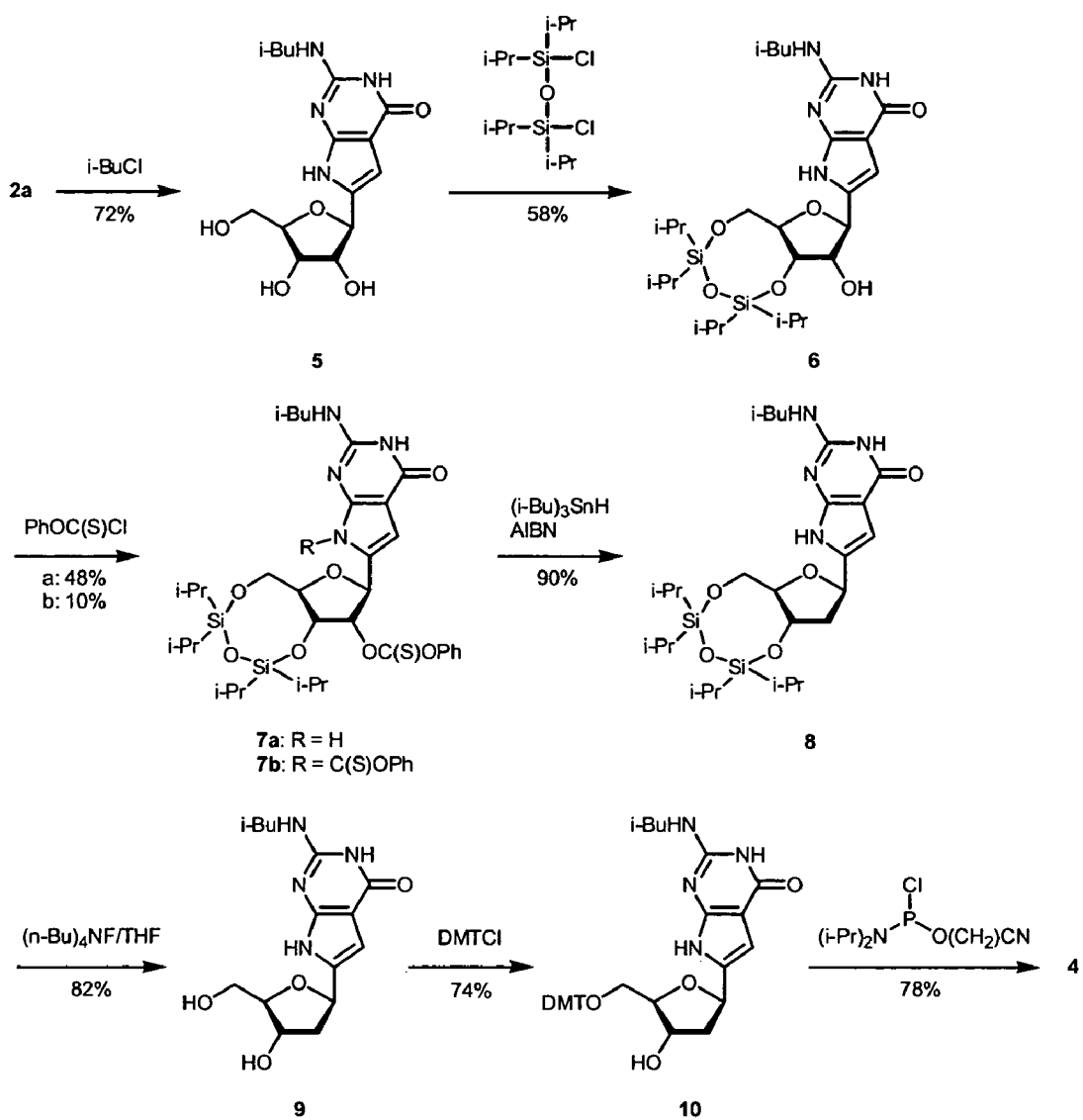
FIG. 6 shows the synthesis of a phosphoramidite of 7-deaza-guanin-$C^8$ 2'-deoxy-β-D-ribofuranosides.
Figure 7A:
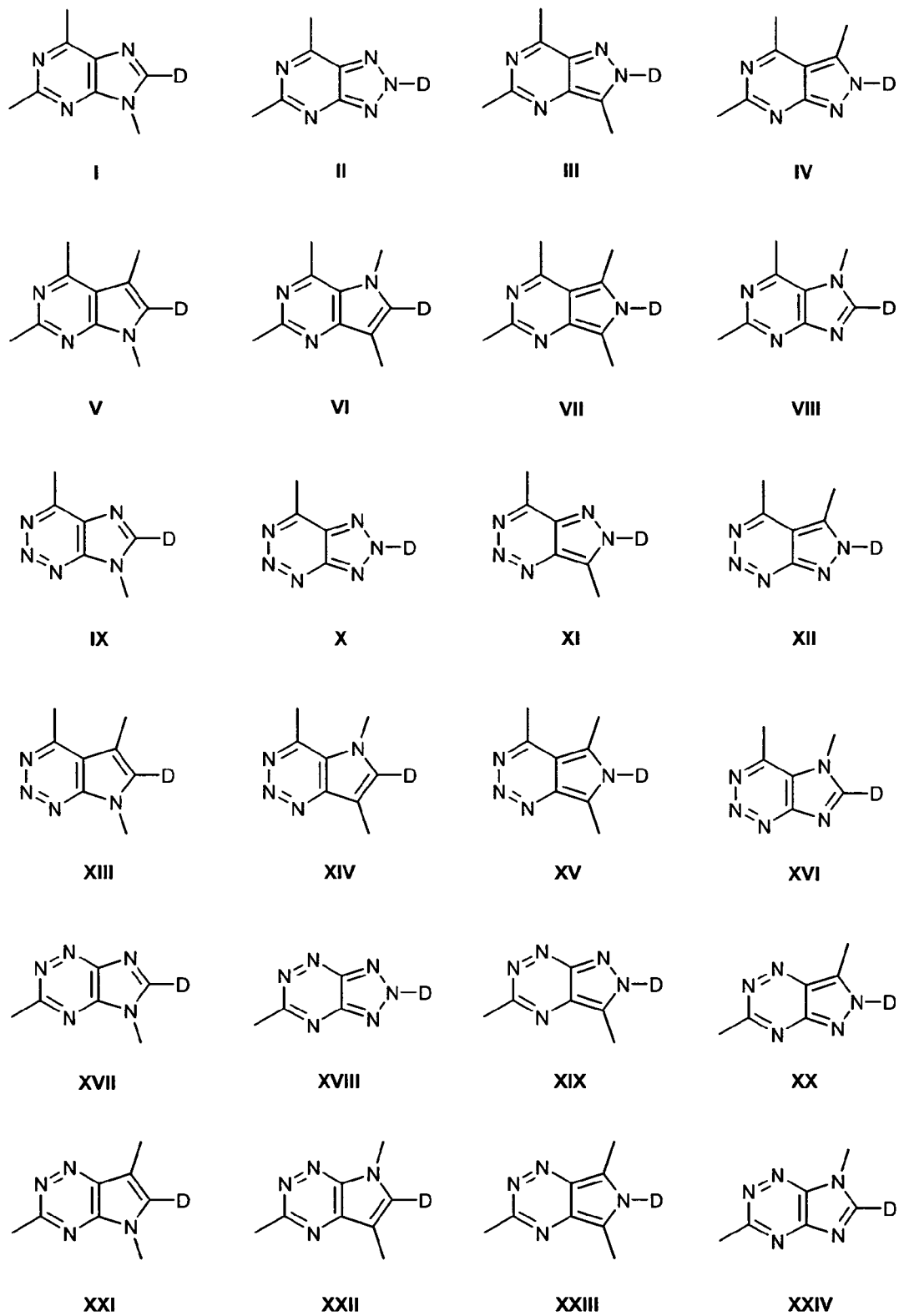
FIG. 7a and FIG. 7b show the ring system of possible heterocyclic groups of the general formula I according to the present invention (substituents which are defined in formula I are not further specified in the figure, but are indicated with a line).
Figure 7B:
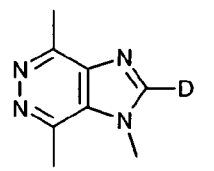
Figure 7B:
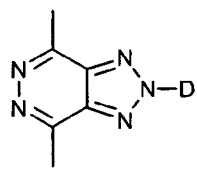
Figure 7B:
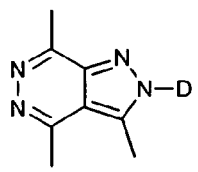
Figure 7B:
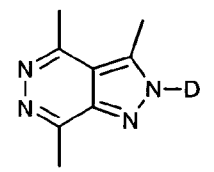
Figure 7B:
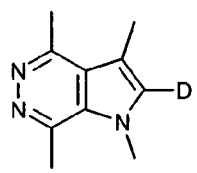
Figure 7B:
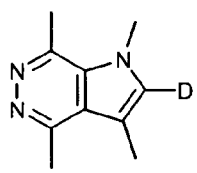
Figure 7B:
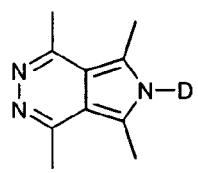
Figure 7B:
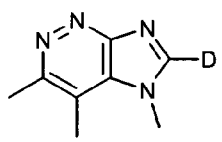
Figure 7B:
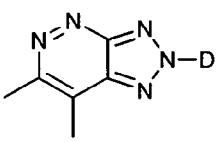
Figure 7B:
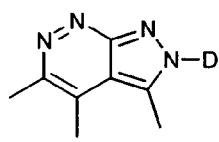
Figure 7B:
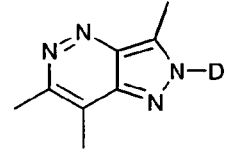
Figure 7B:
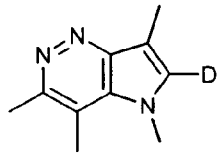
Figure 7B:
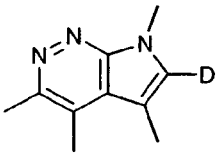
Figure 7B:
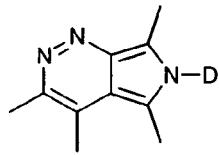
Figure 7B:
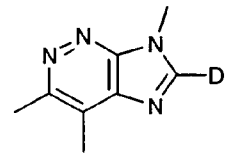
Figure 7B:
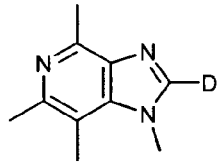
Figure 7B:
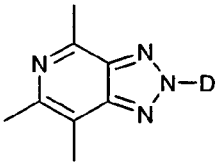
Figure 7B:
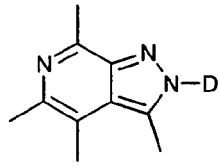
Figure 7B:
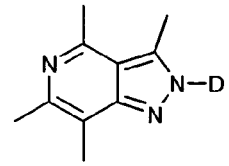
Figure 7B:
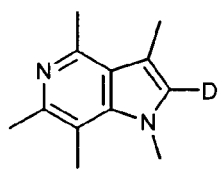
Figure 7B:
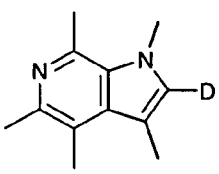
Figure 7B:
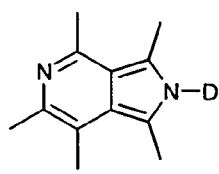
Figure 7B:
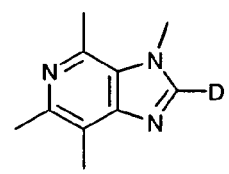

2-Isobutyrylamino-6-(β-D-ribofuranosyl)-7H-pyrrolo[2,3-d]pyrimidin-4(3H)-one (5, FIG. 6). Compound 2a (2-amino-6-β-D-ribofuranosyl-7H-pyrrolo[2,3-d]pyrimidin-4(3H)-one, Girgis et al., J. Med. Chem., Vol. 33, p. 2750-2755, 1990) (520 mg, 1.84 mmol) was dried by co-evaporation with pyridine (2×10 ml). The residue was suspended in pyridine (5 ml), and Me$_3$SiCl (3.0 ml, 23.6 mmol) was added at r.t. After 15 min of stirring, the soln. was treated with isobutyric anhydride (0.4 ml, 3.82 mmol) and maintained at r.t. for 6 h. The solution was cooled in an ice bath, H$_2$O (3 ml) and subsequently (5 min later) 25% aq. NH$_3$ soln. (3 ml) were added, while the stirring was continued for 15 min. The soln. was evaporated to dryness, dissolved in H$_2$O (20 ml), and washed with ether (2×10 ml). The aq. layer was evaporated to dryness again, co-evaporated first with toluene (2×10 ml), and then with MeOH (2×10 ml). The residue was applied to FC (column 10×2 cm, CH$_2$Cl$_2$—MeOH 8:2, v/v) to yield the title compound 5 (FIG. 6) as a pale yellow powder (470 mg, 72%). R$_f$ (CH$_2$Cl$_2$—MeOH 8:2, v/v) 0.3; $\lambda_{max}$(MeOH)/nm 275 (ε/dm$^3$ mol$^{-1}$ cm$^{-1}$ 16600), 294 (15000 sh); (Found: C, 51.23; H, 5.82; N, 15.95. C$_{15}$H$_{20}$N$_4$O$_6$ requires C, 51.13; H, 5.72; N, 15.90%); δ$_H$ [250 MHz; d$_6$-DMSO] 1.11 (6H, d, J 6.8, Me$_2$), 2.76 (1H, h, J 6.8, CH), 3.51 (1H, m, 5'-H), 3.57 (1H, m, 5"-H), 3.78 (1H, m, 4'-H), 3.97 (2H, m, 2'-H, 3'-H), 4.62 (1H, d, J 6.3, 1'-H), 4.91 (1H, d, J 4.6, 3'-OH), 4.92 (1H, t, J 5.8, 5'-OH), 5.06 (1H, d, J 5.8, 2'-OH), 6.39 (1H, d, J 1.4, 5-H), 11.34 (1H, s, NH), 11.60 (1H, s, NH), and 11.78 (1H, s, NH).

2-Isobutyrylamino-[3,5-(1,1,3,3-tetraisopropyl-1,3-disiloxan-1,3-yl)-6-β-D-ribofuranosyl]-7H-pyrrolo[2,3-d]pyrimidin-4(3H)-one (6). To solution of compound 2 (500 mg, 1.42 mmol) in anhydrous pyridine (6 ml) was added 1,3-dichloro-1,1,3,3-tetraisopropyldisiloxane (0.55 ml, 1.71 mmol) under argon atmosphere. The reaction mixture was stirred at r.t. over night, and extracted twice with 5% aq. NaHCO$_3$ soln. (25 ml) followed by saturated NaCl soln. (25 ml). The organic layer was dried (Na$_2$SO$_4$), filtered, evaporated and co-evaporated twice with toluene (20 ml). The residue was purified by FC [silica gel, 4×10 cm, CH$_2$Cl$_2$—MeOH 95:5, v/v) to yield the title compound 6 (FIG. 6) as a colourless foam (485 mg, 58%). R$_f$ (CH$_2$Cl$_2$—MeOH 95:5) 0.5; $\lambda_{max}$(MeOH)/nm 275 (ε/dm$^3$ mol$^{-1}$ cm$^{-1}$ 17200), 293 (15700 sh); (Found: C, 54.51; H, 7.88; N, 9.51. C$_{27}$H$_{46}$N$_4$O$_7$Si$_2$ requires C, 54.52; H, 7.79; N, 9.42%); δ$_H$ [250 MHz; d$_6$-DMSO] 0.89-1.04 (28H, m, (CHMe$_2$)$_4$), 1.12 (6H, d, J 6.7, Me$_2$), 2.77 (1H, h, J 6.7, CH), 3.87 (1H, m, 5"-H), 3.91 (1H, m, 5'-H), 3.94 (1H, m, 4'-H), 4.15 (1H, d't', J 5.0, J 3.5, 2'-H), 4.24 (1H, dd, J 6.0, J 6.7, 3'-H), 4.71 (1H, d, J 3.0, 1'-H), 5.03 (1H, d, J 5.3, 2'-OH), 6.35 (1H, s, 5-H), 11.34 (1H, br. s, NH), 11.67 (1H, s, NH), and 11.74 (1H, br. s, NH).

2-Isobutyrylamino-[2-O-phenoxythiocarbonyl-3,5-(1,1,3,3-tetraisopropyl-1,3-disiloxan-1,3-yl)-6-β-D-ribofuranosyl]-7H-pyrrolo[2,3-d]pyrimidin-4(3H)-one (7a). To a suspension of compound 6 (FIG. 6) (1.71 g, 2.88 mmol) and 4-dimethylaminopyridine (2.1 g; 17.2 mmol) in anhydrous acetonitrile (65 ml) was added phenylchlorothionoformiate (0.48 ml, 3.48 mmol) under an argon atmosphere. After stirring the reaction mixture over night at r.t., it was evaporated to dryness, and dissolved with CH$_2$Cl$_2$ (50 ml). The organic phase was washed twice with cold 1 N hydrochloric acid (20 ml), water (20 ml) and saturated aq. NaHCO$_3$ soln. (20 ml). The organic layer was dried (NaSO$_4$) and the solvent was evavorated to dryness. The residue, which was a mixture of two major compounds, was purified by FC [silica gel, 4×10 cm, CH$_2$Cl$_2$-acetone 9:1, v/v). The slower moving major product was yielded as a colourless foam and was characterized as the title compound 7a (FIG. 6) (1.0 g, 48%). R$_f$ (CH$_2$Cl$_2$-acetone 9:1) 0.6; $\lambda_{max}$(MeOH)/nm 274 (ε/dm$^3$ mol$^{-1}$ cm$^{-1}$ 18000), 294 (16200 sh); (Found: C, 56.00; H, 6.82; N, 7.60. C$_{34}$H$_{50}$N$_4$O$_8$SSi$_2$ requires C, 55.86; H, 6.89; N, 7.66%); δ$_H$ [250 MHz; d$_6$-DMSO] 0.95-1.03 (28H, m, (CHMe$_2$)$_4$), 1.11 (6 H, d, J 6.9, Me$_2$), 2.77 (1H, h, J 6.9, CH), 3.90 (1H, m, 5"-H), 4.00 (2H, m, 5'-H, 4'-H), 4.66 (1H, d't', J 6.4, 3'-H), 5.14 (1H, d, J 2.8, 1'-H), 5.90 (1H, 't', J 4.2, 1'-H), 7.12 (2H, d, J 7.9, arom. H), 7.33 (1H, t, J 7.2, arom. H), 7.48 (2H, t, J 7.5, arom. H), 11.36 (1H, s, NH), 11.81 (1H, s, NH), and 11.87 (1H, s, NH).

2-Isobutyrylamino-7-phenoxythiocarbonyl-[2-O-phenoxythiocarbonyl-3,5-(1,1,3,3-tetraisopropyl-1,3-disiloxan-1,3-yl)-6-β-D-ribofuranosyl]-7H-pyrrolo[2,3-d]pyrimidin-4(3H)-one (7b, FIG. 6). The faster migrating by-product of the synthesis procedure described above yielded as a yellow powder (250 mg, 10%) and was characterized as compound 7b. R$_f$ (CH$_2$Cl$_2$-acetone 9:1) 0.8; $\lambda_{max}$(MeOH)/nm 272 (ε/dm$^3$ mol$^{-1}$ cm$^{-1}$ 20900), 295 (15600 sh); (Found: C, 56.89; H, 6.16; N, 6.41. C$_{41}$H$_{54}$N$_4$O$_9$S$_2$Si$_2$ requires C, 56.79; H, 6.28; N, 6.46%); δ$_H$ [250 MHz; d$_6$-DMSO] 0.97-1.08 (28H, m, (CHMe$_2$)$_4$), 1.13 (6H, d, J 6.4, Me$_2$), 2.85 (1H, d, J 6.8, CH), 3.93 (1H, d, J 8.9, 4'-H), 4.01 (1H, d, J 12.1, 5'-H), 4.20 (1H, d, J 12.7, 5"-H), 4.65 (1H, dd, J 8.9, J 4.5, 3'-H), 5.78 (1H, s, 1'-H), 6.14 (1H, d, J 4.5, 2'-H), 6.72 (2H, d, J 7.6, arom. H), 6.88 (1H, s, 5-H), 7.29 (1H, t, J 7.3, arom. H), 7.38 (2H, d, J 8.3, arom. H), 7.41 (2H, t, J 8.0, arom. H), 7.45 (1H, t, J 8.3, arom. H), 7.57 (2H, t, J 7.6, arom. H), 11.44 (1H, br. s, NH), and 12.18 (1H, br. s, NH).

2-Isobutyrylamino-[3,5-(1,1,3,3-tetraisopropyl-1,3-disiloxan-1,3-yl)-6-(2'-deoxy-β-D-erythro-pentofuranosyl]-7H-pyrrolo[2,3-d]pyrimidin-4(3H)-one (8). To a solution of compound 7a (1.06 g, 1.45 mmol) in anhydrous toluene (60 ml) was added 2,2'-azobis(2-methylpropionitrile) (AIBN, 120 mg, 0.73 mmol) and tri-n-butyltin hydride (3.8 ml, 14.1 mmol) under an argon atmosphere. The reaction flask was placed in a pre-heated oil bath (70° C.). After 2 h, the mixture was cooled to r.t. and the solvent was evaporated. The oily residue was applied to FC [silica gel, 4×10 cm, CH$_2$Cl$_2$-MeOH 95:5, v/v) to yield the title compound 8 (FIG. 6) as a colorless foam (755 mg, 90%). R$_f$ (CH$_2$Cl$_2$—MeOH) 0.4; $\lambda_{max}$(MeOH)/nm 274 (ε/dm$^3$ mol$^{-1}$ cm$^{-1}$ 17200), 293 (15500); (Found: C, 56.21; H, 8.15; N, 9.63. C$_{27}$H$_{46}$N$_4$O$_6$Si$_2$ requires C, 56.02; H, 8.01; N, 9.63%); δ$_H$ [250 MHz; d$_6$-DMSO] 0.99-1.02 (28H, m, (CHMe$_2$)$_4$), 1.11 (6H, d, J 6.6, Me$_2$), 2.18 (1H, m, 2'-H$_\alpha$), 2.41 (1H, m, 2'-H$_\beta$), 2.76 (1H, h, J 6.5, CH), 3.75 (2 H, m, 5'-H$_2$), 3.95 (1H, m, 4'-H), 4.51 (1H, m, 3'-H), 5.02 (1H, t, J 7.2, 1'-H), 6.37 (1 H, s, 5-H), 11.36 (1H, br. s, NH), 11.70 (1H, br. s, NH), and 11.77 (1H, s, NH).

2-Isobutyrylamino-6-(2'-deoxy-β-D-erythro-pentofuranosyl)-7H-pyrrolo[2,3-d]pyrimidin-4(3H)-one (9, FIG. 6). To a solution of compound 8 (865 g, 1.50 mmol) in THF (10 ml) was added a 1 N solution of tetrabutylammonium fluoride (8 ml, 8 mmol) in THF. The mixture was stirred at r.t. for 3 h and the solvent was evaporated. The residue was applied to FC [silica gel, 4×10 cm, $CH_2Cl_2$—MeOH 9:1, v/v) to yield the title compound 9 as a colourless powder (410 mg, 82%). $R_f$($CH_2Cl_2$—MeOH 9:1) 0.25; $\lambda_{max}$(MeOH)/nm 272 ($\epsilon$/dm$^3$ mol$^{-1}$ cm$^{-1}$ 15900), 291 (14200); (Found: C, 53.54; H, 5.94; N, 16.63. $C_{15}H_{20}N_4O_5$ requires C, 53.57; H, 5.99; N, 16.66%); $\delta_H$ [250 MHz; $d_6$-DMSO] 1.11 (6H, d, J 6.9, Me$_2$), 2.01 (1H, m, 2'-H$_\alpha$), 2.11 (1H, m, 2'-H$_\beta$), 2.76 (1 H, h, J 7.0, CH), 3.45 (2H, m, 5'-H$_2$), 3.74 (1H, m, 4'-H), 4.20 (1H, m, 3'-H), 4.79 (1 H, t, J 4.2, 5'-OH), 5.02 (1H, dd, J 10.1, J 5.7, 1'-H), 5.08 (1H, d, J 3.5, 3'-OH), 6.35 (1H, s, 5-H), 11.33 (1H, br. s, NH), 11.63 (1H, br. s, NH), and 11.76 (1H, s, NH).

2-Isobutyrylamino-6-[2'-deoxy-5-O-(4,4'-dimethoxytrityl)-β-D-erythro-pentofuranosyl]-7H-pyrrolo[2,3-d]pyrimidin-4(3H)-one (10, FIG. 6). Compound 9 (350 mg, 1.04 mmol) was dried by repeated co-evaporation with anhydrous pyridine (2×10 ml) and dissolved in dry pyridine (15 ml). Then 4,4'-dimethoxytriphenylmethyl chloride (407 mg, 1.2 mmol) was added and the solution was stirred for 3 h under argon at r.t. The mixture was cooled to room temperature, MeOH (3 ml) was added and the mixture was stirred for another 30 min. Then the solution was reduced to half of the volume, extracted with $CH_2Cl_2$ (50 ml), washed with 5% aq. NaHCO$_3$ soln. (25 ml, twice) followed by saturated NaCl soln. (25 ml). The organic layer was dried (Na$_2$SO$_4$), filtered, evaporated and co-evaporated with toluene (20 ml). The residue was purified by FC [silica gel, 4×10 cm, $CH_2Cl_2$—MeOH 9:1, v/v) to yield the title compound 10 as a colourless foam (480 mg, 74%). $R_f$ ($CH_2Cl_2$—MeOH 95:5, v/v) 0.2; $\lambda_{max}$ (MeOH)/nm 272 ($\epsilon$/dm$^3$ mol$^{-1}$ cm$^{-1}$ 15700), 294 (13200); (Found: C, 67.70; H, 6.04; N, 8.72. $C_{36}H_{28}N_4O_7$ requires C, 67.70; H, 6.00; N, 8.77%); $\delta_H$ [250 MHz; $d_6$-DMSO] 1.11 (6H, d, J 6.6, Me$_2$), 2.10 (1H, m, 2'-H$_\alpha$), 2.18 (1H, m, 2'-H$_\beta$), 2.76 (1H, h, J 6.6, CH), 3.02 (2H, m, 5'-H$_2$), 3.72 (6H, s, Me$_2$), 3.91 (1H, m, 4'-H), 4.16 (1H, m, 3'-H), 5.10 (1H, dd, J 9.0, J 6.4, 1'-H), 5.16 (1H, d, J 3.5, 3'-OH), 6.36 (1H, s, 5-H), 6.82-6.87 (4H, m, arom. H), 7.17-7.39 (9H, m, arom. H), 11.38 (1H, br. s, NH), 11.77 (1H, br. s, NH), and 11.79 (1H, s, NH).

2-Isobutyrylamino-6-[2'-deoxy-5-O-(4,4'-dimethoxytrityl)-β-D-erythropentofuranosyl]-7H-pyrrolo[2,3-d]pyrimidin-4(3H)-one 3'-(2-Cyanoethyl-N,N-diisopropylphosphoramidite (4). A solution of compound 10 (530 mg, 0.83 mmol) in anhydrous $CH_2Cl_2$ (30 ml) was pre-flushed with argon. Then (i-Pr)$_2$EtN (0.27 ml, 1.59 mmol) and 2-cyanoethyl diisopropylchlorophosphoramidite (0.27 ml, 1.21 mmol) were added under argon. The reaction was monitored by TLC. After stirring for 20 min, the reaction mixture was diluted with $CH_2Cl_2$ (30 ml) and washed with 5% aquous NaHCO$_3$ soln. (2×15 ml) followed by saturated brine (15 ml). The organic layer was dried (Na$_2$SO$_4$), evaporated and co-evaporated with $CH_2Cl_2$ (2×20 ml). The residue was purified by FC (silica gel, 4×10 cm, $CH_2Cl_2$-acetone 8:2, v/v) to yield the title compound 4 as a colourless foam (540 mg, 78%). $R_f$ ($CH_2Cl_2$-acetone 9:1, v/v) 0.7, 0.75; $\delta_H$ [101 MHz; CDCl$_3$] 148.8 and 150.9.

TABLE 2

Molecular weights determined by MALDI-TOF mass spectroscopy of the modified oligonucleotides containing C8 7-deaza-2'-deoxyguanosine.

| Oligonucleotide | SEQ ID NOS | M$^+$ (calc.) | M$^+$ (found) |
|---|---|---|---|
| 5'-d(AG*T ATT G*AC CTA) (HD47) | 16 | 3640.7 | 3639.7 |
| 5'-d(TAG* G*TC AAT ACT) (HD48) | 17 | 3640.7 | 3640.3 |
| 5'-d(AGT ATT G*AC CTA) (HD75) | 18 | 3641.7 | 3641.4 |
| 5'-d(TAG G*TC AAT ACT) (HD76) | 19 | 3641.7 | 3641.0 |
| 5'-d(AtiC iCAG* TTA TG*A) (HD86) | 20 | 3668.7 | 3667.9 |
| 5'-d(TiCA TAA iCTG* G*AT) (HD87) | 21 | 3668.7 | 3667.1 |

Example 8

Figure 9:
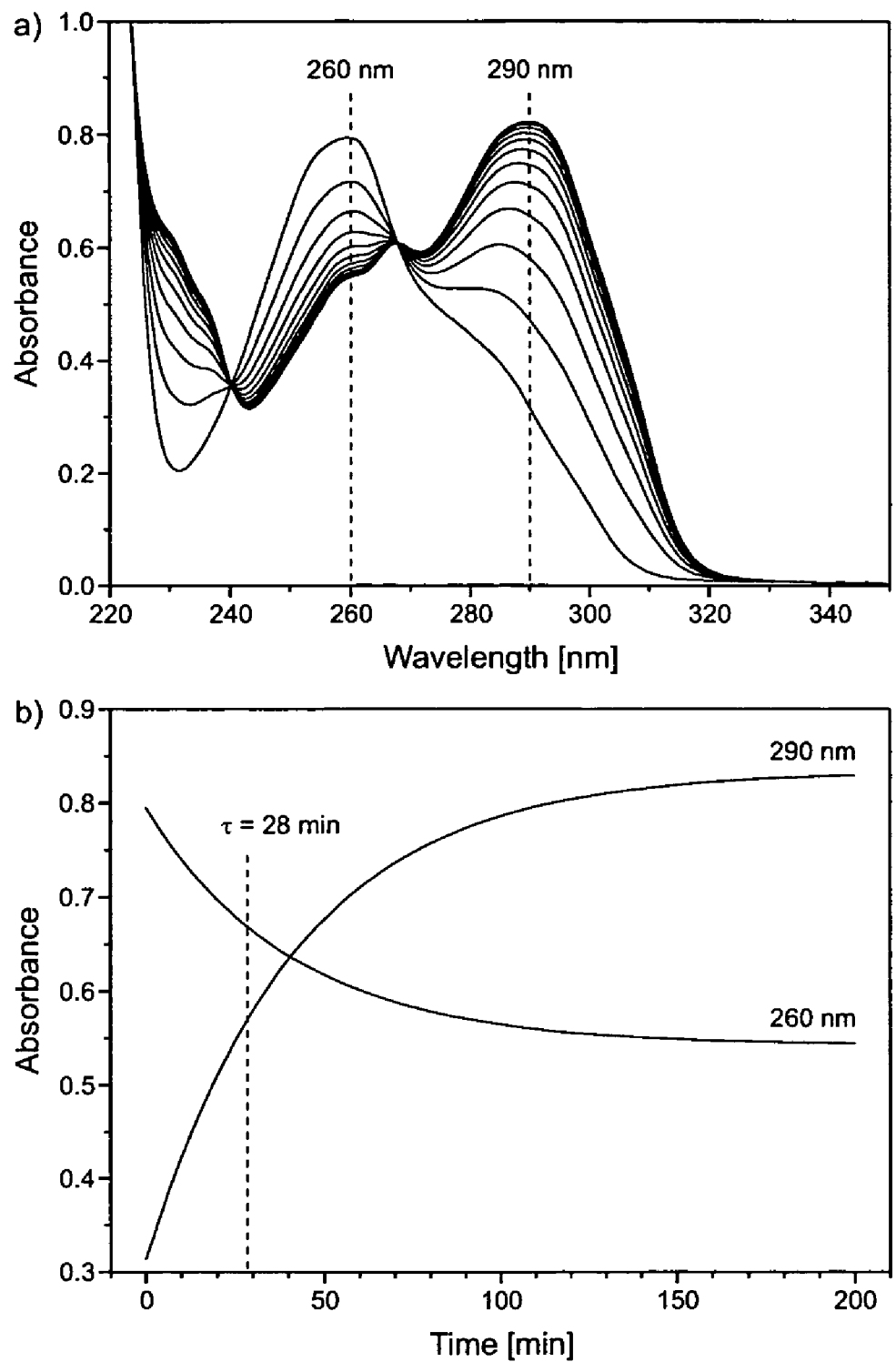
FIG. 9 shows the UV-spectrophotometrical assignment of the half-life value of the methoxy-amino exchange of compound 2a (FIG. 8, 25% aq. $NH_3$, 40° C.).
Figure 10:
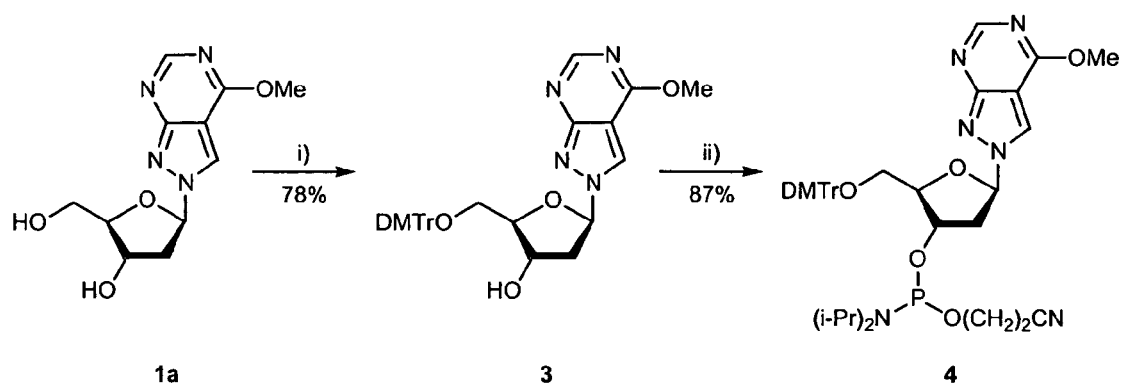
FIG. 10 shows the synthesis of the phosphoramidite 2-[2'-deoxy-5'-O-(4,4'-dimethoxytriphenylmethyl)-β-D-erythropentofuranosyl]-4-methoxy-2H-pyrazolo[3,4-d]pyrimidin-3'-[(2-cyanoethyl)-N,N-diisopropyl-phosphoramidite] with a methoxy group as a precursor for an amino function: i) DMTr-Cl, pyridine, 3 h, R.T. ii) (i-Pr)$_2$NP(Cl)O(CH$_2$)$_2$CN, CH$_2$Cl$_2$, 20 min, R.T.

Synthesis of a phosphoramidite (4, FIG. 10) with a methoxy group as a precursor for an amino function Results The methoxy group of the pyrazolo[3,4-d]pyrimidines 1a and 2a (FIG. 8) (F. Seela, H. Steker, Helv. Chim. Acta 1985, 68, 563-570) can easily be converted into an amino function on the oligonucleotide level. Thus, the methoxy phosphoramidite 4 (FIG. 10) can be used as precursor to incorporate 1b or 2b (FIG. 8) in DNA by the solid-phase oligonucleotide synthesis. The conversion of the methoxy group occurs during the deprotection of the oligonucleotide with ammonia. The half-life values of the methoxy-amino exchange were determined UV-spectrophoto-metrically by treatment with 25% aq. ammonia at 40° C. For the half-life values see Table 3 and FIG. 9. Next, the 4,4'-dimethoxytriphenylmethyl group was introduced into the 5'-OH position and compound 3 (FIG. 10) was converted to the β-cyanoethyl phosphoramidite 4 (FIG. 10) using the standard protocol (FIG. 10). The coupling yield of phosphoramidite 4 (FIG. 10) was found to be at least 99%.

TABLE 3

Half-life values (π) of the substitution of the
6-methoxy group by a amino function of the $N^8$-linked
nucleoside 1a (FIG. 8) and its $N^9$-counterpart 2a (FIG. 8).

|  |  | τ [min] | λ [min] |
|---|---|---|---|
| $N^8m^6c^7z^8I_d$ | 1a | 28 | 260, 290 |
| $N^9m^6c^7z^8I_d$ | 2a | 67 | 275 |

[a] Measured UV-spectrophotometrically at 40° C. in 25% aq. $NH_3$.

Experimental

2-[2'-deoxy-5-O-(4,4'-dimethoxytriphenylmethyl)-β-D-erythro-pentofuranosyl]-4-methoxy-2H-pyrazolo[3,4-d]pyrimidine (3, FIG. 10). Compound 1a (FIG. 10, 410 mg, 1.54 mmol) was dried by repeated co-evaporation with anhydrous pyridine (2×10 ml) and dissolved in dry pyridine (10 ml). Then, 4,4'-dimethoxytriphenylmethyl chloride (620 mg, 1.83 mmol) was added, and the solution was stirred for 3 h under argon at r.t. Then, MeOH (2 ml) was added, and the mixture was stirred for another 30 min. Then, the solution was reduced to half of the volume, dissolved in $CH_2Cl_2$ (50 ml), and extracted twice with a 5% aq. $NaHCO_3$ soln. (20 ml) followed by saturated brine (20 ml). The organic layer was dried ($Na_2SO_4$), filtered, evaporated and co-evaporated twice with toluene (20 ml). The residue was purified by FC (silica gel, 3×10 cm, solvent $CH_2Cl_2$-acetone 8:2). Compound 3 was obtained as a colorless foam (680 mg, 78%). TLC ($CH_2Cl_2$-acetone 8:2, v/v): 0.5; UV (MeOH): 235 (27800), 273 (12100), 304 (7300); $^1$H-NMR ($d_6$-DMSO): 2.44 (1H, m, 2'-$H_α$), 2.75 (1H, m, 2'-$H_β$), 3.16 (2H, m, 5'-$H_2$), 3.69 (3H, s, Me), 3.70 (3H, s, Me), 4.05 (4H, m, Me, 4'-H), 4.52 (1H, m, 3'-H), 5.43 (1H, d, J=5.0 Hz, 3'-OH), 6.42 (1H, dd, J=6.8 Hz, J=3.3 Hz, 1'-H), 6.74-6.81 (4H, m, arom. H), 7.17-7.32 (9H, m, arom. H), 8.56 (1H, s, 3-H), 8.79 (1H, s, 6-H). Anal. calcd. for $C_{32}H_{32}N_4O_6$ (568.62): C, 67.59; H, 5.67; N, 9.85. Found: C, 67.39; H, 5.58; N, 9.76.

2-[2'-Deoxy-5'-O-(4,4'-dimethoxytriphenylmethyl)-β-D-erythro-pentofuranosyl]-4-methoxy-2H-pyrazolo[3,4-d]pyrimidin-3'-[(2-cyanoethyl)-N,N-diisopropyl-phosphoramidite] (4, FIG. 10). A stirred solution of compound 3 (FIG. 10, 510 mg, 0.90 mmol) in anh. $CH_2Cl_2$ (30 ml) was pre-flushed with Ar. Then, (i-Pr)$_2$EtN (0.30 ml, 1.72 mmol) and 2-cyanoethyl diisopropylchlorophosphoramidite (0.30 ml, 1.34 mmol) were added under Ar. The reaction was monitored by TLC. After stirring for 20 min, the reaction mixture was diluted with $CH_2Cl_2$ (30 ml) and washed with a 5% aq. $NaHCO_3$ soln. (2×20 ml) followed by saturated brine (20 ml). The organic layer was dried ($Na_2SO_4$), evaporated and co-evaporated with $CH_2Cl_2$ (2×20 ml). The residue was purified by FC (silica gel, 3×10 cm, solvent: $CH_2Cl_2$-acetone 9:1) to yield compound 4 as a colourless foam (600 mg, 87%). TLC ($CH_2Cl_2$-acetone 9:1, v/v): 0.6, 0.7; $^{31}$P-NMR ($CDCl_3$): 150.2, 150.5. Anal. calcd. for $C_{41}H_{49}N_6O_7P$ (768.84): C, 64.05; H, 6.42; N, 10.93. Found: C, 64.19; H, 6.42;

Example 9

Synthesis of 4-(amino-2-(2'-deoxy-β-D-erythro-pentofuranosyl)-2H-pyrazolo[3,4-d]pyrimidine 5'-monophosphate 40 mg (0.16 mmol) of 4-(amino-2-(2'-deoxy-β-D-erythro-pentofuranosyl)-2H-pyrazolo[3,4-d]pyrimidine were dissolved in 4 ml Triethylphosphate and 87 μl Diisopropyl ethyl amin were added. The flask was cooled in an ice, bath to 0-4° C. 12 μl Phosphoroxychloride were added. After stirring for 10 min at 0-4° Triethylamin/acetic acid buffer 0.1M pH 8.5 was added. The solvents were evaporated at 0.1 mbar at 40° C. using a rotary evaporator. The residue was dissolved in 20 ml water and applied to a column (d=16 mm l=150 mm) filled with ion exchange Material DEAE Sephadex A 25 Cl-. Buffer A water, Buffer B 0.5 M LiCl, gradient in 60 min to 100% B monitoring by UV/VIS detector at 270 nm. The product eluates at 40% B . The corresponding fractions were collected and evaporated at reduced pressure to a volume of 1-3 ml. The product solution was added to a 80 ml of a 2:1 mixture of Aceton/Ethanol. The suspension was centrifuged, the resulting pellet was washed 3 times with acetone to remove LiCl and than dried in high vacuum. yield 30 mg $^{31}$P NMR (Bruker DPX 300, Solvent $D_2O$) [ppm]: 5.043 (s)

Example 10

Synthesis of 4-(amino)-2-(2'-deoxy-β-D-erythro-pentofuranosyl)-2H-pyrazolo[3,4-d]pyrimidine 5' triphosphate 30 mg (0.11 mmol) of the monophosphate lithium salt was transformed to the tri N-butylammonium salt by Ion exchange with a Dowex WX 8 column. The tri N-butylammoniumsalt was dissolved in 3 ml dry DMF 89 mg(0.55 mmol) Carbonyldiimidazol were added the mixture was stirred for 2 h at RT. 0.5 ml Methanol were added and the mixture stirred for 20 min at RT. Methanol was removed by evaporation under reduced pressure. Then 0.7 ml of a 0.8 M solution of bis tributylammonium pyrophosphate in DMF (0.55 mmol) was added The mixture was stirred overnight at roomtemp. The solvents were evaporated at 0.1 mbar at 40° C. by using a rotary evaporator. For desalting the mixture was acidified with acetic acid to pH 3 and applied to a column (d=14 mm l=130 mm) filled with Carboraffin-P. It was eluated with 200 ml water and then with 200 ml diluted ammonia (1000 ml water+6 ml konz ammonia). The ammonia solution which contains the triphosphate, was evaporated at reduced pressure.

For further purification the crude product was dissolved in 10.0 ml water and applied to a column (d=16 mm l=150 mm) filled with ion exchange Material QAE Sephadex A 25 Cl-. Buffer A water, Buffer B 0.5 M LiCl, gradient 20 min 0% B than in 60 min to 100% B monitoring by UV/VIS detector at 260 nm. The product eluates at 49% B. The corresponding fractions were collected and evaporated at reduced pressure to a volume of 2 ml. The product solution was added to a 80 ml of a 2:1 mixture of Aceton/Ethanol. The suspension was centrifuged, the resulting pellet was washed 3 times with acetone to remove LiCl and than dried in high vacuum. yield: 10 mg. $^{31}$P NMR (Bruker DPX 300, Solvent $D_2O$ [ppm]: −3.91 (d); −9.47 (d); −19.27 (t)

Example 11

Figure 11:
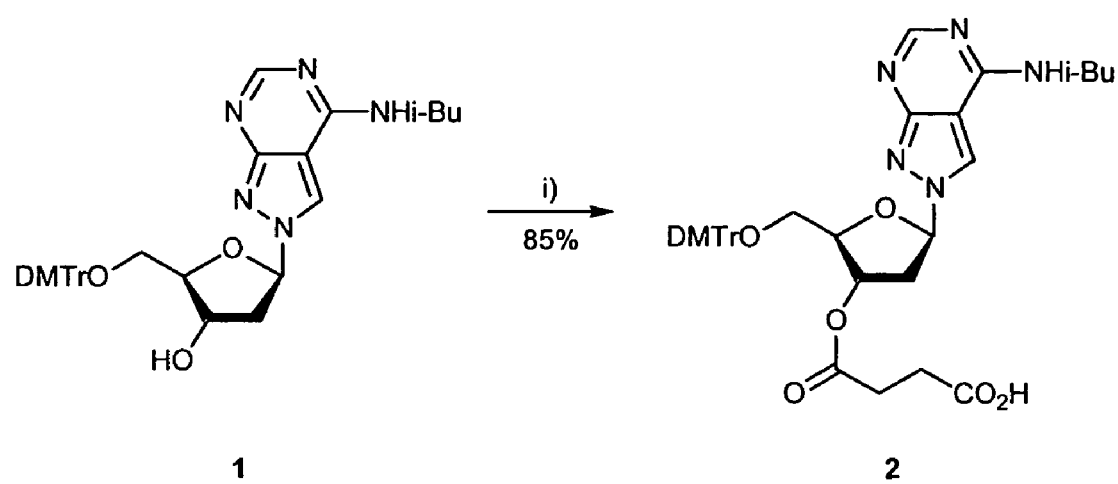
FIG. 11 shows the synthesis of the 3'-succinylester 2: i) Succinic anhydride, 4-(N,N-dimethylamino)pyridine, Et$_3$N, 1,2-dichloroethane, 30 min, 50° C. This compound can be bound to a solid phase.

Synthesis and solid-phase binding of 2-[2'-deoxy-5'-O-(4,4'-dimethoxytriphenyl methyl)-β-D-erythro-pentofuranosyl]-4-(isobutyrylamino)-2H-pyrazolo[3,4-d]pyrimidine 3'-(3-Carboxypropanoate) (2, FIG. 11).

To a solution of compound 1 (FIG. 11)(350 mg, 0.56 mmol) in anhydrous 1,2-dichloroethane (1.5 ml), 4-(N,N-dimethylamino)pyridine (35 mg, 0.28 mmol), succinic anhydride (40 mg, 0.53 mmol) and $Et_3N$ (78 μl, 0.56 mmol) were added. The mixture was stirred for 30 min at 50° C. Then the solution was diluted with 1,2-dichloro-ethane (20 ml) and washed with ice-cold citric acid solution (3×10 ml) and $H_2O$ (3×10 ml). The organic layer was dried with $Na_2SO_4$, filtered, evaporated and the residue submitted to FC (silica gel, 15×3 cm, acetonitrile-$H_2O$ 9:1). The main zone yielded compound 2 as a colorless powder (352 mg, 0.48 mmol, 85%). TLC (acetonitrile-$H_2O$ 9:1): 0.8; UV (MeOH): 237 (28500), 273 (11500), 305 (6600); $^1$H-NMR ($d_6$-DMSO): 1.12 (6H, 't', J=7.4, $(CH_3)_2$), 2.88 (1H, m, CH), 2.95 (1H, m, 2'-$H_\beta$), 3.21 (2H, m, 5'-$H_2$), 3.68 (6H, s, $CH_3$), 4.25 (1H, m, 4'-H), 5.40 (1H, m, 3'-H), 6.61 (1H, 't', J=5.4, 1'-H), 6.73 (4H, m, ArH), 7.13-7.28 (9H, m, ArH), 8.62 (1H, s, 6-H), 9.07 (1H, s, 3-H), 11.26 (1H, br. s, NH), 12.32 (1H, br. s, $CO_2H$). Anal. calcd. for $C_{39}H_{41}N_5O_9$ (723.77): C, 64.72; H, 5.71; N, 9.68. Found: C, 64.69; H, 5.76; N, 9.62.

The compound 2 can be bound to a solid phase using the protocol described in F. Seela, H. Debelak, N. Usman, A. Burgin, L. Beigelman, Nucleic Acids Res. 1998, Vol. 26, page 1010-1018.

---

What is claimed is:

1. A nucleic acid binding compound comprising a backbone, said backbone having attached heterocyclic groups wherein at least one of said heterocyclic groups has the formula I
wherein

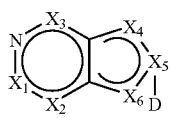

Formula I $X_1$ is independently from $X_4$, $X_5$ and $X_6$ selected from the group of N and $CR^1$, and $X_1$ is $CR^1$ if each of $X_2$ and $X_3$ is N, $X_2$ is independently from $X_4$, $X_5$ and $X_6$ selected from the group of N and $CR^2$, and $X_2$ is $CR^2$ if each of $X_1$ and $X_3$ is N, $X_3$ is independently from $X_4$, $X_5$ and $X_6$ selected from the group of N and $CR^3$, and $X_3$ is $CR^3$ if each of $X_1$ and $X_2$ is N, $X_4$ is independently from $X_1$, $X_2$ and $X_3$ selected from the group of N, $NR^{35}$ and $CR^4$, if $X_5$ is C and $X_6$ is $NR^{35}$, then $X_4$ is $CR^4$ or N,
if $X_5$ is C and $X_6$ is N, then $X_4$ is $NR^{35}$, and
if $X_5$ is C and $X_6$ is $CR^{34}$, then $X_4$ is $NR^{35}$, and
if $X_5$ is N, then $X_4$ is N or $CR^4$, $X_5$ is independently from $X_1$, $X_2$, $X_3$, $X_4$ and $X_6$ selected from the group of N and C, $X_6$ is independently from $X_1$, $X_2$ and $X_3$ selected from the group of N, $NR^{35}$ and $CR^{34}$, if $X_5$ is C and $X_4$ is $NR^{35}$, then $X_6$ is $CR^{34}$ or N,
if $X_5$ is C and $X_4$ is N, then $X_6$ is $NR^{35}$,
if $X_5$ is C and $X_4$ is $CR^4$, then $X_6$ is $NR^{35}$, and
if $X_5$ is N, then $X_6$ is N or $CR^{34}$, $R^1$, $R^2$, $R^3$, $R^4$ and $R^{34}$ are independently selected from the group consisting of —H, -halogen, —$OR^{13}$, —$SR^{19}$, —($C_1$-$C_{10}$)-alkyl, —($C_2$-$C_{10}$)-alkenyl, —($C_2$-$C_{10}$)-alkynyl, —$NO_2$, —$NR^5R^6$, -cyano, and —C(=O)$R^{11}$, $R^{11}$ is selected from the group consisting of —OH, —($C_1$-$C_6$)-alkoxy, —($C_6$-$C_{22}$)-aryloxy, and $NHR^{12}$, $R^5$, $R^6$, $R^{12}$, $R^{13}$, $R^{19}$ and $R^{35}$ are selected independently from the group consisting of —H, —($C_1$-$C_{10}$)-alkyl, —($C_2$-$C_{10}$)-alkenyl, —($C_2$-$C_{10}$)-alkynyl, —($C_6$-$C_{22}$)-aryl, a protecting group and a reporter group, r and s are independently of each other an integer of from 1 to 18, D is the position of attachment of the group to the rest of the nucleic acid binding compound, said alkyl, alkenyl and alkynyl being unsubstituted or substituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—($CH_2$)$_r$]$_s$—$NR^5R^6$ with the proviso that, if the heterocyclic group of the general formula I is 8-aza-7-deazaadenine (A*) which is attached to a 2' Deoxy β-D erythropentofuranosyl moiety the sequence of said nucleic acid binding compound is not selected from the group consisting of $(A*T)_6$ (SEQ ID NO:22), CTGGA*TCCAG (SEQ ID NO:23) or CTGGATCCA*G SEQ ID NO:24), if the heterocyclic group of the general formula I is $N^6$-methylated-8-aza-7-deazaadenine ($A*^m$) which is attached to a 2'-Deoxy-β-D-erythropentofuranosyl moiety the sequence of said nucleic acid binding compound is not selected from the group consisting of $(A*^mT)_6$ (SEQ ID NO:25), CTGGA*$^m$TCCAG (SEQ ID NO:26), CTGGATCCA*$^m$G (SEQ ID NO:27), ATATATA*$^m$TATAT (SEQ ID NO:28), ATGCAGA*$^m$ TCTGCA (SEQ ID NO:29) or CTGGATCCA*$^m$ G (SEQ ID NO:27), if the heterocyclic group of the formula I is 8-aza-7-deazaadenine which is attached to a β-D-ribofuranosyl moiety the sequence of said compound contains at least one further heterocycle other than adenine and other than 8-aza-7-deazaadenine, if the heterocyclic group of the general formula I is 8-aza-9-deaza-9-methyl-guanin which is $N^8$-attached with a 2'-deoxy-β-D-ribofuranosyl moiety the sequence of said compound contains at least one further heterocycle other than thymidine and other than 8-aza-9-deaza-9-methyl-guanin and if $X_4$, $X_5$, $X_6$ of the heterocyclic group of the general formula I are N and $X_1$ is $CR^1$, $X_2$ is N and $X_3$ is $CR^3$, $R^1$ and $R^3$ are not H, OH, $NH_2$ or protected $NH_2$.

2. The nucleic acid binding compound of claim 1, wherein $X_5$ is N.

3. The nucleic acid binding compound of claim 1, wherein $X_3$ is $CR^3$.

4. The nucleic acid binding compound of claim 1, wherein $X_3$ is $CNR^5R^6$.

5. The nucleic acid binding compound of claim 1, wherein the backbone comprises sugar and phosphate moieties.

6. The nucleic acid binding compound of claim 5, wherein the sugar configuration is selected from the group consisting of the α-D-, β-D-, α-L- and β-L-configurations.

7. The nucleic acid binding compound of claim 6, wherein the sugar moiety is a 2'-deoxy-β-D-erythropentofuranosyl moiety.

8. The nucleic acid binding compound of claim 1, wherein said nucleic acid compound comprises one or more moieties of the formula II

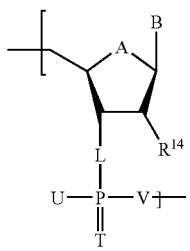

Formula II wherein

A is selected from the group consisting of O, S, $CH_2$, $N-(C_1-C_{10})$-alkyl, L is selected from the group consisting of oxy, sulfanediyl, $-CH_2-$ and $-NR^{22}-$, T is selected from the group consisting of oxo, thioxo and selenoxo, U is selected from the group consisting of —OH, —O-reporter group, —SH, —S reporter group —SeH, $-(C_1-C_{10})$-alkoxy, $(C_1-C_{10})$-alkyl, $-(C_6-C_{22})$-aryl, $-(C_6-C_{14})$-aryl-$(C_1-C_{10})$-alkyl, $-NR^{23}R^{24}$, and $-O-(C_1-C_{10})$-alkyl-$O-(C_1-C_{10})$-alkyl-$R^{25}$, or wherein $-NR^{23}R^{24}$ can together with N be a 5-6-membered heterocyclic ring, V is selected from the group consisting of oxy, sulfanediyl, $-CH_2-$, or $-NR^{22}-$, $R^{14}$ is selected from the group consisting of —H, —OH, $-(C_1-C_{10})$-alkoxy, $-(C_2-C_{10})$-alkenyloxy, -halogen, -azido, —O-allyl, —O-alkinyl, and —$NH_2$, $R^{22}$ is independently selected from the group of —H and $-(C_1-C_{10})$-alkyl, $R^{23}$ and $R^{24}$ are independently selected from the group consisting of $-(C_1-C_{10})$-alkyl, $-(C_1-C_{20})$-aryl, $-(C_6-C_{14})$-aryl-$(C_1-C_{10})$-alkyl, $-(C_1-C_6)$-alkyl-[NH$(CH_2)_c]_d-NR^{26}R^{27}$ and a reporter group, $R^{25}$ is selected from the group consisting of —H, —OH, -halogen, -amino, $-(C_1-C_{18})$-alkylamino, —COOH, —$CONH_2$ and —$COO(C_1-C_4)$-alkyl and a reporter group, $R^{26}$ and $R^{27}$ are independently selected from the group consisting from —H, $-(C_1-C_6)$-alkyl, and $-(C_1-C_4)$-alkoxy-$(C_1-C_6)$-alkyl and a reporter group, c is an integer from 2 to 6, d is an integer from 0 to 6, and B is a moiety of formula I, wherein any alkyl, alkenyl and alkynyl can be substituted or unsubstituted by one or more moieties selected from the group consisting of -halogen, —SH, —S—$(C_1-C_6)$-alkyl, $-(C_1-C_6)$-alkoxy, —OH, —$NR^5R^6$, —$COR^{11}$, —NH—$CONR^5R^6$, —NH—$CSNR^5R^6$ and —[O—$(CH_2)_r]_s$—$NR^5R^6$, r and s are independently of each other an integer of from 1 to 18, and any salts thereof.

9. The nucleic acid binding compound of claim 1, wherein the backbone comprises a moiety of the formula III

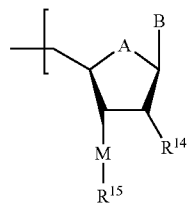

Formula III wherein

A is selected from the group consisting of O, S, $CH_2$ and $N-(C_1-C_6)$-alkyl, M is selected from the group consisting of oxy, sulfanediyl, $-NR^{22}-$, $-(C_1-C_{10})$-alkyl-, or —O—$(C_1-C_{10})$-alkyl-O—, and —S—$(C_1-C_{10})$-alkyl-O— and —$NR^{22}-$, $(C_1-C_6)$-alkyl-O—, $R^{22}$ is selected from the group of —H, $-(C_1-C_{10})$-alkyl, a protecting group and a reporter group, $R^{14}$ is selected from the group consisting of —H, —OH, $-(C_1-C_{10})$-alkoxy, $-(C_2-C_{10})$-alkenyloxy, $-(C_2-C_{10})$-alkynyloxy, -halogen, -azido, SH, $-(C_1-C_{10})$-alkylmercapto, O-reporter group, O-solid phase and —$NH_2$, $R^{15}$ is selected from the group consisting of —H, $-(C_1-C_6)$-alkyl, $-(C_2-C_{10})$-alkenyl, $-(C_2-C_{10})$-alkynyl, $-(C_2-C_{10})$-alkyl-carbonyl, $-(C_3-C_{19})$-alkenyl-carbonyl, $-(C_3-C_{19})$-alkynyl-carbonyl, $-(C_6-C_{14})$-aryl-$(C_1-C_{10})$-alkyl, a solid phase and a group of formula IV

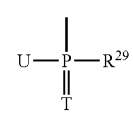

Formula IV wherein

T is selected from the group consisting of oxo, thioxo and selenoxo, and

U is selected from the group consisting of —OH, —O-reporter group, —SH, —SeH, $-(C_1-C_{10})$-alkoxy, $-(C_1-C_{10})$-alkyl, $-(C_6-C_{22})$-aryl, $-(C_6-C_{14})$-aryl-$(C_1-C_{10})$-alkyl, $-NR^{23}R^{24}$, and —O—$(C_1-C_{10})$-alkyl-O—$(C_1-C_{10})$-alkyl-$R^{25}$, or wherein $NR^{23}R^{24}$ can together with N be a 5-6-membered heterocyclic ring, $R^{23}$ and $R^{24}$ are independently selected from the group consisting of $-(C_1-C_{10})$-alkyl, $-(C_1-C_{20})$-aryl, $-(C_6-C_{14})$-aryl-$(C_1C_{10})$-alkyl, $-(C_1-C_6)$-alkyl-[NH$(CH_2)_c]_d-NR^{26}R^{27}$, $R^{25}$ is selected from the group consisting of —H, —OH, -halogen, -amino, $-(C_1-C_{18})$-alkylamino, —COOH, —$CONH_2$ and —$COO(C_1-C_4)$-alkyl, $R^{26}$ and $R^{27}$ are independently selected from the group consisting from —H, $-(C_1-C_6)$-alkyl, and $-(C_1-C_4)$-alkoxy-$(C_1-C_6)$-alkyl $R^{29}$ is selected from the group consisting of —$OR^{30}$ and —$SR^{30}$, $R^{30}$ is selected from the group consisting of —H, $-(C_1-C_{10})$-alkyl, $-(C_2-C_{10})$-alkenyl, $-(C_6-C_{22})$-aryl, a protecting group, a solid phase and a reporter group c is an integer from 2 to 6, d is an integer from 0 to 6, and B is the link to a moiety of formula I, wherein any alkyl, alkenyl and alkynyl can be substituted or unsubstituted by one or more moieties selected from the group consisting of -halogen, —SH, —S—$(C_1$-$C_6)$-alkyl, —$(C_1$-$C_6)$-alkoxy, —OH, —$NR^5R^6$, —$COR^{11}$, —NH—$CONR^5R^6$, —NH—$CSNR^5R^6$ and —[O—$(CH_2)_r]_s$—$NR^5R^6$.

r and s are independently of each other an integer of from 1 to 18.

10. The nucleic acid binding compound of claim 1, wherein said backbone comprises a moiety of the formula V

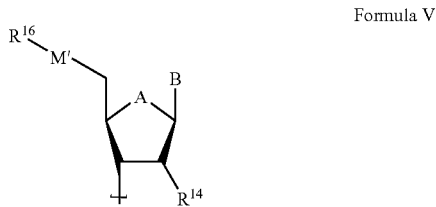

Formula V wherein

A is selected from the group consisting of O, S, $CH_2$ and N—$(C_1$-$C_6)$-alkyl, M' is selected from the group consisting of oxy, sulfanediyl, —$NR^{22}$—, —$(C_1$-$C_{10})$-alkyl, or —O—$(C_1$-$C_{10})$-alkyl-O—, and —S—$(C_1$-$C_{10})$-alkyl-O— and —$NR^{22}$—$(C_1$-$C_6)$-alkyl-O—, $R^{22}$ is selected from the group of —H, a protecting group, a reporter group and —$(C_1$-$C_{10})$-alkyl, $R^{14}$ is selected from the group consisting of —H, —OH, —$(C_1$-$C_{10})$-alkoxy, —$(C_2$-$C_{10})$-alkenyloxy, —$(C_2$-$C_{10})$-alkynyloxy, -halogen, azido, —SH, —S—$(C_1$-$C_6)$-alkylmercapto, O-reporter group, O-solid phase and $NH_2$, $R^{16}$ is selected from the group consisting of —H, —$(C_1$-$C_8)$-alkyl, —$(C_2$-$C_{18})$-alkenyl, —$(C_2$-$C_{18})$-alkynyl, —$(C_2$-$C_{18})$-alkyl-carbonyl, —$(C_3$-$C_{19})$-alkenyl-carbonyl, —$(C_3$-$C_{19})$-alkynyl-arbonyl, —$(C_6$-$C_{14})$-aryl-$(C_1$-$C_8)$-alkyl, a protective group or a compound have the formula IV

Formula IV wherein

T is selected from the group consisting of oxo, thioxo and selenoxo,

U is selected from the group consisting of —OH, —SH, —SeH, —$(C_1$-$C_{10})$-alkoxy, —$(C_1$-$C_{10})$-alkyl, —$(C_6$-$C_{22})$-aryl, —$(C_6$-$C_{14})$-aryl-$(C_1$-$C_{10})$-alkyl, —$NR^{23}R^{24}$, and —O—$(C_1$-$C_{10})$-alkyl-O—$(C_1$-$C_{10})$-alkyl-$R^{25}$, wherein $NR^{23}R^{24}$ can together with N be a 5-6-membered heterocyclic ring, $R^{23}$ and $R^{24}$ are independently selected from the group consisting of —$(C_1$-$C_{10})$-alkyl, —$(C_1$-$C_{20})$-aryl, —$(C_6$-$C_{14})$-aryl-$(C_1$-$C_{10})$-alkyl, —$(C_1$-$C_6)$-alkyl-[NH$(CH_2)_c]_d$—$NR^{26}R^{27}$, $R^{25}$ is selected from the group consisting of —H, —OH, -halogen, -amino, —$(C_1$-$C_{18})$-alkylamino, —COOH, —$CONH_2$ and —COO$(C_1$-$C_4)$-alkyl, $R^{26}$ and $R^{27}$ are independently selected from the group consisting from —H, —$(C_1$-$C_6)$-alkyl, and —$(C_1$-$C_4)$-alkoxy-$(C_1$-$C_6)$-alkyl $R^{29}$ is selected from the group consisting of —$OR^{30}$ and —$SR^{30}$, $R^{30}$ is selected from the group consisting of —H, —$(C_1$-$C_{10})$-alkyl, —$(C_2$-$C_{10})$-alkenyl, —$(C_6$-$C_{22})$-aryl, a protecting group, a solid phase and a reporter group, and c is an integer from 2 to 6, d is an integer from 0 to 6, and B is the link to a moiety of formula I, wherein any alkyl, alkenyl and alkynyl can be substituted or unsubstituted by one or more moieties selected from the group consisting of -halogen, —SH, —S—$(C_1$-$C_6)$-alkyl, —$(C_1$-$C_6)$-alkoxy, —OH, —$NR^5R^6$, —$COR^{11}$, —NH—$CONR^5R^6$, —NH—$CSNR^5R^6$ and —[O—$(CH_2)_r]_s$—$NR^5R^6$, r and s are independently of each other an integer of from 1 to 18, and any salts thereof.

11. The compound of claim 10, wherein M' is O, $R^{16}$ is H and $R^{14}$ is selected from the group consisting of —H and —OH.

12. A nucleic acid binding compound comprising a backbone, said backbone having attached heterocyclic groups wherein at least one of said heterocyclic groups has the formula I wherein

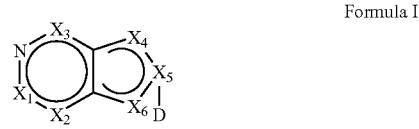

Formula I $X_1$ is independently from $X_4$, $X_5$ and $X_6$ selected from the group of N and $CR^1$, and $X_1$ is $CR^1$ if each of $X_2$ and $X_3$ is N, $X_2$ is independently from $X_4$, $X_5$ and $X_6$ selected from the group of N and $CR^2$, and $X_2$ is $CR^2$ if each of $X_1$ and $X_3$ is N, $X_3$ is independently from $X_4$, $X_5$ and $X_6$ selected from the group of N and $CR^3$, and $X_3$ is $CR^3$ if each of $X_1$ and $X_2$ is N, $X_4$ is independently from $X_1$, $X_2$ and $X_3$ selected from the group of N, $NR^{35}$ and $CR^4$, if $X_5$ is C and $X_6$ is $NR^{35}$, then $X_4$ is $CR^4$ or N, if $X_5$ is C and $X_6$ is N, then $X_4$ is $NR^{35}$, and if $X_5$ is C and $X_6$ is $CR^{34}$, then $X_4$ is $NR^{35}$, and if $X_5$ is N, then $X_4$ is N or $CR^4$, $X_5$ is independently from $X_1$, $X_2$, $X_3$, $X_4$ and $X_6$ selected from the group of N and C, $X_6$ is independently from $X_1$, $X_2$ and $X_3$ selected from the group of N, $NR^{35}$ and $CR^{34}$, if $X_5$ is C and $X_4$ is NR then $X_6$ is $CR^{34}$ or N, if $X_5$ is C and $X_4$ is N, then $X_6$ is $NR^{35}$, if $X_5$ is C and $X_4$ is $CR^4$, then $X_6$ is $NR^{35}$, and if $X_5$ is N, then $X_6$ is N or $CR^{34}$, $R^1$, $R^2$, $R^3$, $R^4$ and $R^{34}$ are independently selected from the group consisting of —H, —halogen, —$OR^{13}$, —$SR^{19}$, —$(C_1$-$C_{10})$-alkyl, —$(C_2$-$C_{10})$-alkenyl, —$(C_2$-$C_{10})$-alkynyl, —$NO_2$, —$NR^5R^6$, -cyano, and —C(=O)$R^{11}$, $R^{11}$ is selected from the group consisting of —OH, —$(C_1$-$C_6)$-alkoxy, —$(C_6$-$C_{22})$-aryloxy, and $NHR^{12}$, $R^5$, $R^6$, $R^{12}$, $R^{13}$, $R^{19}$ and $R^{35}$ are selected independently from the group consisting of —H, —($C_1$-$C_{10}$)-alkyl, —($C_2$-$C_{10}$)-alkenyl, —($C_2$-$C_{10}$)-alkinyl, —($C_6$-$C_{22}$)-aryl, a protecting group and a reporter group, r and s are independently of each other an integer of from 1 to 18, D is the position of attachment of the group to the rest of the nucleic acid binding compound, said alkyl, alkenyl and alkynyl being unsubstituted or substituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—($CH_2$)$_r$]$_s$—$NR^5R^6$ and wherein said nucleic acid binding compound contains at least one reporter group with the proviso that if $X_4$, $X_5$, $X_6$ of the heterocyclic group of the general formula I are N and $X_1$ is $CR^1$, $X_2$ is N and $X_3$ is $CR^3$, $R^1$ and $R^3$ are not H, OH, $NH_2$ or protected $NH_2$.

13. A binding product comprising the nucleic acid binding compound of claim 1 and a nucleic acid.

14. A precursor for the synthesis of a nucleic acid binding compound comprising a backbone, which comprises a moiety of the formula VI

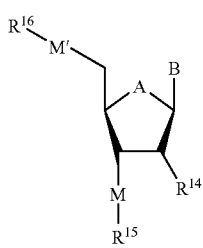

Formula VI

A is selected from the group consisting of O, S, $CH_2$ and N—($C_1$-$C_6$)-alkyl, M and M' are independently selected from the group consisting of oxy, sulfanediyl, —$NR^{22}$, —($C_1$-$C_{10}$)-alkyl-, or —O—($C_1$-$C_{10}$)-alkyl-O—, and —S—($C_1$-$C_{10}$)-alkyl-O— and —$NR^{22}$—($C_1$-$C_6$)-alkyl-O—, $R^{22}$ is selected from the group of —H, —($C_1$-$C_{10}$)-alkyl, a protecting group and a reporter group, $R^{14}$ is selected from the group consisting of —H, —$OR^{31}$, —($C_1$-$C_{10}$)-alkoxy, O-protecting group, S-protecting group, $NH_2$-protecting group, —($C_2$-$C_{10}$)-alkenyloxy, —($C_2$-$C_{10}$)-alkynyloxy, -halogen, -azido, SH, —($C_1$-$C_{10}$)-alkylmercapto, —$NH_2$ and —O-solid phase, $R^{15}$ and $R^{16}$ are independently selected from the group consisting of —H, —($C_1$-$C_6$)-alkyl, —($C_2$-$C_{10}$)-alkenyl, —($C_2$-$C_{10}$)-alkynyl, —($C_2$-$C_{10}$)-alkyl-carbonyl, —($C_3$-$C_{19}$)-alkenyl-carbonyl, —($C_3$-$C_{19}$)-alkynyl-carbonyl, —($C_6$-$C_{14}$)-aryl-($C_1$-$C_{10}$)-alkyl, protecting group and a solid phase B is the link to a moiety of the formula I,

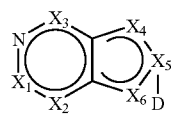

Formula I wherein $X_1$ is independently from $X_4$, $X_5$ and $X_6$ selected from the group of N and $CR^1$, and $X_1$ is $CR^1$ if each of $X_2$ and $X_3$ is N, $X_2$ is independently from $X_4$, $X_5$ and $X_6$ selected from the group of N and $CR^2$, and $X_2$ is $CR^2$ if each of $X_1$ and $X_3$ is N, $X_3$ is independently from $X_4$, $X_5$ and $X_6$ selected from the group of N and $CR^3$, and $X_3$ is $CR^3$ if each of $X_1$ and $X_2$ is N, $X_4$ is independently from $X_1$, $X_2$ and $X_3$ selected from the group of N, $NR^{35}$ and $CR^4$, if $X_5$ is C and $X_6$ is $NR^{35}$, then $X_4$ is $CR^4$ or N, if $X_5$ is C and $X_6$ is N, then $X_4$ is $NR^{35}$, and if $X_5$ is C and $X_6$ is $CR^{34}$, then $X_4$ is $NR^{35}$, and if $X_5$ is N, then $X_4$ is N or $CR^4$, $X_5$ is independently from $X_1$, $X_2$, $X_3$, $X_4$ and $X_6$ selected from the group of N and C, $X_6$ is independently from $X_1$, $X_2$ and $X_3$ selected from the group of N, $NR^{35}$ and $CR^{34}$, if $X_5$ is C and $X_4$ is $NR^{35}$, then $X_6$ is $CR^{34}$ or N, if $X_5$ is C and $X_4$ is N, then $X_6$ is $NR^{35}$, if $X_5$ is C and $X_4$ is $CR^4$, then $X_6$ is $NR^{35}$, and if $X_5$ is N, then $X_6$ is N or $CR^{34}$, $R^1$, $R^2$, $R^3$, $R^4$ and $R^{34}$ are independently selected from the group consisting of —H, -halogen, —$OR^{13}$, —$SR^{19}$, —($C_1$-$C_{10}$)-alkyl, —($C_2$-$C_{10}$)-alkenyl, —($C_2$-$C_{10}$)-alkynyl, —$NO_2$, —$NR^5R^6$, -cyano, and —C(=O)$R^{11}$, $R^{11}$ is selected from the group consisting of —OH, —($C_1$-$C_6$)-alkoxy, —($C_6$-$C_{22}$)-aryloxy, and $NHR^{12}$, $R^5$, $R^6$, $R^{12}$, $R^{13}$, $R^{19}$ and $R^{35}$ are selected independently from the group consisting of —H, —($C_1$-$C_{10}$)-alkyl, —($C_2$-$C_{10}$)-alkenyl, —($C_2$-$C_{10}$)-alkinyl, —($C_6$-$C_{22}$)-aryl, a protecting group and a reporter group, D is the position of attachment of the group to the backbone, wherein any alkyl, alkenyl and alkynyl can be substituted or unsubstituted by one or more moieties selected from the group consisting of -halogen, —SH, —S—($C_1$-$C_6$)-alkyl, —($C_1$-$C_6$)-alkoxy, —OH, —$NR^5R^6$, —$COR^{11}$, —NH—$CONR^5R^6$, —NH—$CSNR^5R^6$ and —[O—($CH_2$)$_r$]$_s$—$NR^5R^6$.

r and s are independently of each other an integer of from 1 to 18, wherein one of $R^{14}$, $R^{15}$ or $R^{16}$ is a solid phase.

15. A precursor or intermediate for the synthesis of a nucleic acid binding compound, comprising a backbone which comprises a moiety of the formula III

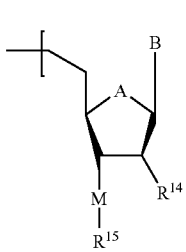

Formula III wherein

A is selected from the group consisting of O, S, $CH_2$ and N—($C_1$-$C_6$)-alkyl, M is selected from the group consisting of oxy, sulfanediyl, —NR$^{22}$—, —(C$_1$-C$_{10}$)-alkyl-, or —O—(C$_1$-C$_{10}$)-alkyl-O—, and —S—(C$_1$-C$_{10}$)-alkyl-O— and —NR$^{22}$—(C$_1$-C$_6$)-alkyl-O—, R$^{22}$ is selected from the group of —H, —(C$_1$-C$_{10}$)-alkyl, a protecting group and a reporter group, R$^{14}$ is selected from the group consisting of —H, —OH, —(C$_1$-C$_{10}$)-alkoxy, —(C$_2$-C$_{10}$)-alkenyloxy, —(C$_2$-C$_{10}$)-alkynyloxy, -halogen, -azido, SH, —(C$_1$-C$_{10}$)-alkylmercapto, O-reporter group, O-solid phase and —NH$_2$, R$^{15}$ is selected from the group consisting of —H, —(C$_1$-C$_6$)-alkyl, —(C$_2$-C$_{10}$)-alkenyl, —(C$_2$-C$_{10}$)-alkynyl, —(C$_2$-C$_{10}$)-alkyl-carbonyl, —(C$_3$-C$_{19}$)-alkenyl-carbonyl, —(C$_3$-C$_{19}$)-alkynyl -carbonyl, —(C$_6$-C$_{14}$)-aryl-(C$_1$-C$_{10}$)-alkyl and a solid phase, B is the link to a moiety of the formula I,

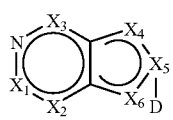

Formula I wherein

X$_1$ is independently from X$_4$, X$_5$ and X$_6$ selected from the group of N and CR$^1$, and X$_1$ is CR$^1$ if each of X$_2$ and X$_3$ is N, X$_2$ is independently from X$_4$, X$_5$ and X$_6$ selected from the group of N and CR$^2$, and X$_2$ is CR$^2$ if each of X$_1$ and X$_3$ is N, X$_3$ is independently from X$_4$, X$_5$ and X$_6$ selected from the group of N and CR$^3$, and X$_3$ is CR$^3$ if each of X$_1$ and X$_2$ is N, X$_4$ is independently from X$_1$, X$_2$ and X$_3$ selected from the group of N, NR$^{35}$ and CR$^4$, if X$_5$ is C and X$_6$ is NR$^{35}$, then X$_4$ is CR$^4$ or N, if X$_5$ is C and X$_6$ is N, then X$_4$ is NR$^{35}$, and if X$_5$ is C and X$_6$ is CR$^{34}$, then X$_4$ is NR$^{35}$, and if X$_5$ is N, then X$_4$ is N or CR$^4$, X$_5$ is independently from X$_1$, X$_2$, X$_3$, X$_4$ and X$_6$ selected from the group of N and C, X$_6$ is independently from X$_1$, X$_2$ and X$_3$ selected from the group of N, NR$^{35}$ and CR$^{34}$, if X$_5$ is C and X$_4$ is NR$^{35}$, then X$_6$ is CR$^{34}$ or N, if X$_5$ is C and X$_4$ is N, then X$_6$ is NR$^{35}$, if X$_5$ is C and X$_4$ is CR$^4$, then X$_6$ is NR$^{35}$, and if X$_5$ is N, then X$_6$ is N or CR$^{34}$, R$^1$, R$^2$, R$^3$, R$^4$ and R$^{34}$ are independently selected from the group consisting of —H, -halogen, —OR$^{13}$, —SR$^{19}$, —(C$_1$-C$_{10}$)-alkyl, —(C$_2$-C$_{10}$)-alkenyl, —(C$_2$-C$_{10}$)-alkynyl, —NO$_2$, —NR$^5$R$^6$, -cyano, and —C(=O)R$^{11}$, R$^{11}$ is selected from the group consisting of —OH, —(C$_1$-C$_6$)-alkoxy, —(C$_6$-C$_{22}$)-aryloxy, and NHR$^{12}$, R$^5$, R$^6$, R$^{12}$, R$^{13}$, R$^{19}$ and R$^{35}$ are selected independently from the group consisting of —H, —(C$_1$-C$_{10}$)-alkyl, —(C$_2$-C$_{10}$)-alkenyl, —(C$_2$-C$_{10}$)-alkinyl, —(C$_6$-C$_{22}$)-aryl, a protecting group and a reporter group, D is the position of attachment of the group to the backbone, wherein any alkyl, alkenyl and alkynyl can be substituted or unsubstituted by one or more moieties selected from the group consisting of -halogen, —SH, —S—(C$_1$-C$_6$)-alkyl, —(C$_1$-C$_6$)-alkoxy, —OH, —NR$^5$R$^6$, —COR$^{11}$, —NH—CONR$^5$R$^6$, —NH—CSNR$^5$R$^6$ and —[O—(CH$_2$)$_r$]$_s$—NR$^5$R$^6$.

r and s are independently of each other an integer of from 1 to 18, wherein R$^{14}$ is O-solid phase or R$^{15}$ is solid phase.

16. A precursor for the synthesis of a nucleic acid binding compound comprising a backbone, which comprises a heterocyclic group of the formula I

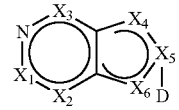

Formula I wherein

X$_1$ is independently from X$_4$, X$_5$ and X$_6$ selected from the group of N and CR$^1$, and X$_1$ is CR$^1$ if each of X$_2$ and X$_3$ is N, X$_2$ is independently from X$_4$, X$_5$ and X$_6$ selected from the group of N and CR$^2$, and X$_2$ is CR$^2$ if each of X$_1$ and X$_3$ is N, X$_3$ is independently from X$_4$, X$_5$ and X$_6$ selected from the group of N and CR$^3$, and X$_3$ is CR$^3$ if each of X$_1$ and X$_2$ is N, X$_4$ is independently from X$_1$, X$_2$ and X$_3$ selected from the group of N, NR$^{35}$ and CR$^4$, if X$_5$ is C and X$_6$ is NR$^{35}$, then X$_4$ is CR$^4$ or N, if X$_5$ is C and X$_6$ is N, then X$_4$ is NR$^{35}$, and if X$_5$ is C and X$_6$ is CR$^{34}$, then X$_4$ is NR$^{35}$, and if X$_5$ is N, then X$_4$ is N or CR$^4$, X$_5$ is independently from X$_1$, X$_2$, X$_3$, X$_4$ and X$_6$ selected from the group of N and C, X$_6$ is independently from X$_1$, X$_2$ and X$_3$ selected from the group of N, NR$^{35}$ and CR$^{34}$, if X$_5$ is C and X$_4$ is NR$^{35}$, then X$_6$ is CR$^{34}$ or N, if X$_5$ is C and X$_4$ is N, then X$_6$ is NR$^{35}$, if X$_5$ is C and X$_4$ is CR$^4$, then X$_6$ is NR$^{35}$, and if X$_5$ is N, then X$_6$ is N or CR$^{34}$, R$^1$, R$^2$, R$^3$, R$^4$ and R$^{34}$ are independently selected from the group consisting of —H, -halogen, —OR$^{13}$, —SR$^{19}$, —(C$_1$-C$_{10}$)-alkyl, —(C$_2$-C$_{10}$)-alkenyl, —(C$_2$-C$_{10}$)-alkynyl, —NO$_2$, —NR$^5$R$^6$, -cyano, and —C(=O)R$^{11}$, R$^{11}$ is selected from the group consisting of —OH, —(C$_1$-C$_6$)-alkoxy, —(C$_6$-C$_{22}$)-aryloxy, and NHR$^{12}$, R$^5$, R$^6$, R$^{12}$, R$^{13}$, R$^{19}$ and R$^{35}$ are selected independently from the group consisting of —H, —(C$_1$-C$_{10}$)-alkyl, —(C$_2$-C$_{10}$)-alkenyl, —(C$_2$-C$_{10}$)-alkinyl, —(C$_6$-C$_{22}$)-aryl, a protecting group, a solid phase and a reporter group, r and s are independently of each other an integer of from 1 to 18, D is the position of attachment of the group to the backbone, said alkyl, alkenyl and alkynyl being unsubstituted or substituted by one or more moieties selected from the group consisting of -halogen, —SH, —S—(C$_1$-C$_6$)-alkyl, —(C$_1$-C$_6$)-alkoxy, —OH, —NR$^5$R$^6$, —COR$^{11}$, —NH—CONR$^5$R$^6$, —NH—CSNR$^5$R$^6$ and —[O—(CH$_2$)$_r$]$_s$—NR$^5$R$^6$ wherein either said backbone is solid phase bound or wherein at least one of R$^5$, R$^6$, R$^{12}$, R$^{13}$, R$^{19}$ and R$^{35}$ is solid phase.

* * * * *

UNITED STATES PATENT AND TRADEMARK OFFICE
CERTIFICATE OF CORRECTION

PATENT NO. : 7,566,775 B2
APPLICATION NO. : 11/338149
DATED : July 28, 2009
INVENTOR(S) : Frank Seela et al.

It is certified that error appears in the above-identified patent and that said Letters Patent is hereby corrected as shown below:

claim 1, column 47, line 36: "$X_5$" should read "$X_3$";

claim 1, column 47, line 39: "$X_2$" should read "$X_3$";

claim 1, column 48, line 44: "2'-deoxt-β-D" should read "2'-deoxy-β-D."

Signed and Sealed this

Sixteenth Day of March, 2010

David J. Kappos
*Director of the United States Patent and Trademark Office*

SEQUENCE LISTING

<160> NUMBER OF SEQ ID NOS: 21

<210> SEQ ID NO 1
<211> LENGTH: 12
<212> TYPE: DNA
<213> ORGANISM: Artificial Sequence
<220> FEATURE:
<223> OTHER INFORMATION: Synthetic; oligonucleotide designated R1 useful
      in a model oligonucleotide hybridization system for analysing
      properties of nucleotide analogues as described in the present
      application

<400> SEQUENCE: 1
taggtcaata ct                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetic; oligonucleotide designated R2 useful
      in a model oligonucleotide hybridization system for analysing
      properties of nucleotide analogues as described in the present
      application

<400> SEQUENCE: 2
agtattgacc at                                                          12

<210> SEQ ID NO 3
<211> LENGTH: 12
<212> TYPE: DNA
<213> ORGANISM: Artificial Sequence
<220> FEATURE:
<223> OTHER INFORMATION: Synthetic; oligonucleotide designated 89 useful
      in a model oligonucleotide hybridization system for analysing
      properties of nucleotide analogues as described in the present
      application
<220> FEATURE:
<221> NAME/KEY: modified_base
<222> LOCATION: (8)
<223> OTHER INFORMATION: N8 linked 8-aza-7-deaza-2'-deoxyadenosine

<400> SEQUENCE: 3
agtattgncc ta                                                          12

<210> SEQ ID NO 4
<211> LENGTH: 12
<212> TYPE: DNA
<213> ORGANISM: Artificial Sequence
<220> FEATURE:
<223> OTHER INFORMATION: Synthetic; oligonucleotide designated 98 useful
      in a model oligonucleotide hybridization system for analysing
      properties of nucleotide analogues as described in the present
      application

<400> SEQUENCE: 4
taggccaata ct                                                          12

```
<210> SEQ ID NO 5
<211> LENGTH: 12
<212> TYPE: DNA
<213> ORGANISM: Artificial Sequence
<220> FEATURE:
<223> OTHER INFORMATION: Synthetic; oligonucleotide designated 97 useful
      in a model oligonucleotide hybridization system for analysing
      properties of nucleotide analogues as described in the present
      application

<400> SEQUENCE: 5
taggacaata ct                                                           12

<210> SEQ ID NO 6
<211> LENGTH: 12
<212> TYPE: DNA
<213> ORGANISM: Artificial Sequence
<220> FEATURE:
<223> OTHER INFORMATION: Synthetic; oligonucleotide designated 99 useful
      in a model oligonucleotide hybridization system for analysing
      properties of nucleotide analogues as described in the present
      application

<400> SEQUENCE: 6
tagggcaata ct                                                           12

<210> SEQ ID NO 7
<211> LENGTH: 12
<212> TYPE: DNA
<213> ORGANISM: Artificial Sequence
<220> FEATURE:
<223> OTHER INFORMATION: Synthetic; oligonucleotide designated 96 useful
      in a model oligonucleotide hybridization system for analysing
      properties of nucleotide analogues as described in the present
      application
<220> FEATURE:
<221> NAME/KEY: modified_base
<222> LOCATION: (8)
<223> OTHER INFORMATION: N8 linked 8-aza-7-deaza-2'-deoxyadenosine

<400> SEQUENCE: 7
taggtcanta ct                                                           12

<210> SEQ ID NO 8
<211> LENGTH: 12
<212> TYPE: DNA
<213> ORGANISM: Artificial Sequence
<220> FEATURE:
<223> OTHER INFORMATION: Synthetic; oligonucleotide designated 105
      useful in a model oligonucleotide hybridization system for
      analysing properties of nucleotide analogues as described in the
      present application

<400> SEQUENCE: 8
agtactgacc ta                                                           12

<210> SEQ ID NO 9
<211> LENGTH: 12
<212> TYPE: DNA
<213> ORGANISM: Artificial Sequence
<220> FEATURE:
<223> OTHER INFORMATION: Synthetic; oligonucleotide designated 104
      useful in a model oligonucleotide hybridization system for
      analysing properties of nucleotide analogues as described in the
      present application

<400> SEQUENCE: 9
agtaatgacc ta                                                           12
```

-continued

```
<210> SEQ ID NO 10
<211> LENGTH: 12
<212> TYPE: DNA
<213> ORGANISM: Artificial Sequence
<220> FEATURE:
<223> OTHER INFORMATION: Synthetic; oligonucleotide designated 103
      useful in a model oligonucleotide hybridization system for
      analysing properties of nucleotide analogues as described in the
      present application

<400> SEQUENCE: 10
agtagtgacc ta                                                             12

<210> SEQ ID NO 11
<211> LENGTH: 12
<212> TYPE: DNA
<213> ORGANISM: Artificial Sequence
<220> FEATURE:
<223> OTHER INFORMATION: Synthetic; oligonucleotide designated 80 useful
      in a model oligonucleotide hybridization system for analysing
      properties of nucleotide analogues as described in the present
      application
<220> FEATURE:
<221> NAME/KEY: modified_base
<222> LOCATION: (7)
<223> OTHER INFORMATION: N8 linked 8-aza-7-deaza-2'-deoxyadenosine
<220> FEATURE:
<221> NAME/KEY: modified_base
<222> LOCATION: (8)
<223> OTHER INFORMATION: N8 linked 8-aza-7-deaza-2'-deoxyadenosine

<400> SEQUENCE: 11
taggtcnnta ct                                                             12

<210> SEQ ID NO 12
<211> LENGTH: 11
<212> TYPE: DNA
<213> ORGANISM: Artificial Sequence
<220> FEATURE:
<223> OTHER INFORMATION: Synthetic; oligonucleotide designated 119
      useful in a model oligonucleotide hybridization system for
      analysing  properties of nucleotide analogues as described in the
      present application
<220> FEATURE:
<221> NAME/KEY: modified_base
<222> LOCATION: (7)
<223> OTHER INFORMATION: abasic linker-group at 3-OH-group of sugar

<400> SEQUENCE: 12 agtattgcc ta                                                              11

<210> SEQ ID NO 13
<211> LENGTH: 12
<212> TYPE: DNA
<213> ORGANISM: Artificial Sequence
<220> FEATURE:
<223> OTHER INFORMATION: Synthetic; oligonucleotide designated E13
      useful in a model oligonucleotide hybridization system for
      analysing properties of nucleotide analogues as described in the
      present application

<400> SEQUENCE: 13
taggacaata ct                                                             12

<210> SEQ ID NO 14
<211> LENGTH: 12
<212> TYPE: DNA
<213> ORGANISM: Artificial Sequence
<220> FEATURE:
<223> OTHER INFORMATION: Synthetic; oligonucleotide designated E11
      useful in a model oligonucleotide hybridization system for
``` analysing properties of nucleotide analogues as described in the
present application

<400> SEQUENCE: 14
tagggcaata ct                                                          12

<210> SEQ ID NO 15
<211> LENGTH: 11
<212> TYPE: DNA
<213> ORGANISM: Artificial Sequence
<220> FEATURE:
<223> OTHER INFORMATION: Synthetic; oligonucleotide designated 118
      useful  in a model oligonucleotide hybridization system for
      analysing properties of nucleotide analogues as described in the
      present application
<220> FEATURE:
<221> NAME/KEY: modified_base
<222> LOCATION: (7)
OTHER INFORMATION: abasic linker-group at 3-OH-group of sugar

<400> SEQUENCE: 15 taggtcata ct                                                           11

<210> SEQ ID NO 16
<211> LENGTH: 12
<212> TYPE: DNA
<213> ORGANISM: Artificial Sequence
<220> FEATURE:
<223> OTHER INFORMATION: Synthetic; oligonucleotide designated HD47
      useful  in a model oligonucleotide hybridization system for
      analysing  properties of nucleotide analogues as described in the
      present application
<220> FEATURE:
<221> NAME/KEY: modified_base
<222> LOCATION: (2)
<223> OTHER INFORMATION: C8 linked 7-deaza-2'-deoxyguanosine
<220> FEATURE:
<221> NAME/KEY: modified_base
<222> LOCATION: (7)
<223> OTHER INFORMATION: C8 linked 7-deaza-2'-deoxyguanosine

<400> SEQUENCE: 16
antattnacc ta                                                          12

<210> SEQ ID NO 17
<211> LENGTH: 12
<212> TYPE: DNA
<213> ORGANISM: Artificial Sequence
<220> FEATURE:
<223> OTHER INFORMATION: Synthetic; oligonucleotide designated HD48
      useful in a model oligonucleotide hybridization system for
      analysing properties of nucleotide analogues as described in the
      present application
<220> FEATURE:
<221> NAME/KEY: modified_base
<222> LOCATION: (3)
<223> OTHER INFORMATION: C8 linked 7-deaza-2'-deoxyguanosine
<220> FEATURE:
<221> NAME/KEY: modified_base
<222> LOCATION: (4)
<223> OTHER INFORMATION: C8 linked 7-deaza-2'-deoxyguanosine

<400> SEQUENCE: 17
tanntcaata ct                                                          12

<210> SEQ ID NO 18
<211> LENGTH: 12
<212> TYPE: DNA
<213> ORGANISM: Artificial Sequence
<220> FEATURE:
<223> OTHER INFORMATION: Synthetic; oligonucleotide designated HD75

-continued

```
      useful in a model oligonucleotide hybridization system for
      analysing properties of nucleotide analogues as described in the
      present application
<220> FEATURE:
<221> NAME/KEY: modified_base
<222> LOCATION: (7)
<223> OTHER INFORMATION: C8 linked 7-deaza-2'-deoxyguanosine

<400> SEQUENCE: 18
agtattnacc ta                                                            12

<210> SEQ ID NO 19
<211> LENGTH: 12
<212> TYPE: DNA
<213> ORGANISM: Artificial Sequence
<220> FEATURE:
<223> OTHER INFORMATION: Synthetic; oligonucleotide designated HD76
      useful in a model oligonucleotide hybridization system for
      analysing properties of nucleotide analogues as described in the
      present application
<220> FEATURE:
<221> NAME/KEY: modified_base
<222> LOCATION: (4)
<223> OTHER INFORMATION: C8 linked 7-deaza-2'-deoxyguanosine

<400> SEQUENCE: 19
tagntcaata ct                                                            12

<210> SEQ ID NO 20
<211> LENGTH: 12
<212> TYPE: DNA
<213> ORGANISM: Artificial Sequence
<220> FEATURE:
<223> OTHER INFORMATION: Synthetic; oligonucleotide designated HD86
      useful in a model oligonucleotide hybridization system for
      analysing properties of nucleotide analogues as described in the
      present application
<220> FEATURE:
<221> NAME/KEY: modified_base
<222> LOCATION: (3)
<223> OTHER INFORMATION: 5-methyl-isoCytidine
<220> FEATURE:
<221> NAME/KEY: modified_base
<222> LOCATION: (4)
<223> OTHER INFORMATION: 5-methyl-isoCytidine
<220> FEATURE:
<221> NAME/KEY: modified_base
<222> LOCATION: (6)
<223> OTHER INFORMATION: C8 linked 7-deaza-2'-deoxyguanosine
<220> FEATURE:
<221> NAME/KEY: modified_base
<222> LOCATION: (11)
<223> OTHER INFORMATION: C8 linked 7-deaza-2'-deoxyguanosine

<400> SEQUENCE: 20
atnnanttat na                                                            12

<210> SEQ ID NO 21
<211> LENGTH: 12
<212> TYPE: DNA
<213> ORGANISM: Artificial Sequence
<220> FEATURE:
<223> OTHER INFORMATION: Synthetic; oligonucleotide designated HD87
      useful in a model oligonucleotide hybridization system for
      analysing properties of nucleotide analogues as described in the
      present application
<220> FEATURE:
<221> NAME/KEY: modified_base
<222> LOCATION: (2)
<223> OTHER INFORMATION: 5-methyl-isoCytidine
<220> FEATURE:
<221> NAME/KEY: modified_base
<222> LOCATION: (7)
```

```
<223> OTHER INFORMATION: 5-methyl-isoCytidine
<220> FEATURE:
<221> NAME/KEY: modified_base
<222> LOCATION: (9)
<223> OTHER INFORMATION: C8 linked 7-deaza-2'-deoxyguanosine
<220> FEATURE:
<221> NAME/KEY: modified_base
<222> LOCATION: (10)
<223> OTHER INFORMATION: C8 linked 7-deaza-2'-deoxyguanosine

<400> SEQUENCE: 21
tnataantnn at                                                          12
```